(12) United States Patent
Sodroski et al.

(10) Patent No.: US 9,776,963 B2
(45) Date of Patent: Oct. 3, 2017

(54) SMALL MOLECULE CD4 MIMETICS AND USES THEREOF

(75) Inventors: Joseph G. Sodroski, Medford, MA (US); Navid Madani, Newton, MA (US); Arne Schön, Baltimore, MD (US); Judith M. LaLonde, Havertown, PA (US); Joel R. Courter, Glen Mills, PA (US); Takahiro Soeta, Ishikawa (JP); Danny Ng, Daly City, CA (US); Ernesto Freire, Baltimore, MD (US); Amos B. Smith, III, Merion, PA (US); Amy M. Princiotto, Attleboro, MA (US); Matthew Le-Khac, Brooklyn, NY (US); Wayne A. Hendrickson, New York, NY (US)

(73) Assignees: The Trustees of the University of Pennsylvania, Philadelphia, PA (US); Dana-Farber Cancer Institute, Inc., Boston, MA (US); The Johns Hopkins University, Baltimore, MD (US); Bryn Mawr College, Bryn Mawr, PA (US); The Trustees of Columbia University in the City of New York, New York, NY (US)

( * ) Notice: Subject to any disclaimer, the term of this patent is extended or adjusted under 35 U.S.C. 154(b) by 1744 days.

(21) Appl. No.: 13/128,549

(22) PCT Filed: Nov. 10, 2009

(86) PCT No.: PCT/US2009/006049
§ 371 (c)(1),
(2), (4) Date: Jan. 3, 2012

(87) PCT Pub. No.: WO2010/053583
PCT Pub. Date: May 14, 2010

(65) Prior Publication Data
US 2012/0122834 A1    May 17, 2012

Related U.S. Application Data

(60) Provisional application No. 61/113,172, filed on Nov. 10, 2008.

(51) Int. Cl.
*A61K 31/397*     (2006.01)
*C07D 211/58*    (2006.01)
(Continued)

(52) U.S. Cl.
CPC .......... *C07D 211/58* (2013.01); *C07D 205/04* (2013.01); *C07D 207/09* (2013.01);
(Continued)

(58) Field of Classification Search
CPC .................... A61K 31/397; C07D 211/58
(Continued)

(56) References Cited

U.S. PATENT DOCUMENTS 9,403,763 B2    8/2016  Sodroski
2005/0020645 A1*  1/2005  Ohta ................... C07D 513/04
                                                         514/357
(Continued)

FOREIGN PATENT DOCUMENTS

EP           1127883 A2 *  8/2001  ............. A61K 31/00
JP      2002-106023 A     10/2003
(Continued)

OTHER PUBLICATIONS

Chen et al. European Journal of Pharmacology, (2007), vol. 565(1-3), p. 54-59.*
Chen et al., "Structure-based identification of small molecule compounds targeting cell cyclophilin A with anti-HIV-1 activity", European Journal of Pharmacology, vol. 565(1-3), pp. 54-59 (2007).
U.S. Appl. No. 15/117,866, Sodroski et al.
Andreadis et al., "Toward a More Accurate Quantitation of the Activity of Recombinant Retroviruses: Alternatives to Titer and Multiplicity of Infection", J. Virol., Feb. 2000, 74, 3431-3439.
Babcock et al., "Ligand Binding Characteristics of CXCR4 Incorporated into Paramagnetic Proteoliposomes", J. Biol. Chem., Oct. 2001, 276, 38433-38440.
Chan et al., "HIV entry and Its Inhibition", Cell, May 1998, 93, 681-684.
(Continued)

*Primary Examiner* — Yong Chu
(74) *Attorney, Agent, or Firm* — Baker & Hostetler LLP

(57) ABSTRACT

The invention provides for compounds of formula I: wherein Z is absent or $(CR_AR_B)_nW$; each RA and RB is independently (i) H, alkyl, alkenyl, alkynyl, cycloalkyl, heterocycloalkyl, aryl, heteroaryl, aralkyl, heteroaralkyl, haloalkyl, each of which may be optionally substituted; (ii) OH, ORc, NH2, NHR$_c$, NR$_c$R$_c$, SH, S(O)$_m$R$_c$; or (iii) R$_A$ and R$_B$ together form C(O); W is absent, C(O), C(O)O, C(O)NR$_c$R$_c$, O, S(O)$_m$, or NR$_c$R$_c$; Y is an optionally substituted heterocyclic, optionally substituted heteroaryl, optionally substituted cycloalkyl, optionally substituted aryl, or NR$_X$R$_Y$; wherein R$_x$ and R$_y$ are each independently H, alkyl or aryl; X$^1$ is selected from the group consisting of halogen, methyl, and hydroxyl; X2 is a halogen; each R$_c$ is independently alkyl, cycloalkyl, heterocycloalkyl, aryl, heteroaryl, aralkyl, or heteroaralkyl, each of which may be optionally substituted; m is 0, 1, or 2; and n is 1, 2, 3, 4, 5, or 6; and pharmaceutically acceptable salts thereof.

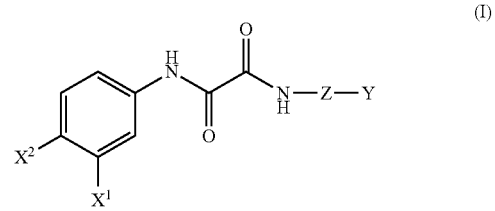

(I)

8 Claims, 40 Drawing Sheets

Figure 1A:
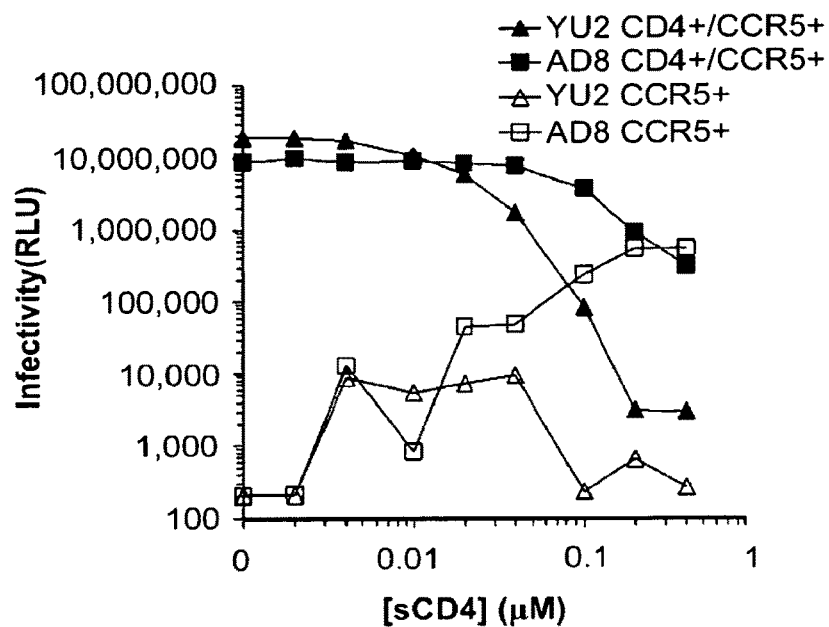
Figure 1B:
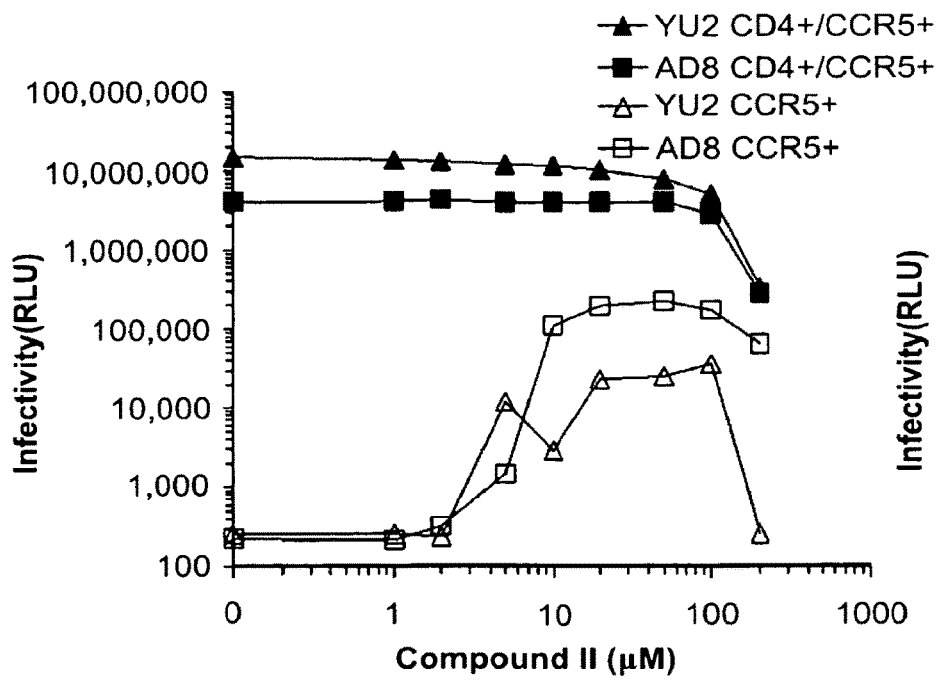
Figure 1C:
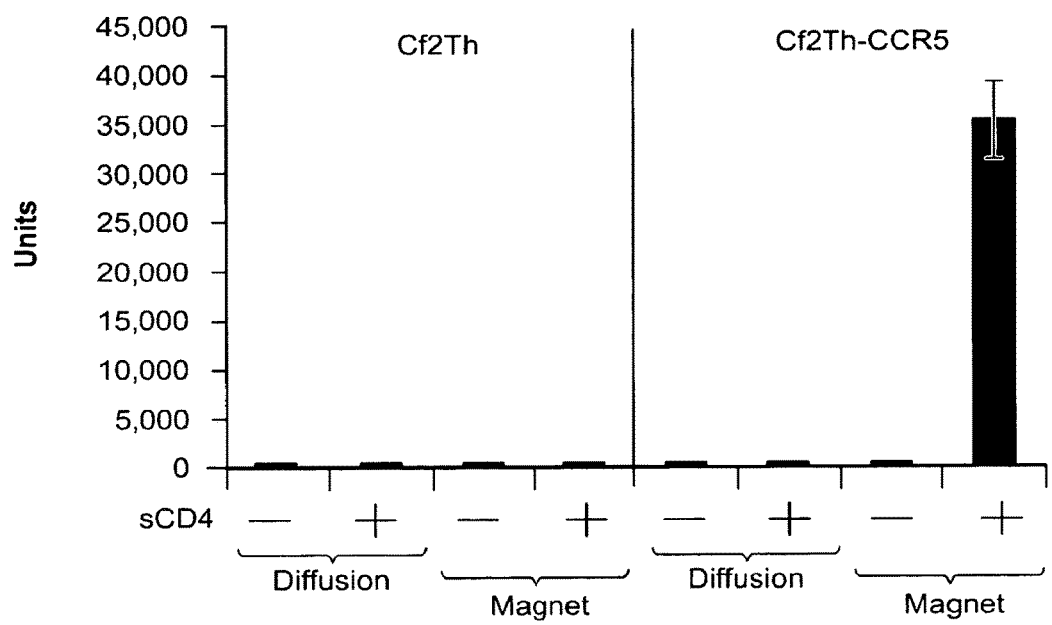

(51) Int. Cl.

| | | |
|---|---|---|
| C07D 205/04 | (2006.01) | |
| C07D 207/09 | (2006.01) | |
| C07D 207/16 | (2006.01) | |
| C07D 207/22 | (2006.01) | |
| C07D 211/26 | (2006.01) | |
| C07D 211/44 | (2006.01) | |
| C07D 211/56 | (2006.01) | |
| C07D 217/14 | (2006.01) | |
| C07D 223/04 | (2006.01) | |
| C07D 231/56 | (2006.01) | |
| C07D 233/64 | (2006.01) | |
| C07D 235/02 | (2006.01) | |
| C07D 235/14 | (2006.01) | |
| C07D 237/32 | (2006.01) | |
| C07D 239/42 | (2006.01) | |
| C07D 239/47 | (2006.01) | |
| C07D 239/90 | (2006.01) | |
| C07D 249/08 | (2006.01) | |
| C07D 265/36 | (2006.01) | |
| C07D 295/13 | (2006.01) | |
| C07D 307/52 | (2006.01) | |
| C07D 317/28 | (2006.01) | |
| C07D 333/20 | (2006.01) | |
| C07D 333/48 | (2006.01) | |
| C07D 401/04 | (2006.01) | |
| C07D 401/06 | (2006.01) | |
| C07D 405/06 | (2006.01) | |
| C07D 409/14 | (2006.01) | |
| C07D 455/02 | (2006.01) | |
| C07D 471/08 | (2006.01) | |
| C07D 473/18 | (2006.01) | |
| C07D 487/04 | (2006.01) | |
| C07D 495/04 | (2006.01) | |

(52) U.S. Cl.
CPC ......... *C07D 207/16* (2013.01); *C07D 207/22* (2013.01); *C07D 211/26* (2013.01); *C07D 211/44* (2013.01); *C07D 211/56* (2013.01); *C07D 217/14* (2013.01); *C07D 223/04* (2013.01); *C07D 231/56* (2013.01); *C07D 233/64* (2013.01); *C07D 235/02* (2013.01); *C07D 235/14* (2013.01); *C07D 237/32* (2013.01); *C07D 239/42* (2013.01); *C07D 239/47* (2013.01); *C07D 239/90* (2013.01); *C07D 249/08* (2013.01); *C07D 265/36* (2013.01); *C07D 295/13* (2013.01); *C07D 307/52* (2013.01); *C07D 317/28* (2013.01); *C07D 333/20* (2013.01); *C07D 333/48* (2013.01); *C07D 401/04* (2013.01); *C07D 401/06* (2013.01); *C07D 405/06* (2013.01); *C07D 409/14* (2013.01); *C07D 455/02* (2013.01); *C07D 471/08* (2013.01); *C07D 473/18* (2013.01); *C07D 487/04* (2013.01); *C07D 495/04* (2013.01)

(58) Field of Classification Search
USPC .............................................. 514/183, 210.15
See application file for complete search history.

(56) References Cited

U.S. PATENT DOCUMENTS

| | | |
|---|---|---|
| 2007/0021450 A1 | 1/2007 | Sklarz et al. |
| 2012/0122834 A1 | 5/2012 | Sodroski et al. |
| 2014/0377219 A1 | 12/2014 | Debnath et al. |

FOREIGN PATENT DOCUMENTS

| | | | |
|---|---|---|---|
| JP | | 2003-300875 A | 10/2003 |
| JP | | 2003300875 A | * 10/2003 |
| WO | WO 94/22826 A1 | | 10/1994 |
| WO | WO 97/02027 A1 | | 1/1997 |
| WO | WO 98/28268 A2 | | 7/1998 |
| WO | WO 98/55447 A1 | | 12/1998 |
| WO | WO 99/24065 A1 | | 5/1999 |
| WO | | 03000657 A1 | 1/2003 |
| WO | WO 2004/082687 A1 | | 9/2004 |
| WO | WO 2005/032490 A2 | | 4/2005 |
| WO | WO 2006/020070 A2 | | 2/2006 |
| WO | | 2006106963 A1 | 10/2006 |
| WO | WO 2010/053583 A2 | | 5/2010 |
| WO | WO 2011/109237 A2 | | 9/2011 |
| WO | WO 2013/090696 A1 | | 6/2013 |
| WO | WO 2015/120440 A2 | | 8/2015 |
| WO | WO 2016/025681 A1 | | 2/2016 |

OTHER PUBLICATIONS

Chan et al., "Evidence that a prominent cavity in the coiled coil of HIV type 1 gp41 is an attractive drug target", Proc. Natl. Sci., Dec. 1998, 95, 15613-15617.
Cheng et al., "Pharmaceutical applications of dendrimers: promising nanocarriers for drug delivery", Front. Biosci., Jan. 1, 2008, 13, 1447-1471.
Choe et al., "Tyrosine Sulfation of Human Antibodies Contributes to Recognition of the CCR5 Binding Region of HIV-1 gp120", Cell, Jul. 2003, 114, 161-170.
Clapham et al., "Human Immunodeficiency Virus Type 2 Infection and Fusion of CD4-Negative Human Cell Lines: Induction and Enhancement by Soluble CD4", J. Virol., Jun. 1992, 66, 3531-3537.
Courter, et al., "Structure-Based Design, Synthesis and Validations of CD4-Mimetic Small Molecule Inhibitors of HIV-1 Entry: Conversion of a Viral Entry Agonist to an Antagonist", Accounts of Chemical Research, Feb. 6, 2014, 47: 1228-1237.
Dimitrov et al., "Quantitation of Human Immunodeficiency Virus Type 1 Infection Kinetics", J. Virol., Apr. 1993, 67, 2182-2190.
Donzella et al., "AMD3100, a small molecule inhibitor of HIV-1 entry via the CXCR4 co-receptor", Nat. Med., Jan. 1998, 4, 1, 72-77.
Dragic et al., "HIV-1 entry into CD4+ cells is mediated by the chemokine receptor CC-CKR-5", Nature, Jun. 1996, 381, 667-673.
Dragic et al., "A binding pocket for a small molecule inhibitor of HIV-1 entry within the transmembrane helices of CCR5", Proc. Natl. Acad. Sci., May 9, 2000, 97(10), 5639-5644.
Feng et al., "HIV-1 Entry Cofactor: Functional cDNA Cloning of a Seven-Transmembrane, G Protein-Coupled Receptor", Science, May 1996, 272, 872-877.
Fisher et al., "HIV infection is blocked in vitro by recombinant soluble CD4", Nature, Jan. 1988, 331, 76-78.
Friesner et al., "Glide: A New Approach for Rapid, Accurate Docking and Scoring. 1. Method and Assessment of Docking Accuracy", J. Med. Chem., Mar. 2004, 47, 1739-1749.
Haim et al., "Synchronized Infection of Cell Cultures by Magnetically Controlled Virus", J. Virol., Jan. 2005, 79, 622-625.
Haim et al., "Time Frames for Neutralization during the Human Immunodeficiency Virus Type 1 Entry Phase, as Monitored in Synchronously Infected Cell Cultures", J. Virol., Apr. 2007, 81, 3525-3534.
Haim et al., "Soluble CD4 and CD4-Mimetic Compounds Inhibit HIV-1 Infection by Induction of a Short-Lived Activated State", PLoS Pathogens, Apr. 2009, 5, e1000360, 13 pages.
Halford, "Aiming for HIV's Weak Spot", Chemical & Engineering News, At War with HIV, Attacking the Virus Where it's Vulnerable, Chemical & Engineering News, Sep. 1, 2014, 14-21.
Halgren et al., "Glide: A New Approach for Rapid, Accurate Docking and Scoring. 2. Enrichment Factors in Database Screening", J. Med. Chem., Mar. 2004, 1750-1759.
Halgren, "MMFF VI. MMFF94s Option for Energy Minimization Studies", J. Comput. Chem., 1999, 20, 720-729.

(56) References Cited

OTHER PUBLICATIONS

Halgren, "MMFF VII. Characterization of MMFF94, MMFF94s, and Other Widely Available Force Fields for Conformational Energies and for Intermolecular-Interaction Energies and Geometries", J. Comput. Chem., 1999, 20, 730-748.

Heegaard et al., "Dendrimer Based Anti-Infective and Anti-Inflammatory Drugs", Recent Patents Anti-Infect. Drug Disc., Nov. 1, 2006, 1, 333-351.

Huang et al., "Scorpion-Toxin Mimics of CD4 in Complex with Human Immunodeficiency Virus gp120: Crystal Structures, Molecular Mimicry, and Neutralization Breadth", Structure, May 2005, 13, 755-768.

International Patent Application No. PCT/US12/60708: International Search Report dated Jan. 24, 2013, 4 pages.

Jones et al., "Development and Validation of a Genetic Algorithm for Flexible Docking", J. Mol. Biol., Aug. 1997, 267, 727-748.

Jorgensen et al., "Development and Testing of the OPLS All-Atom Force Field on Conformational Energetics and Properties of Organic Liquids", J. Am. Chem. Soc., Nov. 1996, 117, 11225-11236.

Karlsson et al., "The Envelope Glycoprotein Ectodomains Determine the Efficiency of CD4+ T Lymphocyte Depletion in Simian-Human Immunodeficiency Virus-Infected Macaques", J. Exp. Med., Sep. 1998, 188, 1159-1171.

Kassa, et al., "Transitions to and from the CD4-Bound Conformation are Modulated by a Single-Residue Change in the Human Immunodeficiency Virus Type 1 gp120 Inner Domain", J. Viral., Sep. 2009, 83(17), 8364-8378.

Korber et al., "Numbering Positions in HIV Relative to HXB2CG", Hum. Retroviruses AIDS III, Dec. 1998, 102-111.

Kunkel et al., "Rapid and Efficient Site-Specific Mutagenesis without Phenotypic Selection", Meth. Enzymol., 1987, 154, 367-382.

Kuntz et al., "Structure-Based Molecular Design", Accounts Chem. Res., May 1994, 27, 117-123.

Kwon, et al., "Crystal Structures of HIV-1 gp120 Envelope Glycoprotein in Complex with NBD Analogues that Target the CD4-Binding Site", PLOS One, Jan. 28, 2014, 9(1), 12 pgs.

Kwong et al., "Structure of an HIV gp120 envelope glycoprotein in complex with the CD4 receptor and a neutralizing human antibody", Nature, Jun. 1998, 393, 648-659.

Kwong et al., "Structures of HIV gp120 envelope glycoproteins from laboratory-adapted and primary isolates", Structure, Dec. 2000, 8, 1329-1339.

LaLonde et al., "Design, synthesis and biological evaluation of small molecule inhibitors of CD4-gp120 binding based on virtual screening", Bioorganic & Medicinal Chemistry, Jan. 2011, 19, 91-101.

LaLonde et al., "Structure-Based Design, Synthesis, and Characterization of Dual Hotspot Small-Molecule HIV-1 Entry Inhibitors", Journal of Medicinal Chemistry, May 2012, 55, 4382-4396.

Lalonde, et al., "Structure-Based Design and Synthesis of an HIV-1 Entry Inhibitor Exploiting X-Ray and Thermodynamic Characterization", ACS Med. Chem. Letter, Mar. 14, 2013, 4(3), 338-343.

Lin et al., "A small molecule HIV-1 inhibitor that targets the HIV-1 envelope and inhibits CD4 receptor binding", Proc. Natl. Acad. Sci., Sep. 2003, 100, 11013-11018.

Lovell et al., "Structure Validation by Cα Geometry: φ, ψ and Cβ Deviation", Proteins: Structure, Function and Genetics, Jan. 2003, 50, 285, 437-450.

Luque et al., "Structure-based prediction of binding affinities and molecular design of peptide ligands", Methods Enzymol, 1998, 295, 100-127.

Luty et al., "A Molecular Mechanics / Grid Method for Evaluation of Ligand-Receptor Interactions", J. Comp. Chem., 1995, 16, 454-464.

Madani et al., "Inhibition of Human Immunodeficiency Virus Envelope Glycoprotein-Mediated Single Cell Lysis by Low-Molecular-Weight Antagonists of Viral Entry", J. Virol., Jan. 2007, 81, 532-538.

Madani, et al., "CD4-Minetic Small Molecules Sensitize Human Immunodeficiency Virus to Vaccine-Elicited Antibodies", Journal of Virology, Jun. 2014, 88(12):6542-6555.

Madani, et al., "Small-Molecule CD4 Mimics Interact with a Highly Conserved Pocket on HIV-1 gp120", Structure, Nov. 12, 2008, 16(11), 1689-1701.

Martin et al., "Rational design of a CD4 mimic that inhibits HIV-1 entry and exposes cryptic neutralization epitopes", Nat. Biotechnol., Jan. 2003, 21, 71-76.

Munro, et al., "Conformational Dynamics of Single HIV-1 Envelope Trimers on the Surface of Native Virions", Science, Nov. 7, 2014, 46(6210), 759-763.

Myszka et al., "Energetics of the HIV gp120-CD4 binding reaction", Proc. Natl. Acad. Sci., Aug. 2000, 97, 9026-9031.

Olshevsky et al., "Identification of Individual Human Immunodeficiency Virus Type 1 gp120 Amino Acids Important for CD4 Receptor Binding", J. Virol., Dec. 1990, 64, 5701-5707.

Orloff et al., "Two Mechanisms of Soluble CD4 (sCD4)-Mediated Inhibition of Human Immunodeficiency Virus Type 1 (HIV-1) Infectivity and Their Relation to Primary HIV-1 Isolates with Reduced Sensitivity to sCD4", J. Virol., Mar. 1993, 67, 1461-1471.

Rho et al., "Characterization of the Reverse Transcriptase from a New Retrovirus (HTLV) Produced by a Human Cutaneous T-Cell Lymphoma Cell Line", Virology, Jul. 1981, 112, 355-360.

Richard, et al., "CD4 Mimetics Sensitize HIV-1-Infected Cells to ADCC", PNAS, May 4, 2015, 112(20): E2687-E2694.

Robertson et al., "Protein Structure and the Energetics of Protein Stability", Chem. Rev., May 1997, 97, 1251-1268.

Rupp et al., "ViraGel™ (SPL7013 Gel): A candidate dendrimer—microbicide for the prevention of HIV and HSV infection", Int. J. Nanomedicine, 2007, 2(4), 561-566.

Schenten et al., "Effects of Soluble CD4 on Simian Immunodeficiency Virus Infection of CD4-Positive and CD4-Negative Cells", J. Virol., Jul. 1999, 73, 5373-5380.

Schon et al., "Thermodynamics of binding of a low-molecular-weight CD4 mimetic to HIV gp120", Biochemistry, Sep. 2006, 45, 10973-10980.

Si et al., "Small-molecule inhibitors of HIV-1 entry block receptor-induced conformational changes in the viral envelope glycoproteins", Proc. Natl. Acad. Sci., Apr. 2004, 101, 5036-5041.

Staudinger et al., "Evidence for CD4-enhanced Signaling through the Chemokine Receptor CCR5", J. Biol. Chem., Mar. 2003, 278, 10389-10392.

Stouten et al., "An Effective Solvation Term Based on Atomic Occupancies for Use in Protein Simulations", C Molecular Stimulation, Jan. 1993, 10(2-6), 97-120.

Strizki et al., "SCH-C (SCH 351125), an orally bioavailable, small molecule antagonist of the chemokine receptor CCR5, is a potent inhibitor of HIV-1 infection in vitro and in vivo", Proc. Natl. Acad. Sci., Oct. 23, 2001, 98(22), 12718-12723.

Sullivan et al., "Determinants of Human Immunodeficiency Virus Type 1 Envelope Glycoprotein Activation by Soluble CD4 and Monoclonal Antibodies", J. Virol., Aug. 1998, 72, 6332-6338.

Tagat et al., "Piperazine-Based CCR5 Antagonists as HIV-1 Inhibitors. IV. Discovery of 1-[4,6-Dimethyl-5-pyrimidinyl)carbonyl]-4[4-{2-methoxy-1(R)-4-(trifluoromethyl)-phenyl}ethyl-3(S)-methyl-1-piperazinyl]-4-methylpiperdine (Sch-417690/Sch-D), a Potent, Highly Selective, and Orally Bioavailable CCR5 Antagonist", J. Med. Chem., May 6, 2004, 47(10, 2405-2408.

Thali et al., "Characterization of a Discontinuous Human Immunodeficiency Virus Type 1 gp120 Epitope Recognized by a Broadly Reactive Neutralizing Human Monoclonal Antibody", J. Virol., Nov. 1991, 65, 6188-6193.

Trikola et al., "CD4-dependent, antibody-sensitive interactions between HIV-1 and its co-receptor CCR-5", Nature, Nov. 1996, 384, 184-187.

Vita et al., "Rational engineering of a miniprotein that reproduces the core of the CD4 site interacting with HIV-1 envelope glycoprotein", Natl. Acad. Sci., Nov. 1999, 96, 13091-13096.

Weissenhorn et al., "Atomic structure of the ectodomain from HIV-1 gp41", Nature, May 1997, 387, 426-430.

(56) References Cited

OTHER PUBLICATIONS

Word et al., "Visualizing and Quantifying Molecular Goodness-of-Fit: Small-probe Contact Dots with Explicit Hydrogen Atoms", J. Mol. Biol., Jan. 1999, 285, 1711-1733.

Wu et al., "CD4-induced interaction of primary HIV-1 gp120 glycoproteins with the chemokine receptor-5", Nature, Nov. 1996, 384, 179-183.

Wyatt et al., "The HIV-1 Envelope Glycoproteins: Fusogens, Antigens, and Immunogens", Science, Jun. 1998, 280, 1884-1888.

Wyss et al., "The Highly Conserved C-Terminal Dileucine Motif in the Cytosolic Domain of the Human Immunodeficiency Virus Type 1 Envelope Glycoprotein Is Critical for Its Association with the AP-1 Clathrin Adapter", J. Viral., Mar. 2001, 75, 2982-2992.

Xiang et al., "Functional Mimicry of a Human Immunodeficiency Virus Type 1 Coreceptor by a Neutralizing Monoclonal Antibody", J. Virol., May 2005, 79, 6068-6077.

Xiang et al., "Mutagenic stabilization and/or disruption of a CD4-bound state reveals distinct conformations of the human immunodeficiency virus type 1 gp120 envelope glycoprotein", J. Virol., Oct. 2002, 76, 9888-9899.

Xie, et al., "Structure-Activity Relationships in the Binding of Chemically Derivatized CD4 to gp120 from Human Immunodeficiency Virus", J. Med. Chem., Oct. 4, 2007, 50(20), 4898-4908.

Zhang et al., "Antibody 17b Binding at the Coreceptor Site Weakens the Kinetics of the Interaction of Envelope Glycoprotein gp120 with CD4", Biochemistry, Feb. 2001, 40, 1662-1670.

Zhang et al., "Expression, Purification, and Characterization of Recombinant HIV gp120", J. Biol. Chem., Oct. 2001, 276, 39577-39585.

Zhang et al., "Conformational changes of gp120 in epitopes near the CCR5 binding site are. induced by CD4 and a CD4 miniprotein mimetic", Biochemistry, May 1999, 38, 9405-9416.

\* cited by examiner

FIG. 7A

| R group | NBD-556 | II | V | XIII | XIV | XV |
|---|---|---|---|---|---|---|
| | (4-Cl) | (4-Cl, 3-F) | (4-Cl, 3-Cl) | (4-Cl, 3-OH) | (4-Cl, 3-CH₃) | (4-Cl, 3-CF₃) |
| Name | NBD-556 | II | V | XIII | XIV | XV |
| $K_d$ (μM) | 3.7 | 0.76 | 1.3 | >8 | 5.2 | weak |
| ΔG (kcal/mol) | -7.4 | -8.3 | -8.0 | | -7.2 | |
| ΔH (kcal/mol) | -24.5 | -20.8 | -14.1 | | -19.9 | |
| -TΔS (kcal/mol) | +17.1 | +12.5 | +6.1 | | +12.7 | |
| CCR5 binding | 1.0±0 | 2.1 | 0.6 | 0 | 0.2 | 0 |
| Enhancement of viral infection of CD4⁻ cells (μM) | 1.0±0 | 1.9±0.2 | 0.02±0.01 | 0.001±0.003 | 0.1±0.04 | 0.03±0.06 |
| IC₅₀ of HIV-1 on CD4+cells (μM) | >100 | 54.4 | 13.6 | >100 | 25.2 | 66.4 |
| IC₅₀ of A-MLV on CD4+cells (μM) | >100 | >100 | 6.1 | >100 | 21.9 | 44.7 |

FIG. 10

| | Compounds | |
|---|---|---|
| II | Name | NBD-556 |
| 0.76 | $K_d$ (μM) | 3.7 |
| -8.3 | ΔG (kcal/mol) | -7.4 |
| -20.8 | ΔH (kcal/mol) | -24.5 |
| +12.5 | -TΔS (kcal/mol) | +17.1 |
| 1.0 (n=10) | Enhancement of viral infection of $CD4^-$ cells | 0.7 +/- 0.1 (n=8) |
| 55.2 +/- 6.8 (n=10) | $IC_{50}$ of HIV-1 on $CD4^+$ cells (μM) | 73.7 +/- 9.9 (n=7) |
| >100 (n=10) | $IC_{50}$ of A-MLV on $CD4^+$ cells (μM) | >97 (n=7) |

| III | XVI |
|---|---|
| 0.33 | 2.1 |
| -8.8 | -7.7 |
| -19.7 | -13.7 |
| +10.9 | +6 |
| 2.1 +/- 0.4 (n=8) | 0.5 +/- 0.2 (n=4) |
| 48.7 +/- 7.7 (n=9) | 33.3 +/- 11.6 (n=4) |
| >98 (n=9) | >100$\mu$M (n=4) |

FIG. 14

| R group | NBD-556 (Cl) | NBD-557 (Br) | VIII (I) |
|---|---|---|---|
| Name | | | |
| YU2 w.t. | 1.0 ± 0.2 | 1.8 ± 0.3 | 0.4 ± 0.1 |
| V255A | 0 | 0 | 0 |
| T257A | 0 | 0.07 ± 0.01 | 0.1 ± 0.06 |
| T257S | 0 | 0 | 0.07 ± 0.03 |
| D368A | 1.9 ± 0.2 | 0.04 ± 0.004 | 0.1 ± 0.03 |
| S375A | 2.9 ± 0.1 | 1.2 ± 0.1 | 2.8 ± 0.3 |
| S375G | 0.1 ± 0.10 | 0.14 ± 0.04 | 0.0004 ± 0.001 |
| S375W | 0.01 ± 0.007 | 0.04 ± 0.02 | 0.1 ± 0.8 |
| E429A | 0.8 ± 0.1 | 0.09 ± 0.007 | 0.07 ± 0.02 |
| E429K | 0.1 ± 0.05 | 0.2 ± 0.009 | 0 |
| V430A | 0.02 ± 0.002 | 0.5 ± 0.01 | 0 |
| V430S | 0.01 ± 0.002 | 0.2 ± 0.005 | 0 |
| D368A/V430A | 2.2 ± 0.4 | 2.3 ± 0.4 | 0.2 ± 0.1 |
| D368A/V430S | 0.6 ± 0.04 | 0.6 ± 0.1 | 0 |
| A-MLV | 0.003 ± 0.001 | 0 | 0 |

|  | IC$_{50}$μM | K$_d$μM | Viral Infectivity |
|---|---|---|---|
|  | 75.8 +/- 15.6 | 3.3 | 0.48 +/- 0.21 |
|  | 50.5 +/- 49.6 | N.D. | 0.0 |
|  | > 100 | 4.2 | 0.68 +/- 0.25 |
|  | > 100 | 2.5 | 0.30 |
|  | > 100 | N.D. | 0.1 |
|  | > 100<br>.5 +/- 0.2 | 2.3 | 0.0 |
|  | 85.2 +/- 14.8 | 2.1 | 0.05 +/- 0.04 |
|  | 64.5 Non-Specific | 4.0 | 0.06 |
|  | 75.5 +/- 23.8 | 1.6 | 0.24 +/- 0.19` |
|  | 68.3 +/- 9.6 | 3.1 | 2.80 +/- 2.65 |
|  | 23.4 Non-specific | | 0.0 |

|  | IC$_{50}$µM | K$_d$µM | Viral Infectivity |
|---|---|---|---|
|  | > 100 | | 0.0 |
|  | > 100 | | 0.0 |
|  | > 100 | | 0.0 |
|  | > 100 | | 0.0 |
|  | > 100 | | 0.0 |
|  | > 100 | | |
|  | > 100 | | 0.0 |
|  | > 100 | | 0.0 |
|  | > 100 | | 0.0 |
|  | 20.5 non-specific | | 0.5 |

|  | IC$_{50}$μM | K$_d$μM | Viral Infectivity |
|---|---|---|---|
|  | > 100 | | |
|  | > 100 | | 0.0 |
|  | > 100 | | 0.0 |
|  | > 100 | | 0.0 |
|  | 61.4 Non-specific | | 0.4 |
|  | | | 0.0 |
|  | 73.6 Non-specific | | 0.11 |
|  | 29.4 Non-specific | | 0.0 |
|  | > 100.0 | | |

Luc Assay

Figure 17A:
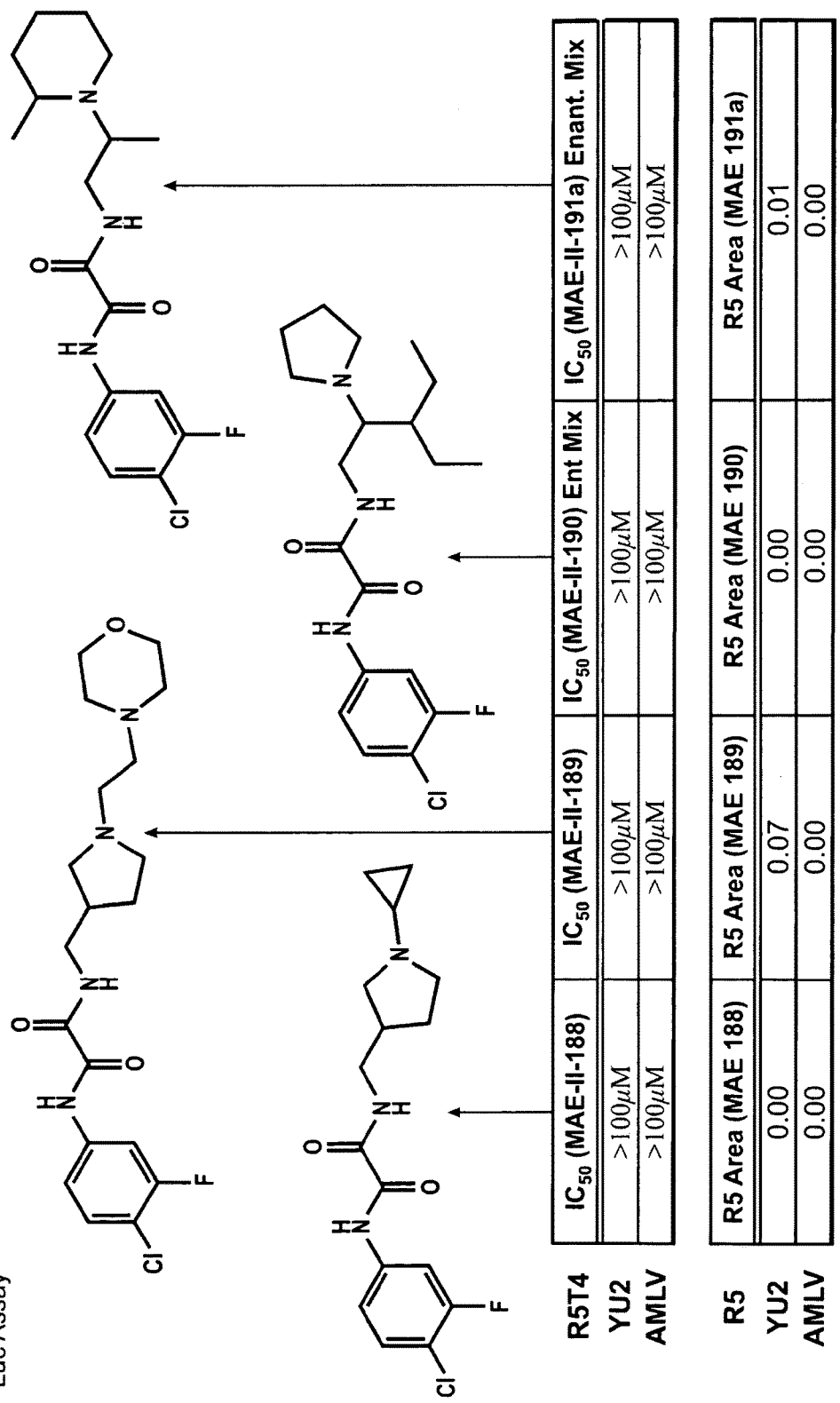
Figure 17A:
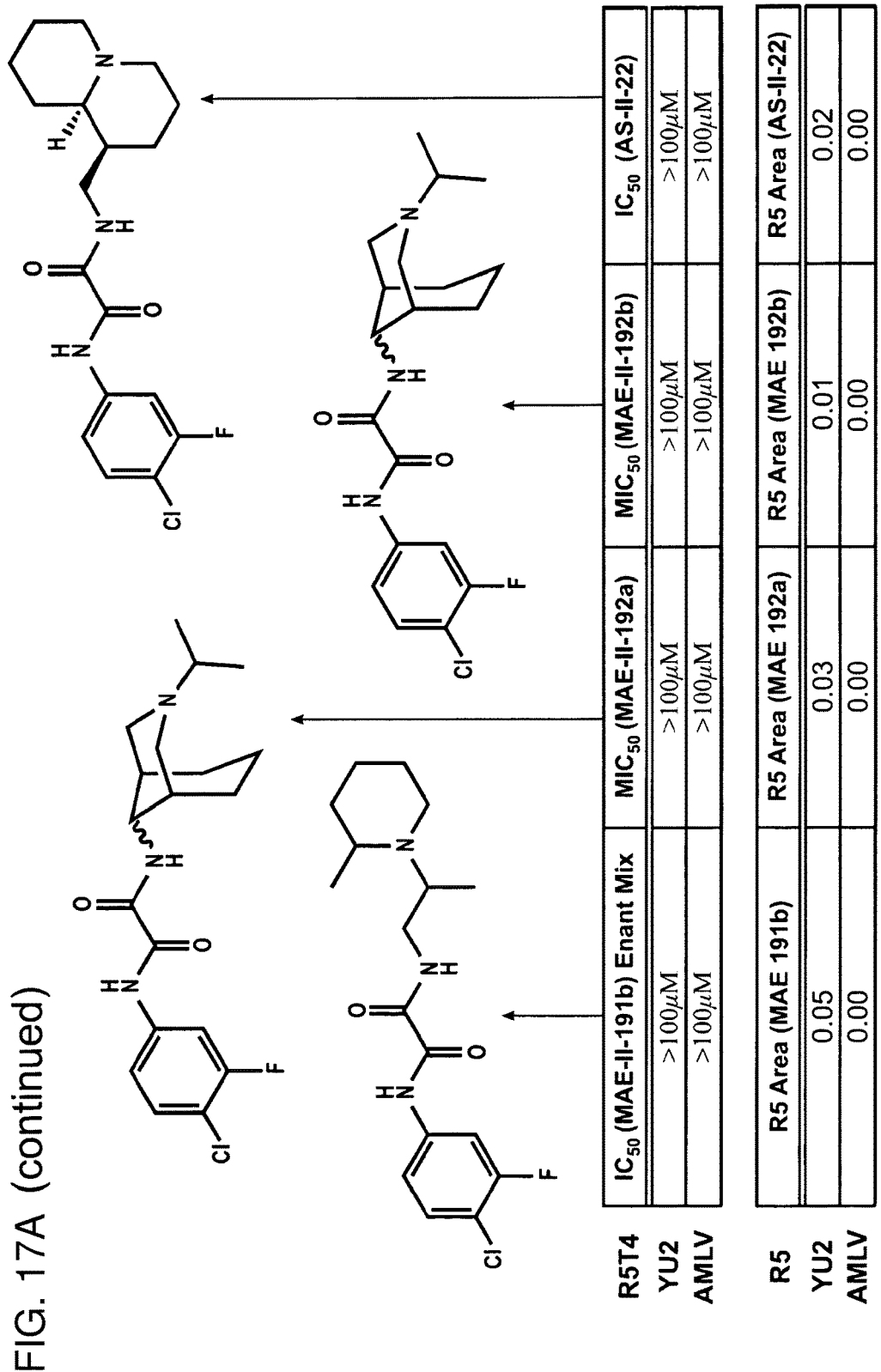
Figure 17A:
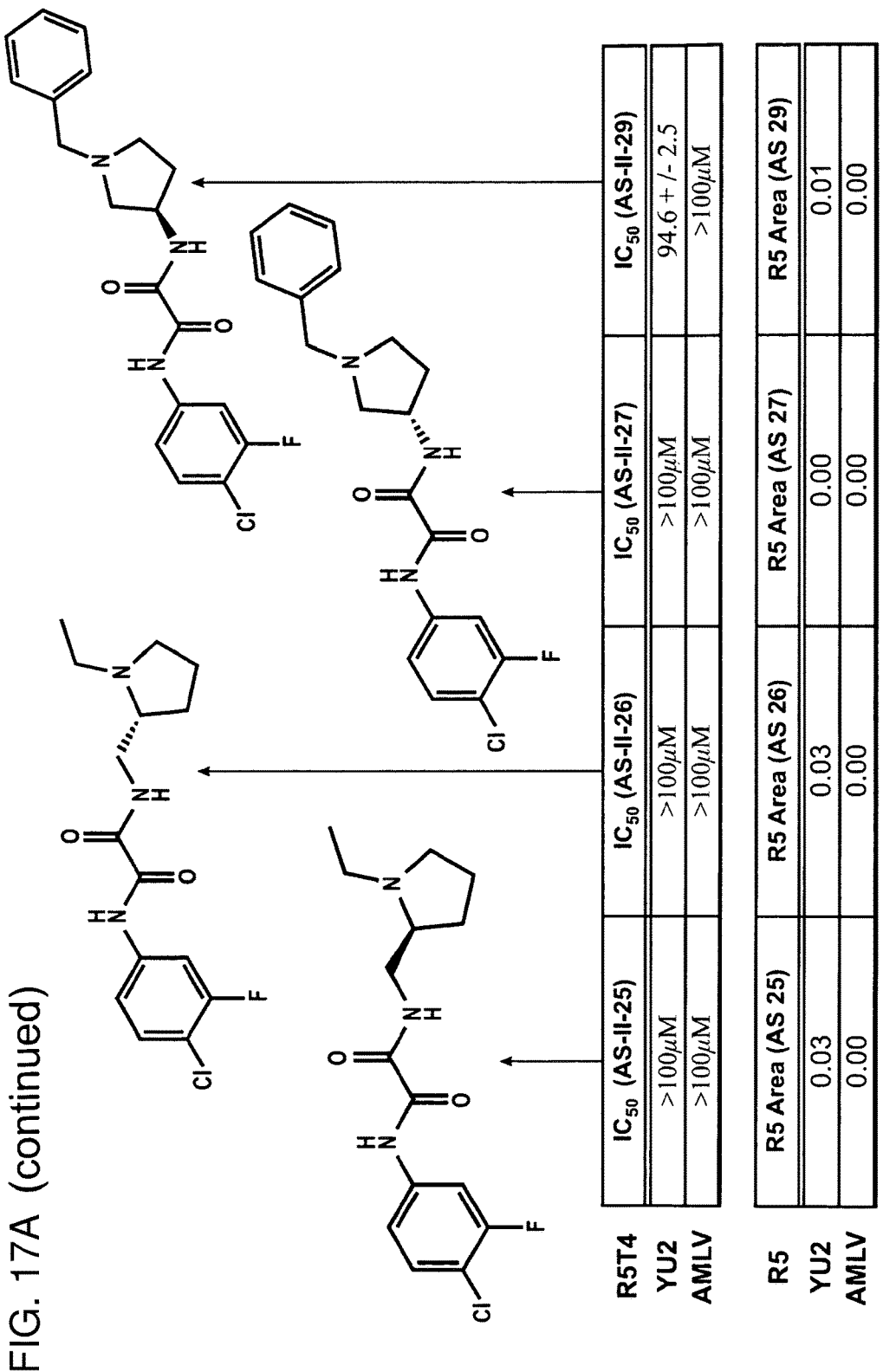
Figure 17A:
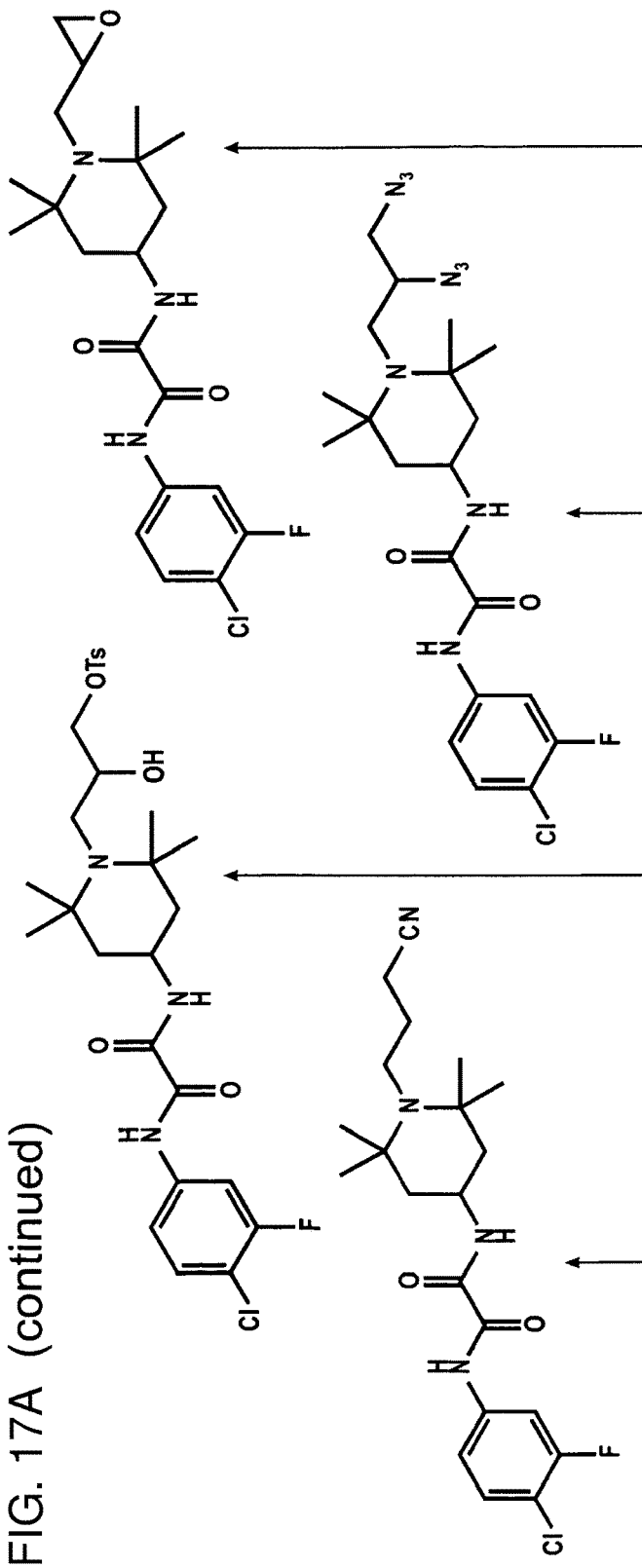
Figure 17A:
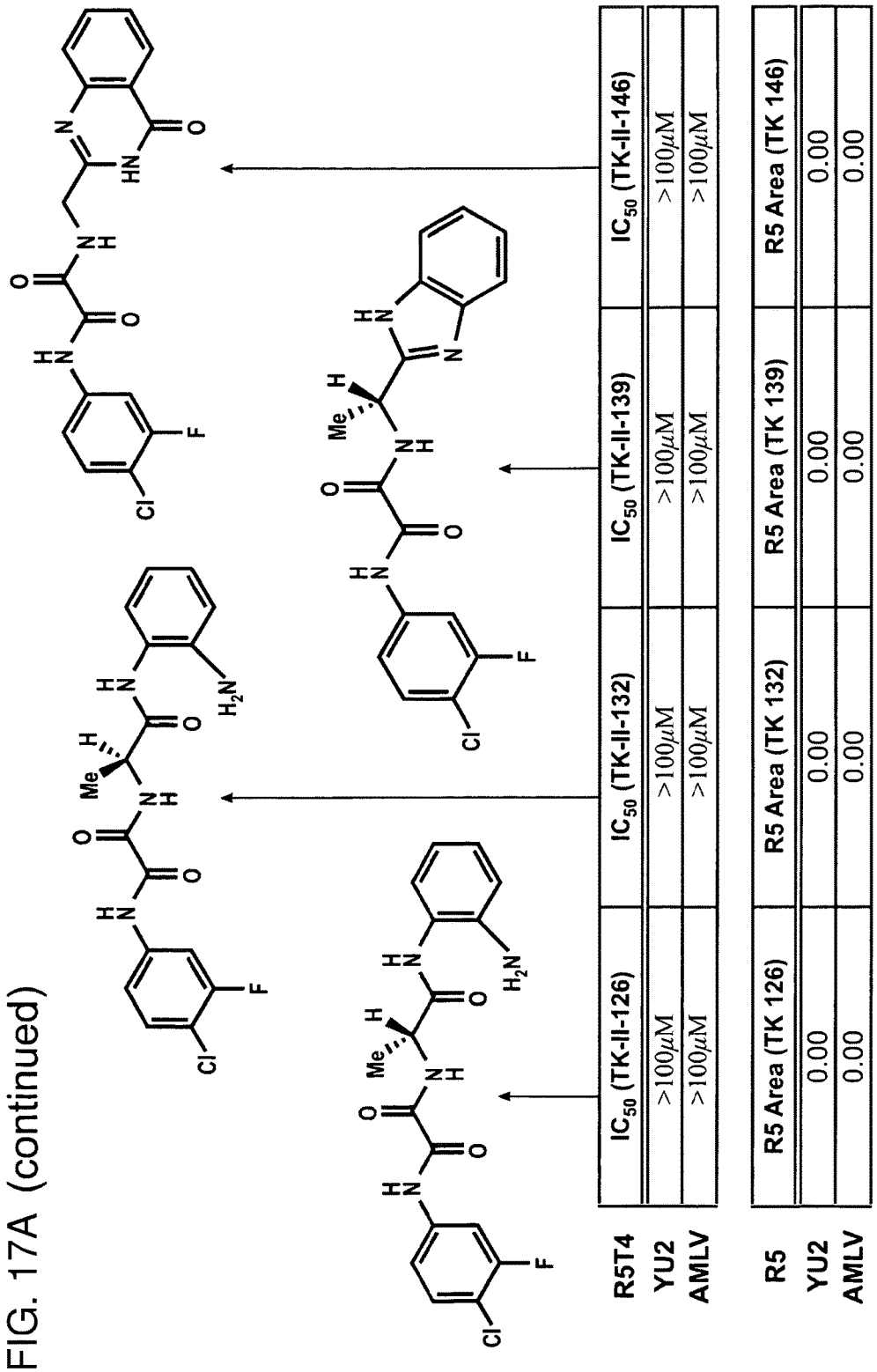
Figure 17A:
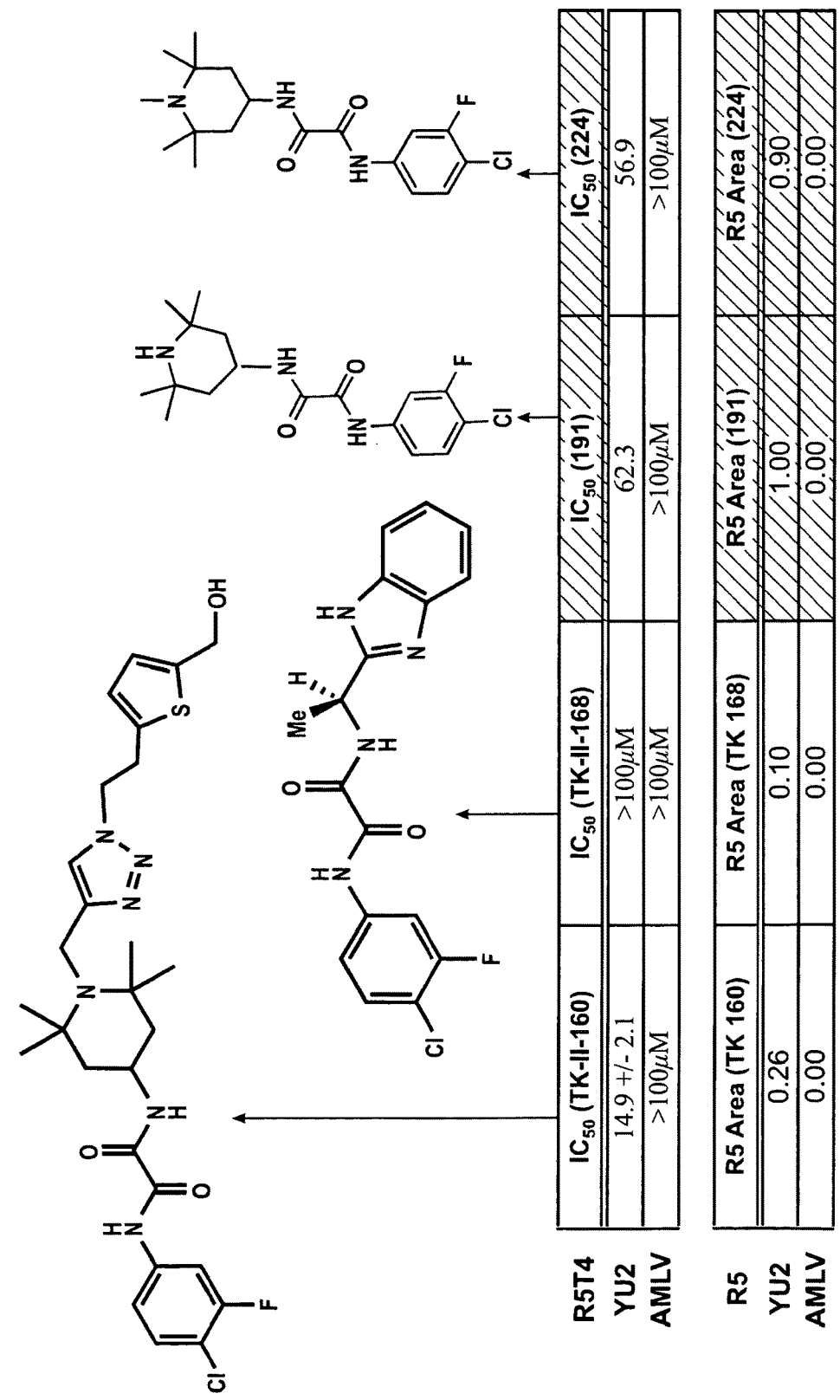

FIG. 17A (continued)

| IC$_{50}$ (AS-I-215) | | IC$_{50}$ (AS-I-227) | |
|---|---|---|---|
| R5T4 | | | |
| YU2 | >100μM | YU2 | >100μM |
| AMLV | >100μM | AMLV | >100μM |

| R5 Area (AS 215) | | R5 Area (AS 227) | |
|---|---|---|---|
| R5 | | | |
| YU2 | 0.17 | YU2 | 0.00 |
| AMLV | 0.00 | AMLV | 0.00 |

Luc Assay

| R5T4 | IC$_{50}$ (AS-I-261) | IC$_{50}$ (AS-II-23) | IC$_{50}$ (AS-II-28) | IC$_{50}$ (AS-II-34) | IC$_{50}$ (AS-II-36) |
|---|---|---|---|---|---|
| YU2 | 72.6 +/- 5.7 | 27.6 +/- 7.2 | 27.4 +/- 6.9 | 12.6 +/- 1.0 | 2.5 +/- 0.4 |
| AMLV | 94.4 | 91.3 | >100µM | 9.9 +/- 0.6 | 95.3 |

| R5 | R5 Area (AS-I-261) | R5 Area (AS-II-23) | R5 Area (AS-II-28) | R5 Area (AS-II-34) | R5 Area (AS-II-36) |
|---|---|---|---|---|---|
| YU2 | 1.49 | 0.03 | 0.10 | 0.04 | 0.31 |
| AMLV | 0.00 | 0.00 | 0.00 | 0.00 | 0.00 |

Figure 17B:
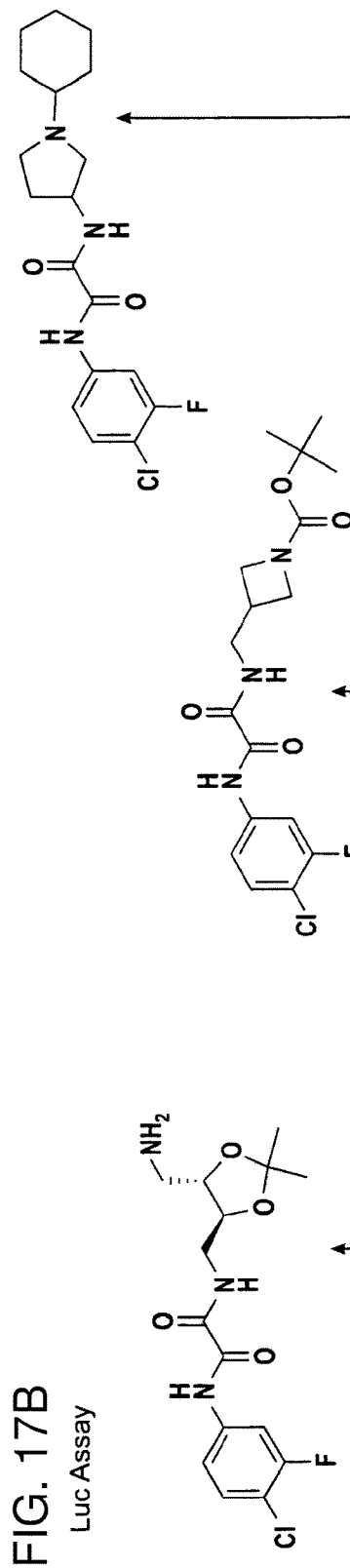

FIG. 17B (continued)

| | IC$_{50}$ (AS-II-37) | IC$_{50}$ (AS-II-41) | IC$_{50}$ (TK-II-52) | IC$_{50}$ (TK-II-103) |
|---|---|---|---|---|
| R5T4 | | | | |
| YU2 | 50.4 +/- 14.2 | >100μM | 76.2 | 22.7 +/- 12.0 |
| AMLV | >100μM | >100μM | 80.8 +/- 2.4 | 79.9 +/- 7.7 |

| | R5 Area (AS-II-37) | R5 Area (AS-II-41) | R5 Area (TK-II-52) | R5 Area (TK-II-103) |
|---|---|---|---|---|
| R5 | | | | |
| YU2 | 0.56 | 0.06 | 0.00 | 0.18 |
| AMLV | 0.00 | 0.00 | 0.00 | 0.00 |

FIG. 17B (continued)

| | IC$_{50}$ (TK-II-106) | IC$_{50}$ (TK-II-151) | IC$_{50}$ (191) | IC$_{50}$ (224) |
|---|---|---|---|---|
| R5T4 | | | | |
| YU2 | >100μM | >100μM | 74.8 +/- 5.1 | 15.4 +/- 2.7 |
| AMLV | >100μM | >100μM | >100μM | >100μM |

| | R5 Area (TK-II-106) | R5 Area (TK-II-151) | R5 Area (191) | R5 Area (224) |
|---|---|---|---|---|
| R5 | | | | |
| YU2 | 0.03 | 0.02 | 1.00 | 0.63 |
| AMLV | 0.00 | 0.00 | 0.00 | 0.00 |

SMALL MOLECULE CD4 MIMETICS AND USES THEREOF

CROSS-REFERENCE TO RELATED APPLICATIONS

This application is a 35 U.S.C. §371 U.S. national entry of International Application PCT/US2009/006049 (WO 2010/053583) having an International filing date of Nov. 10, 2009 which claims the benefit of U.S. Provisional Application 61/113,172, which was filed on Nov. 10, 2008. The entire contents of which are incorporated herein.

BACKGROUND OF THE INVENTION

This invention relates generally to human immunodeficiency virus (HIV) and, more specifically to compounds that are prophylactic against transmission of and/or effectively treat HIV infection.

Prevention of human immunodeficiency virus (HIV) transmission can be realized by approaches that interrupt the early phase of retrovirus infection, before provirus formation. One early event, HIV entry into target cells, involves the viral envelope glycoproteins, gp120 and gp41, and host cell receptors, CD4 and the chemokine receptors (either CCR5 or CXCR4). Binding to CD4 induces conformational changes in the exterior envelope glycoprotein gp120 that allow CCR5/CXCR4 engagement and that expose elements of the gp41 transmembrane glycoprotein. Further conformational changes in gp41 lead to fusion of the viral and host cell membranes, allowing virus entry. Each of these steps represents a potential target for intervention.

To evade host antibody responses, HIV has evolved envelope glycoproteins with surface variability, dense glycosylation and conformational flexibility. The unliganded HIV gp120 glycoprotein is unusually flexible and partially unstructured; binding CD4 locks gp120 into a rigid conformation. This binding event is characterized by an unusually large and favorable enthalpy change that is partially countered by a large unfavorable entropy change. High-resolution structures of CD4-bound HIV gp120 have provided insights into these conformational transitions. The conserved gp120 core consists of an inner domain that interacts with gp41, an outer domain with a heavily glycosylated surface, and a bridging sheet that connects these two domains. On the unliganded HIV gp120, the inner and outer gp120 domains are thought to move with respect to each other, with the bridging sheet assuming a conformation different from that seen in the CD4-bound state.

CD4 primarily contacts the gp120 outer domain and bridging sheet. CD4 binding creates a 153-Å cavity ("the Phe 43 cavity") at the interface between gp120 and CD4; the Phe 43 cavity is bounded by highly conserved residues from all three gp120 domains and by a single CD4 residue, Phe 43. The contacts made by phenylalanine 43 and arginine 59 of CD4 with gp120 residues in the vestibule of this virtual pocket contribute significantly to gp120-CD4 affinity. Thus, the Phe 43 cavity has been indicated as a desirable target for compounds that could disrupt gp120-CD4 interactions.

It would therefore be beneficial to develop compounds that are capable of targeting the Phe 43 pocket. The present invention satisfies this need and provides related advantages as well.

SUMMARY OF THE INVENTION

In one aspect, the invention provides a compound of formula I:

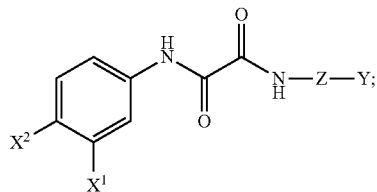

wherein

Z is absent or $(CR_AR_B)_nW$;

each $R_A$ and $R_B$ is independently (i) H, alkyl, alkenyl, alkynyl, cycloalkyl, heterocycloalkyl, aryl, heteroaryl, aralkyl, heteroaralkyl, haloalkyl, each of which may be optionally substituted; (ii) OH, $OR_C$, $NH_2$, $NHR_C$, $NR_CR_C$, SH, $S(O)_mR_C$; or (iii) $R_A$ and $R_B$ together form C(O);

W is absent, C(O), C(O)O, $C(O)NR_CR_C$, O, $S(O)_m$, or $NR_CR_C$;

Y is an optionally substituted heterocyclic, optionally substituted heteroaryl, optionally substituted cycloalkyl, optionally substituted aryl, or $NR_XR_Y$; wherein $R_X$ and $R_Y$ are each independently H, alkyl or aryl;

$X^1$ is selected from the group consisting of halogen, methyl, and hydroxyl;

$X^2$ is a halogen;

each $R_C$ is independently H, alkyl, cycloalkyl, heterocycloalkyl, aryl, heteroaryl, aralkyl, or heteroaralkyl, each of which may be optionally substituted;

m is 0, 1, or 2; and n is 1, 2, 3, 4, 5, or 6.

In one aspect, the invention provides a method of activating HIV exterior envelope glycoprotein gp120 comprising contacting HIV with an effective amount of a compound according to any of the formulae herein, to bind said gp120.

In another aspect, the invention provides a method of inhibiting transmission of HIV to a cell comprising contacting HIV with an effective amount of a compound according to any of the formulae herein to bind HIV exterior envelope glycoprotein gp120, thereby inhibiting transmission of HIV to said cell.

In various aspects, the invention provides a method of inhibiting the progression of HIV infection comprising contacting HIV with an effective amount of a compound according to any of the formulae herein to bind HIV exterior envelope glycoprotein gp120, thereby inhibiting progression of HIV.

In other aspects, the invention provides a method of inhibiting the transmission or progression of HIV to a cell comprising: contacting HIV with an effective amount of a compound according to any of the formulae herein to bind HIV exterior envelope glycoprotein gp120; and contacting HIV with an effective amount of an exogenous ligand that blocks binding to a chemokine receptor expressed on said cell.

BRIEF DESCRIPTION OF THE DRAWINGS

FIGS. 1*a-c* show the inhibition and activation of infection by sCD4 and the CD4-mimetic compound II. Recombinant HIV(YU2) or HIV(AD8) strains were incubated with $CD4^-CCR5^+$ or $CD4^+CCR5^+$ Cf2Th cells in the presence of sCD4 (FIG. 1*a*) or compound II (FIG. 1*b*). Infectivity was determined by measurement of luciferase activity. In FIG. 1*c* HIV(YU2) was incubated for three minutes in the presence or absence of sCD4 (40 μg/ml) and then adsorbed by diffusion or magnetically to cultures of the indicated cell type. Measured luciferase activity is presented as mean relative light units (RLU)±standard error of the mean (s.e.m.) of three replicate samples.

Figure 2A:
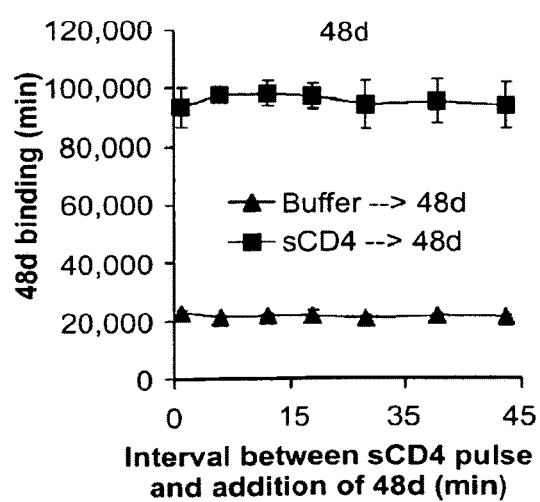
Figure 2B:
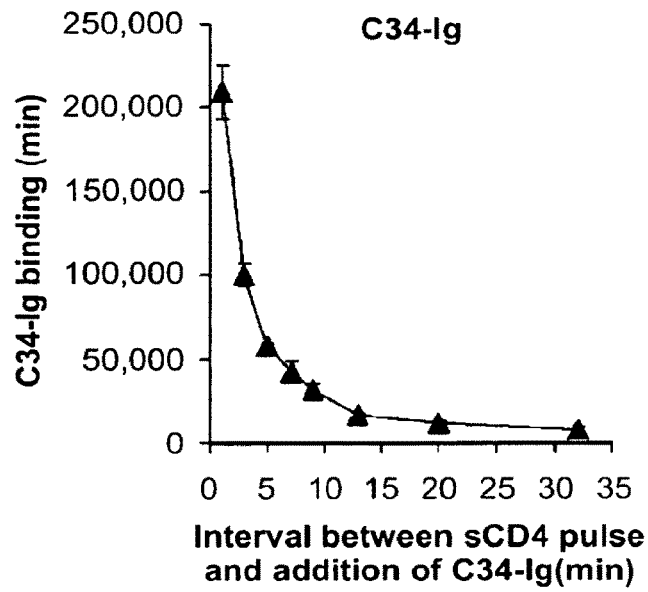
Figure 2C:
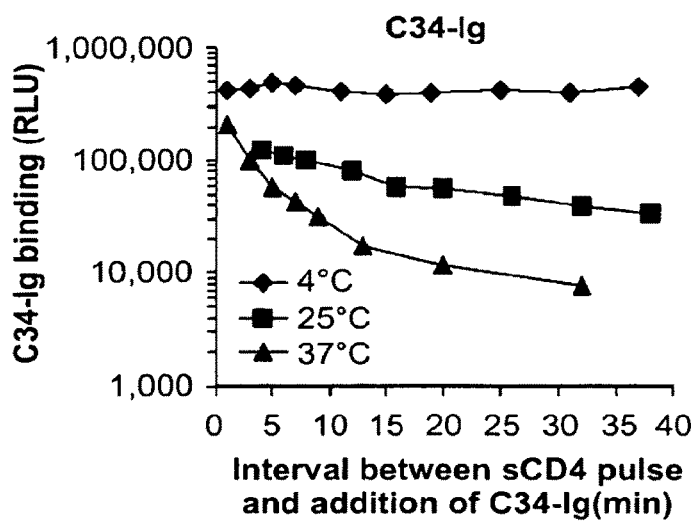

FIGS. 2a-c show the change over time in the exposure of CD4-induced epitopes. Cells that express the Env gps of HIVYU2 were pulsed for three minutes with sCD4 (40 μg/ml) and incubated for different time periods at 37° C. The monoclonal antibody 48d (a) or C34-Ig (b) was then added and their binding detected with a secondary HRP-conjugated antibody. (c) Decay of HR1 groove exposure at different temperatures after pulse activation with sCD4 (40 μg/ml). Values represent the means(±s.e.m.) of two replicate samples.

Figure 3A:
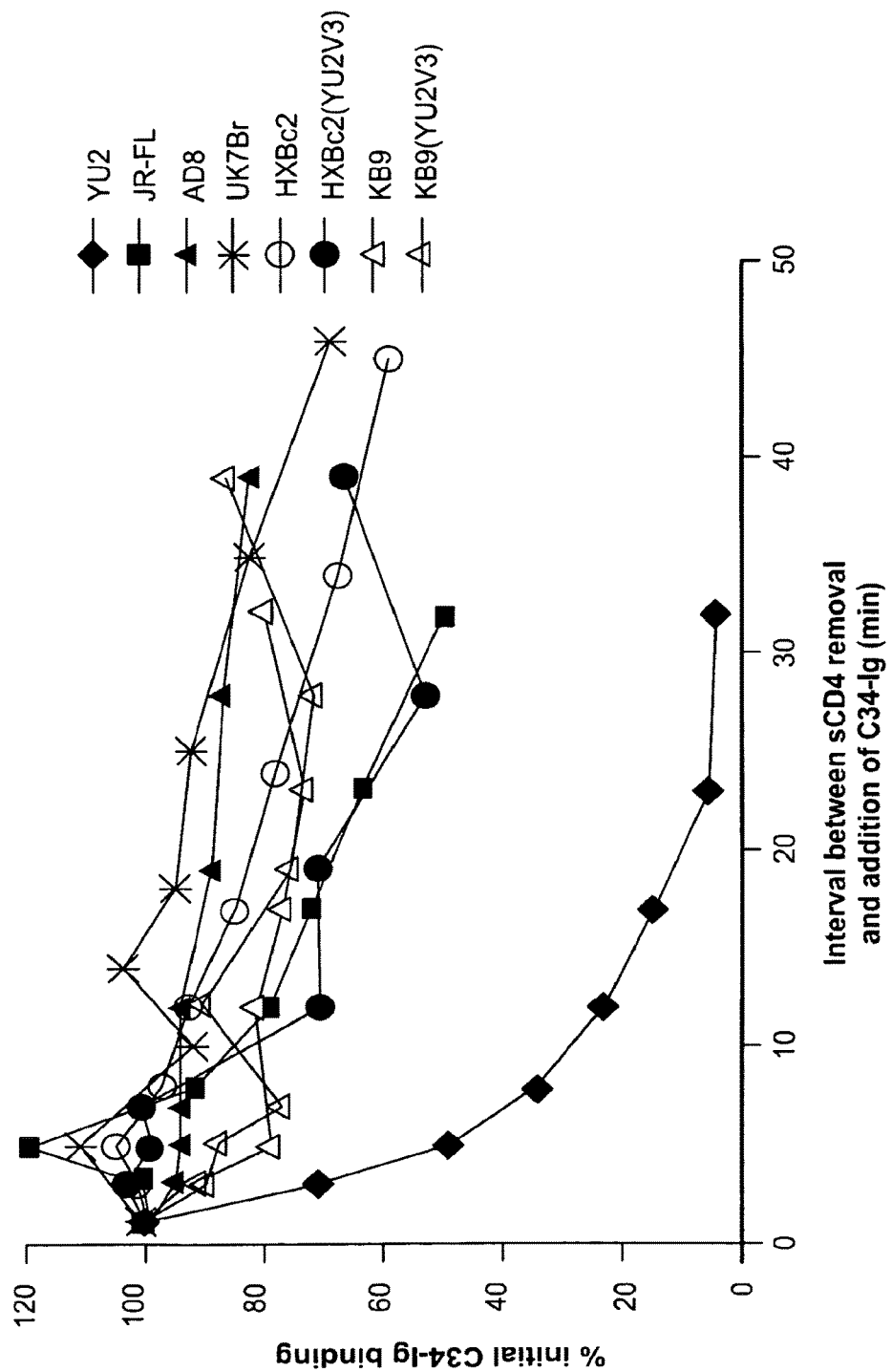
Figure 3B:
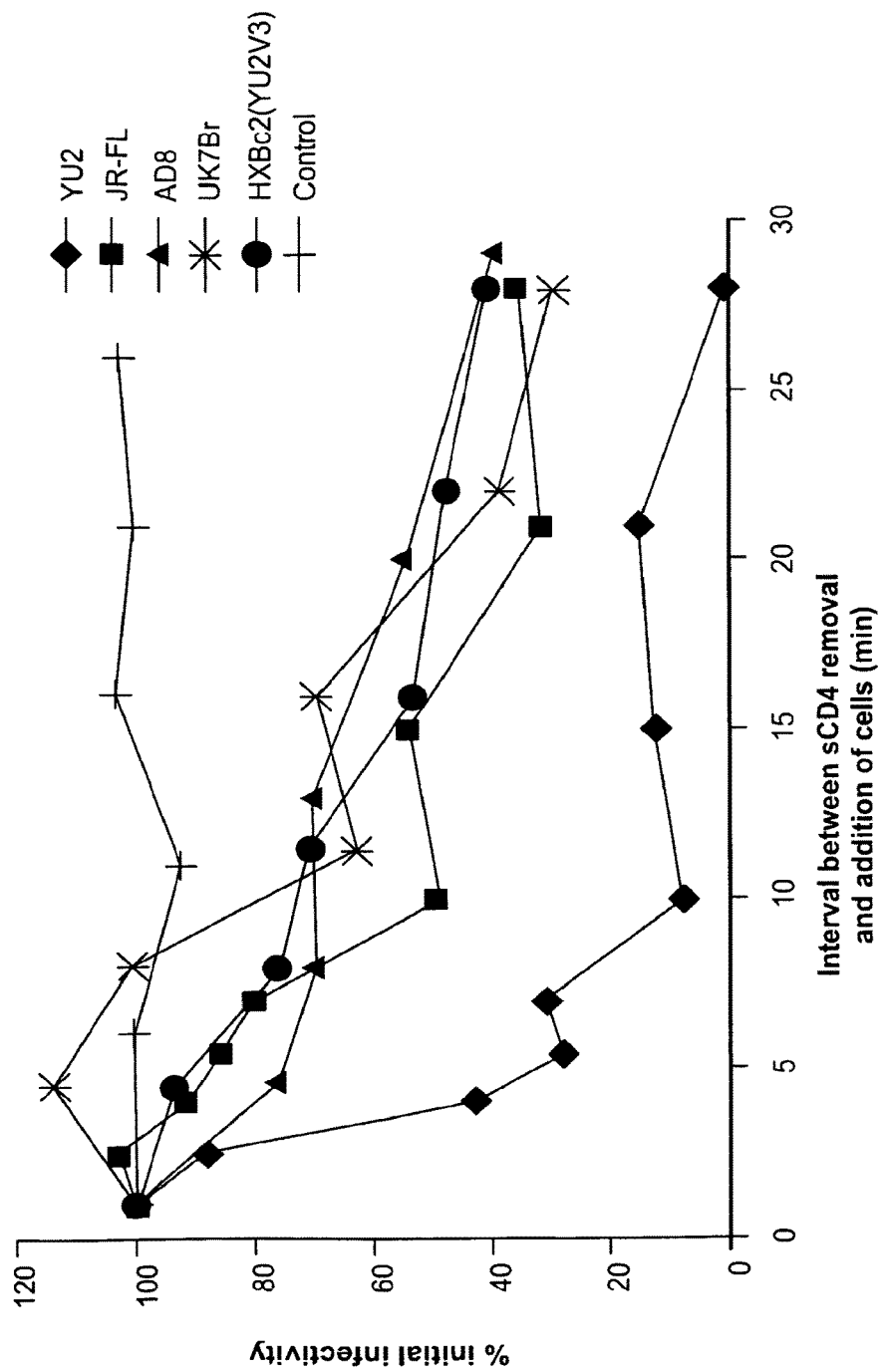
Figure 3C:
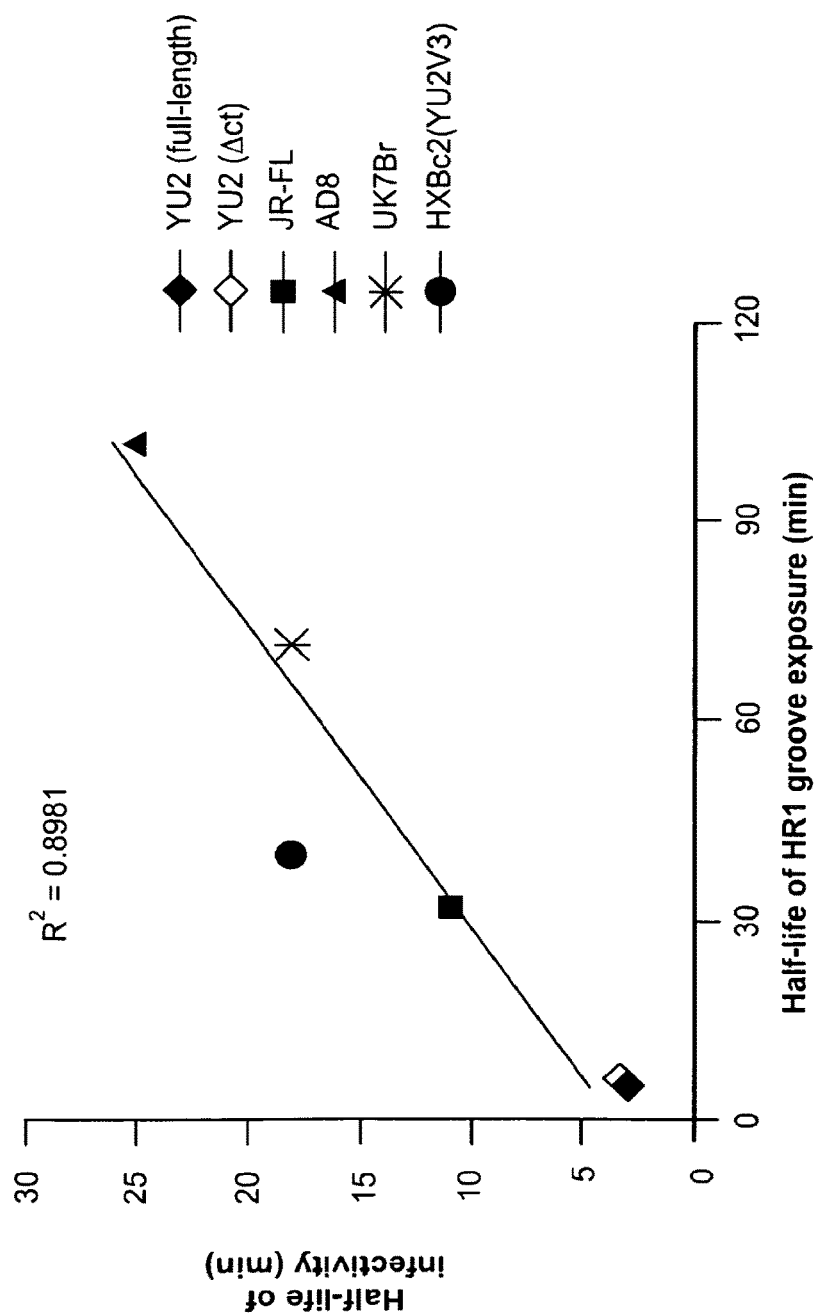

FIG. 3 shows the relationship of infectivity decay and loss of HR1 groove exposure. (a) Decay of HR1 groove exposure of different HIV Env gps at 25° C. after pulse activation with sCD4. COS-1 cells expressing the indicated HIV Env gps were pulsed with sCD4, followed by assessment of HR1 groove exposure. (b) Recombinant HIV carrying the indicated Env gps were pulsed with sCD4 (40 μg/ml) for 3 minutes and incubated at 25° C. After the indicated times, CD4$^-$CCR5$^+$ Cf2Th cells were added to the viruses. For the sample marked as control, HIV(YU2) was pulsed with buffer and then CD4$^+$CCR5$^+$ cells were added. Two days later, virus infectivity was assessed by measuring luciferase activity in the target cells. (c) The relationship of the decay rate of HR1 groove exposure and the decay rate of infectivity, after pulse activation with sCD4, is shown for the panel of HIV Env gps. Decay rates were measured at 25-27° C. Values represent the means derived from two to four separate experiments.

Figure 4A:
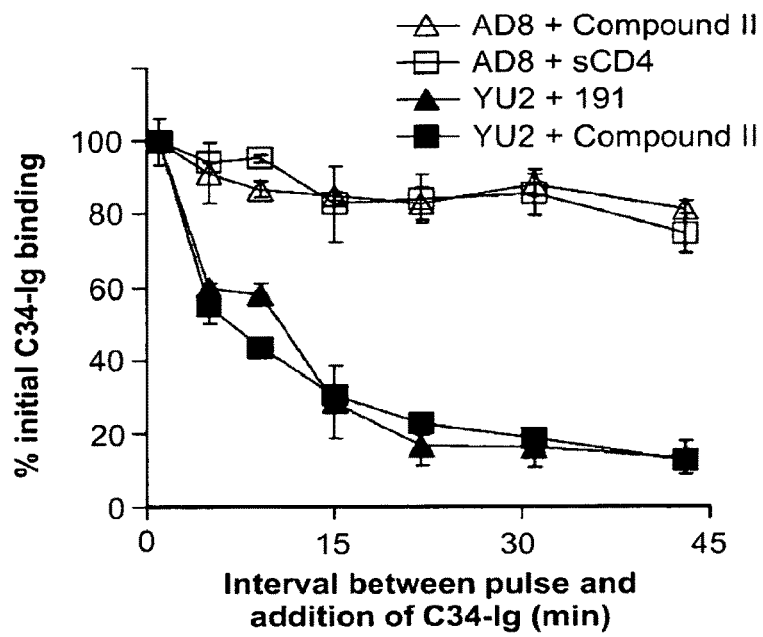
Figure 4B:
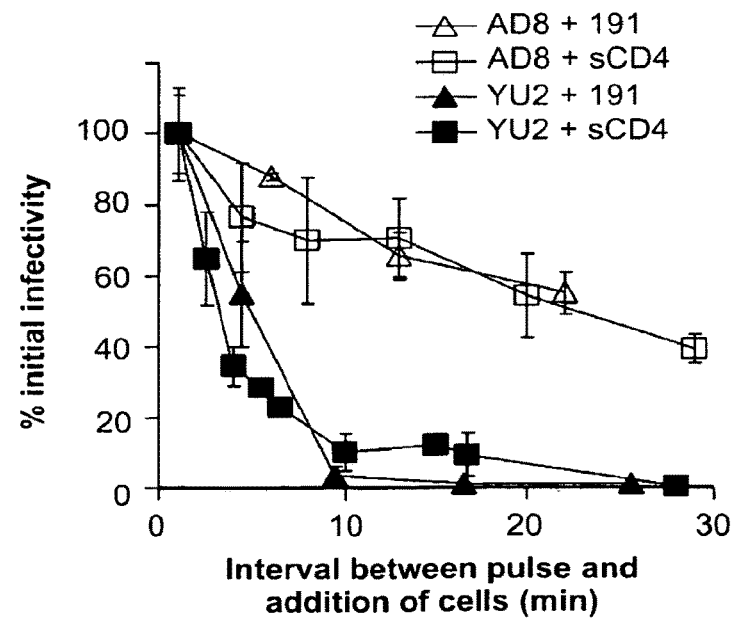

FIG. 4 shows the longevity of the HIV Env gp intermediate at room temperature after activation by sCD4 or 191. (a) The decay of HR1 groove exposure for cell-surface-expressed YU2 and AD8 Env gps is compared after pulse activation with compound II (310 μM) or sCD4 (40 μg/ml, 0.8 μM). (b) The decay of the ability to infect CD4$^-$CCR5$^+$ Cf2Th cells after pulse activation with compound II or sCD4 is compared.

FIG. 5 shows HIV activation by native CD4 and sCD4. (a) The stability of HR1 exposure was measured after activation of the YU2 or AD8 Env gps by cell-surface CD4. Background was defined as C34-Ig binding to cells transfected with the YU2-GS8 construct, which engages sCD4 with an affinity similar to that of the wild-type YU2 Env gps but does not expose the HR1 groove. Measurements were subtracted from background and are presented as percent (±s.e.m.) of C34-Ig binding measured at the initial time point. (b) The effect of the CCR5 antagonist, compound A (Madani et al. J. Virol. 81:532-538 (2007)), on infectivity of recombinant HIV pseudotyped with the indicated Env gps was investigated. Cf2Th-CD4/CCR5 cells were infected with HIV (AD8) or HIV(YU2) in the presence of increasing concentrations of compound A. Data are presented as the percentage (±s.e.m.) of infection measured in the absence of the compound. (c) The effect of CCR5 expression on the infection of CD4-expressing cells by HIV(AD8) or HIV (YU2) was examined. Cf2Th-CD4 cells were transfected with different amounts of a plasmid that expresses human CCR5. Two days later, transfected cells were infected with HIV(AD8) or HIV(YU2). Infectivity is expressed as the percentage (±s.e.m.) of infectivity measured for cells transfected with the highest amount of the CCR5-expressing plasmid. (d) The graph shows infection by cell-bound virus of CD4$^-$ Cf2Th cells transfected with different amounts of the CCR5-expressing plasmid in the presence of 20 μg/ml sCD4. Infectivity is expressed as the percentage (±s.e.m.) of infection measured in cells transfected with plasmids expressing CD4 and CCR5 (0.6 and 0.9 μg, respectively, of each plasmid per well.)

Figure 6A:
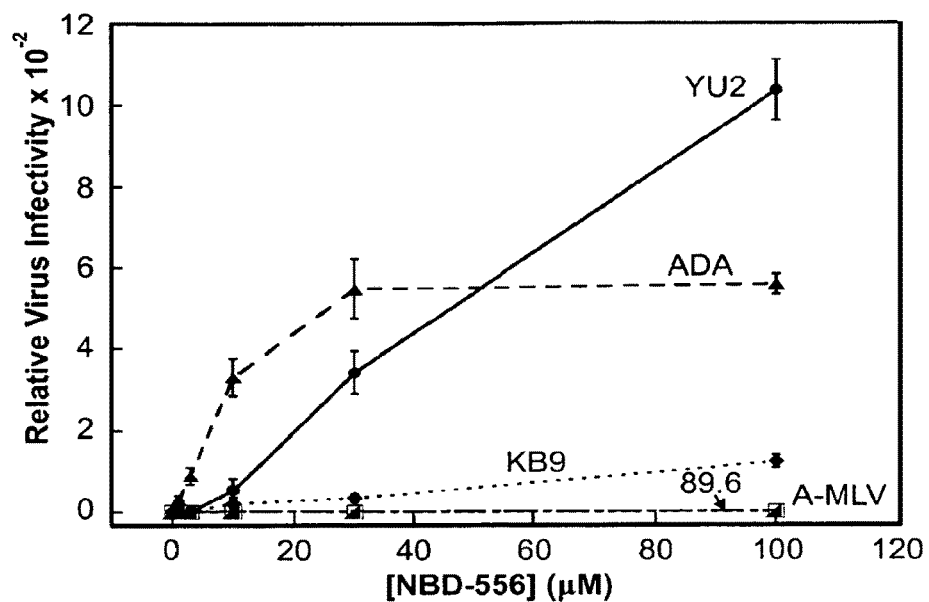

FIG. 6a shows the effect of incubating recombinant, luciferase-expressing HIV bearing the envelope glycoproteins of the indicated HIV strains with increasing concentrations of NBD-556 on infection of CD4-negative Cf2Th-CCR5 cells. Relative virus infectivity represents the amount of infection detected in the presence of the indicated concentration of compound divided by the infection detected in the absence of compound. A recombinant HIV with the A-MLV envelope glycoproteins is included as a control. The values shown are the means+/−SEM from a single experiment (n=3). The experiment was performed three times, with comparable results.

Figure 6B:
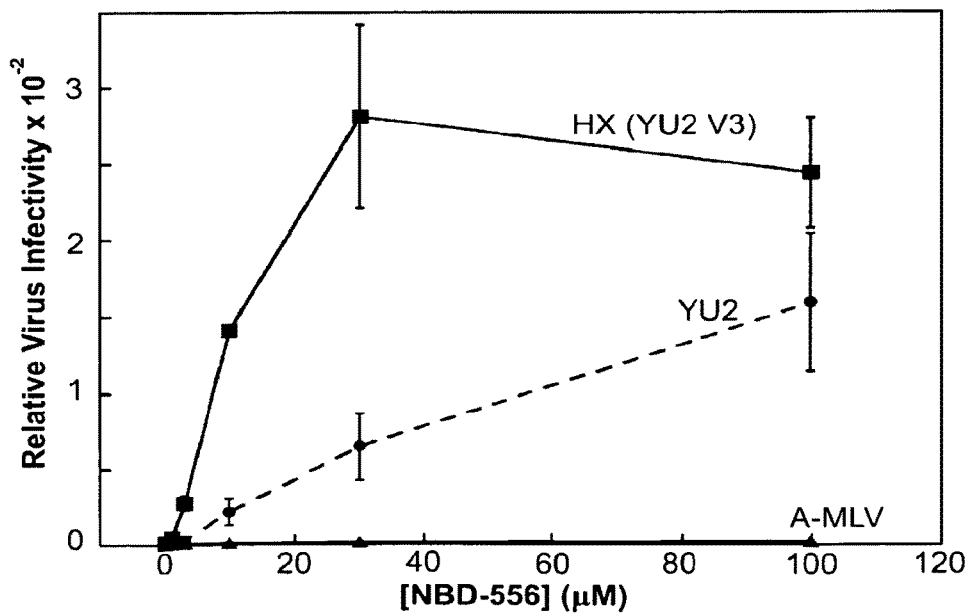

FIG. 6b shows the effect of incubating recombinant HIV bearing the YU2, HXBc2 or HX(YU2 V3) envelope glycoproteins with increasing concentrations of NBD-556 on infection of Cf2Th-CCR5 cells. The values shown are the means+/−SEM from a single experiment (n=3). The experiment was performed four times, with similar results.

Figure 7A:
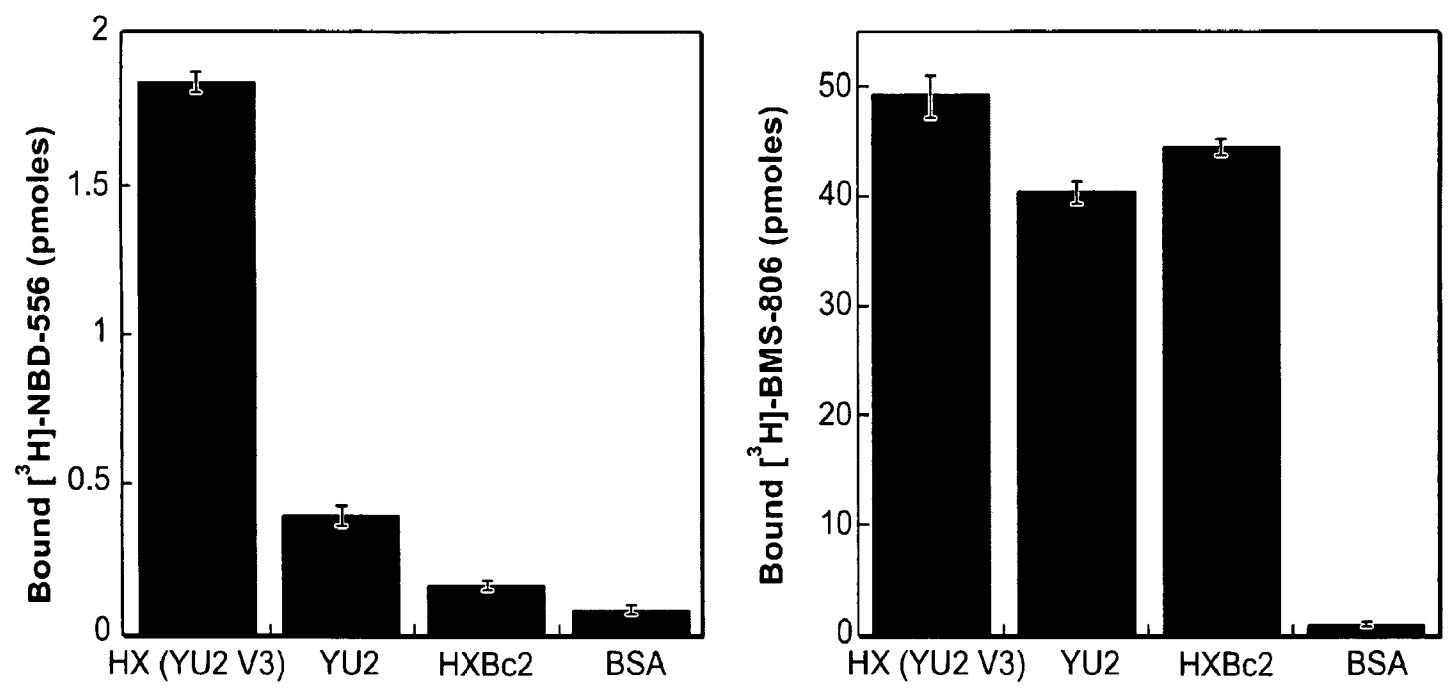

FIG. 7a shows the binding of [$^3$H]-NBD-556 (left panel) to the gp120 envelope glycoproteins from the indicated HIV strains or to bovine serum albumin (BSA). The right panel shows binding of the same gp120 envelope glycoproteins to [$^3$H]-BMS-806 as a control. The values shown are the means+/−SEM from one experiment (n=3).

Figure 7B:
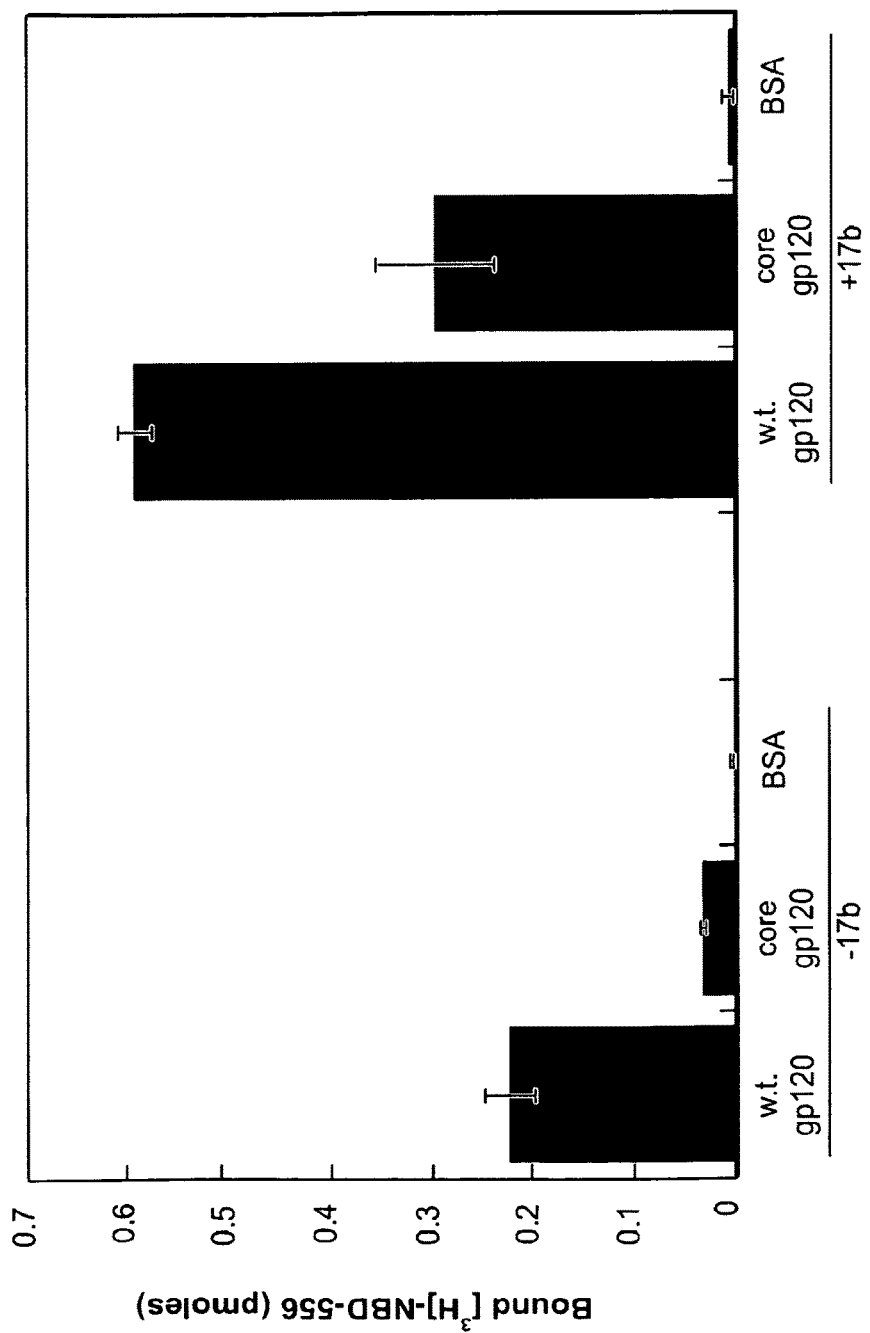

FIG. 7b shows the binding of [$^3$H]-NBD-556 to the HIVYU2 w.t. gp120 glycoprotein or to the gp120 core protein in the absence or presence of the 17b antibody (1 mg/ml). Binding of [$^3$H]-NBD-556 to the BSA control protein is shown for comparison. The values shown are the means+/−SEM from a single experiment (n=3). The experiment was performed three times with comparable results.

Figure 7C:
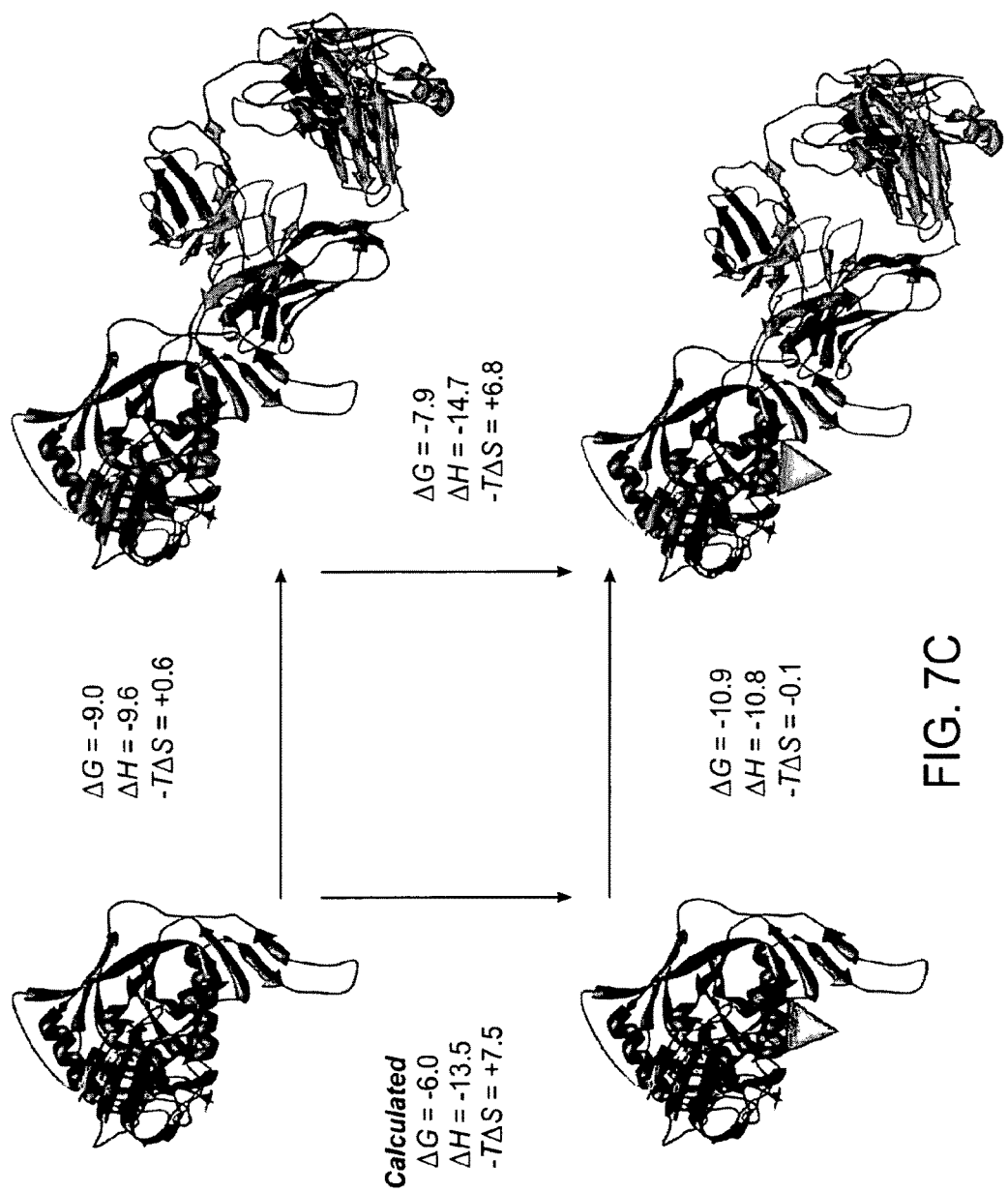

FIG. 7c shows the thermodynamic cycle for the binding of NBD-556 and the 17b antibody to the HIVYU2 gp120 core was studied by titrating the gp120 core with 17b in the presence of a saturating concentration of NBD-556. The values associated with the direct binding of NBD-556 to the gp120 core were calculated by completing the thermodynamic cycle. The structures of the gp120 core and the 17b Fab fragment (PDB entry 1GC1) are depicted in blue and red, respectively. NBD-556 is represented by the green triangle.

Figure 8:
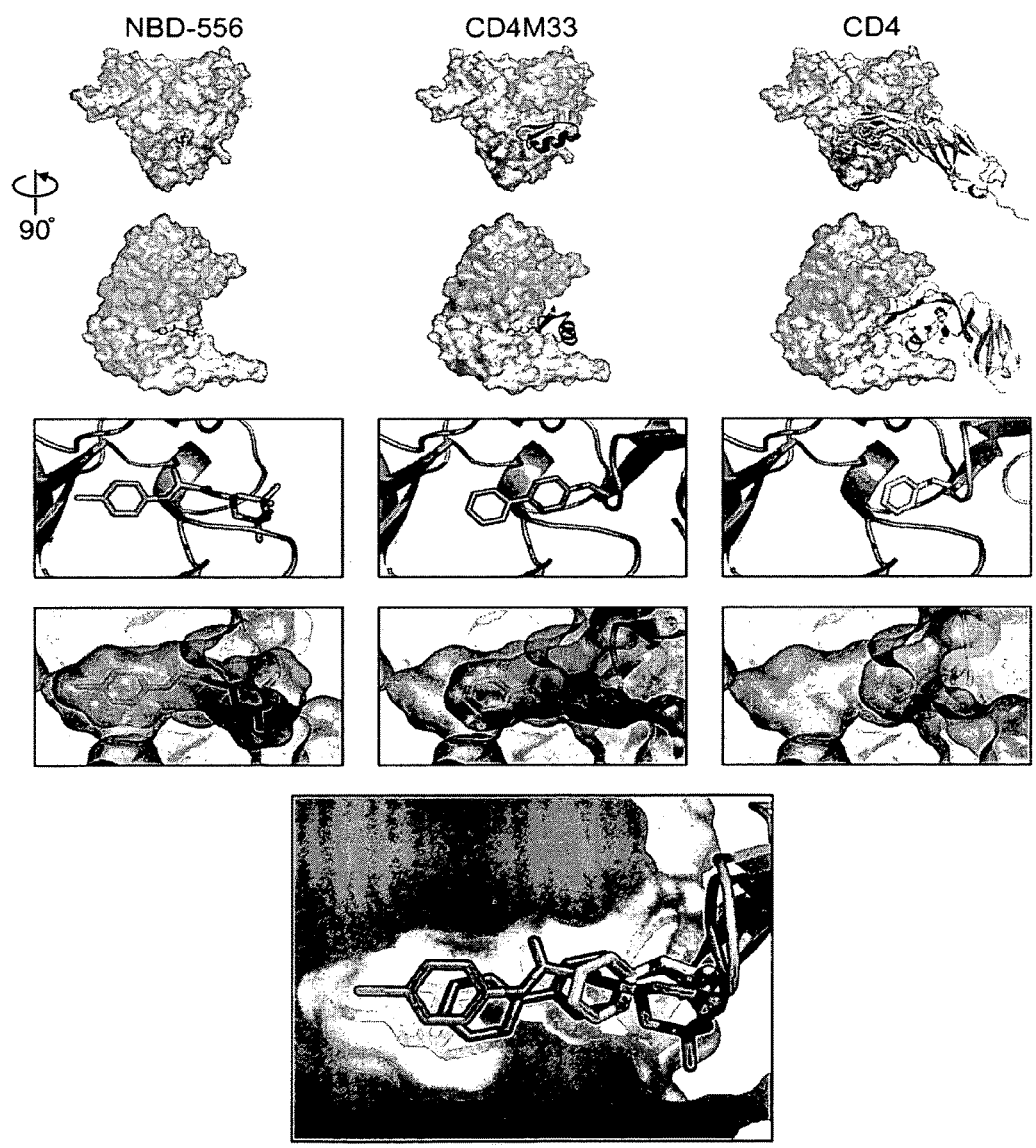

FIG. 8 shows, in the upper row, the molecular surface of the HIV gp120 core from the perspective of two-domain CD4, which is depicted as a ribbon structure in the right panels. In the second row, the gp120 core has been rotated 90° around the vertical axis. In the middle column, the CD4-mimetic miniprotein CD4M33 (ribbon structure) is docked onto the gp120 core, based on x-ray crystal structures of the CD4M33:gp120 core:17b Fab complex. In the left column, the bound NBD-556 has been modeled by the Glide program. In the third row, a close-up view of the gp120 region surrounding the Phe 43 cavity is shown. The gp120 structure is shown as a ribbon structure. In the right panel, Phe 43 of CD4 is shown. The biphenyl moiety of CD4M33 is shown in the middle panel. In the left panel, NBD-556 is shown. In the fourth row, the molecular surfaces of NBD-556, CD4M33, and CD4 are shown, illustrating the extent to which these ligands fill the Phe 43 cavity. In the bottom figure, CD4 Phe 43, the CD4M33 biphenyl group and the modeled NBD-556 are positioned together in the Phe 43 cavity.

Figure 9:
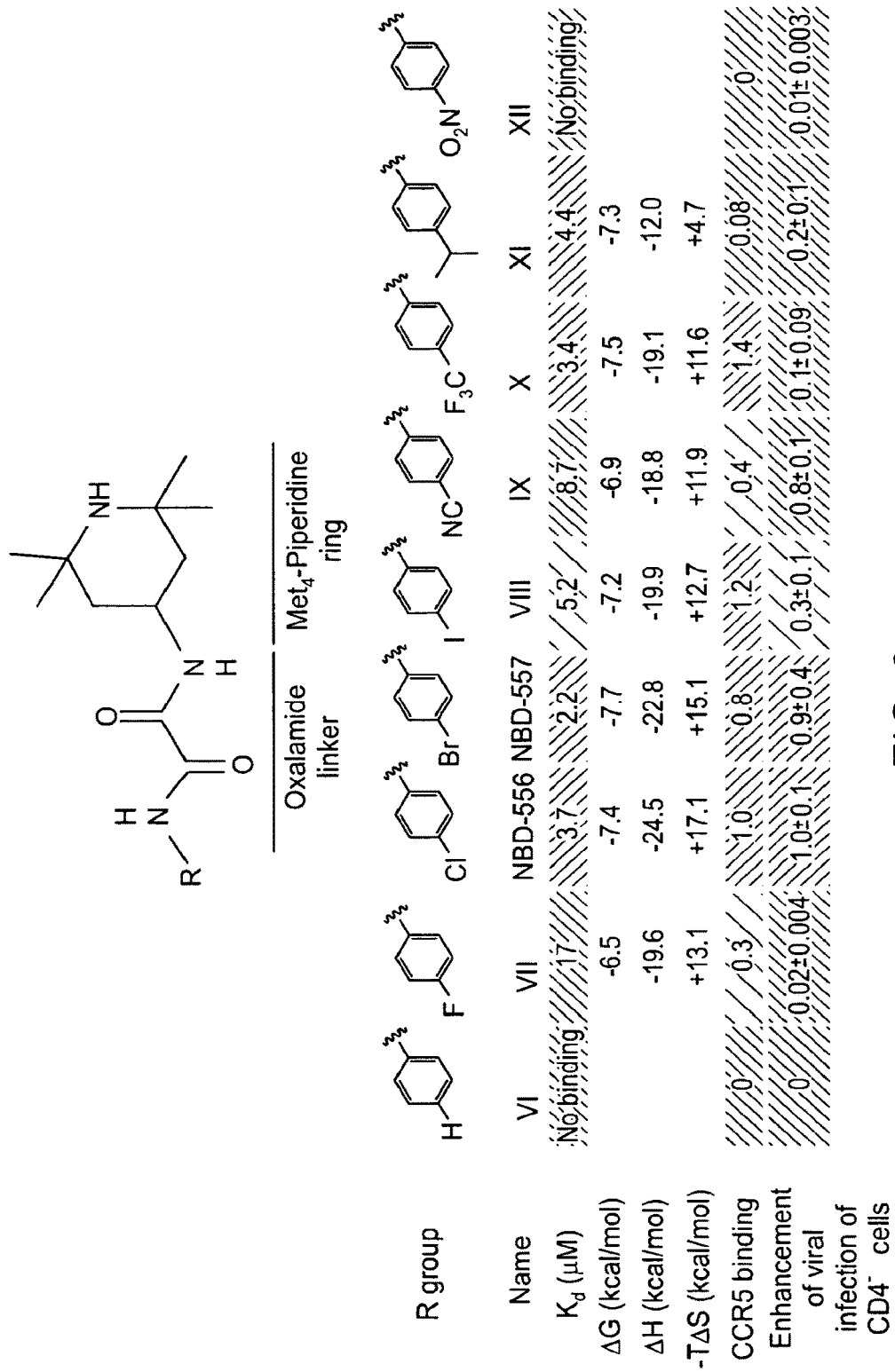

FIG. 9 shows the values for IQ, thermodynamic parameters, CCR5 binding, and enhancement of virus infection associated with the binding of compounds VI-XII of the present invention along with NBD-556 and NBD-557 to the w.t. HIVYU2 gp120 glycoprotein as determined by isothermal titration calorimetry, binding to CCR5 and enhancement of viral infection in CD4⁻ cells. CCR5 binding of radiolabeled HIVYU2 gp120 was determined after incubation with 10 μM compound. The induction of CCR5 binding by each compound was normalized to that observed for NBD-556. To study compound enhancement of infection of CD4 $CCR5^+$ cells, recombinant, luciferase-expressing HIV with the wild-type HIVYU2 envelope glycoproteins was incubated with increasing concentrations of the compound and then added to Cf2Th-CCR5 cells. Cells were lysed 48 h later and luciferase activity measured. The area under the dose-response curve for each compound was calculated and normalized to the value obtained for NBD-556.

FIG. 10 shows values for $K_d$, thermodynamic parameters, CCR5 binding and enhancement of virus infection of $CD4^-$ $CCR5^+$ cells for compounds II, V, and XIII-XV. In the CCR5-binding experiments, compounds II, V, and XIII-XV were used at a concentration of 1 μM. The 50% inhibitory concentration ($IC_{50}$) is shown for the compound's inhibition of infection of Cf2Th-CD4/CCR5 cells by recombinant HIV with the w.t. HIVYU2 envelope glycoproteins or with the control A-MLV envelope glycoproteins. In the first column, the values for NBD-556 are shown for comparison.

FIG. 11 shows values for $K_d$, thermodynamic parameters, CCR5 binding and enhancement of virus infection of $CD4^-$ $CCR5^+$ cells for compounds III, XVI-XVIII. In the CCR5-binding experiments, compounds III, XVI-XVIII were used at a concentration of 1 μM. The 50% inhibitory concentration ($IC_{50}$) is shown for the compound's inhibition of infection of Cf2Th-CD4/CCR5 cells by recombinant HIV with the w.t. HIVYU2 envelope glycoproteins or with the control A-MLV envelope glycoproteins. In the first column, the values for compound II are shown for comparison along with NBD-556 in the second column.

FIGS. 12*a* and 12*b* show the relationship between the entropy change ($-T\Delta S$) and (a) enthalpy change ($\Delta H$) associated with the binding of compounds II, V, VII, IX, X, XI, XIV, NBD-556, and NBD-557 to HIVYU2 gp120. The least-squares regression line is depicted, along with the $R^2$ value. FIG. 11*b* shows the relationship between the ability of compounds II, V, and VII-XI to enhance HIV infection of CCR5+ cells and the dissociation constant (IQ) and entropy change ($-T\Delta S$) associated with compound-gp120 binding is shown. The symbols associated with the compounds are colored according to the ability of the compound to promote HIV infection of CD4-CCR5+ cells. The color code is the same as that used in Tables 1 and 2, from red (none/low) to green (high level of enhancement).

FIG. 13*a* shows the binding of $[^3H]$-NBD-556 to equivalent amounts of the w.t. or S375W HIVYU2 gp120 glycoprotein or bovine serum albumin (BSA) is indicated. The means from a single experiment, with the standard errors derived from triplicate samples, are shown. The experiment was performed three times with comparable results.

FIG. 13*b* shows the amount of radiolabeled w.t. or S375W mutant HIVYU2 gp120 bound to Cf2Th-CCR5 cells, after incubation without (0) or with CD4-Ig (1 μg/ml), NBD-556 (100 μM) or BMS-806 (10 μM). Numbers indicate molecular weight (in kD).

FIG. 13*c* shows recombinant viruses bearing the w.t. or indicated mutant HIVYU2 envelope glycoproteins incubated with Cf2Th-CCR5 cells in the presence of increasing concentrations of NBD-556. Luciferase activity in the Cf2Th-CCR5 cells was measured, and the relative virus infectivity, compared with that observed in the absence of added NBD-556, is shown. The mean values and standard errors (from triplicate samples) are shown from a typical experiment.

FIG. 13*d* shows the location of HIVYU2 gp120 residues in which changes affect NBD-556 binding and/or entry enhancement. The modeled NBD-556 is shown penetrating into the Phe 43 cavity of gp120. The gp120 core is depicted as a $C_\alpha$ ribbon and transparent molecular surface. The HIVYU2 gp120 residues that, when changed, affect NBD-556 binding and/or enhancement of HIV entry into Cf2Th-CCR5 cells are labeled with side chain bonds shown.

FIG. 14 shows the area under the dose-response curve (in arbitrary units) determined for compounds II, V, VIII, X, XI, NBD-556, and NBD-557 incubated with the viruses bearing the indicated HIVYU2 envelope glycoprotein mutant (or A-MLV envelope glycoproteins). The value for this area was normalized to the value calculated for NBD-556 and the viruses with w.t. YU2 envelope glycoproteins in the same experiment. The numbers reported represent the mean values and standard deviations obtained from at least three independent experiments. The relative enhancement of infection of Cf2Th-CCR5 cells is color-coded as follows: red=0-0.24; yellow=0.25-0.7; green=>0.7.

FIG. 15*a* shows recombinant viruses bearing the w.t. or S375A HIVYU2 envelope glycoproteins or control viruses with the A-MLV envelope glycoproteins incubated with increasing concentrations of NBD-556 (open symbols) or compound II (filled symbols) and then added to Cf2Th-CD4/CCR5 cells. The level of infection was determined by luciferase assay. The percentage of infection relative to that seen in the absence of added compound is shown. The means and standard errors from a single experiment, performed with triplicate samples, are shown. The experiment was repeated 3-5 times with comparable results.

FIG. 15*b* shows the concentrations ($IC_{50}$) of NBD-556 and compound II inhibiting 50% of infection of Cf2Th-CD4/CCR5 cells by viruses bearing the indicated HIV envelope glycoproteins plotted against the $K_d$ for the binding of the compounds to the indicated HIV gp120 variants. The $IC_{50}$ values represent the means and standard deviations of values obtained in five independent experiments, with each experiment containing triplicate samples. The equation of the fitted curve is shown.

FIG. 16 shows $IC_{50}$ for inhibition of infection of CD4-positive, CCR5-positive cells by the HIV-1 YU2 strain, the dissociation constant ($K_d$) for binding HIV-1 gp120, and the relative stimulation of HIV-1 entry into CD4-negative, CCR5-positive cells. When HIV-1 viruses pseudotyped with the amphotropic murine leukemia virus (A-MLV) envelope glycoproteins were inhibited, the inhibition of the HIV-1 YU2 virus was considered non-specific, and is noted next to the $IC_{50}$. The amount of stimulation of HIV-1 (YU2) infection of CD4-negative, CCR5-positive cells is reported relative to that seen for compound 191. All values for $IC_{50}$ and $K_d$ are in micromolar.

FIG. 17A shows inhibitory concentration ($IC_{50}$) against the YU2 strain of HIV-1. FIG. 17B shows inhibitory concentration (IC) against the YU2 strain of HIV-1. As a control, the compounds were tested against a recombinant HIV-1 pseudotyped with the A-MLV envelope glycoproteins. Ideally, a specific inhibitor of HIV-1 entry should exhibit a low $IC_{50}$ for YU2 and a high $IC_{50}$ for A-MLV. All values are in micromolar. The "R5 Area" values indicate whether the compound acts like a mimic of CD4, the HIV-1 receptor. Cells expressing only the second HIV-1 receptor, CCR5, were incubated with HIV-1 and increasing amounts of the compound. The amount of stimulation of infection (relative to that seen for Compound 191) is indicated. It was found that most CD4-mimetic compounds that block HIV-1 entry into CD4-positive, CCR5-positive cells, exhibit the ability to induce HIV-1 entry into CCR5-positive, CD4-negative cells. This suggests that part of the antiviral activity of NBD-556 and analogues results from the ability of these compounds to trigger prematurely unstable envelope glycoprotein intermediates (Haim et al., PLoS Pathogens 5:e1000360 (2009)).

DETAILED DESCRIPTION OF THE INVENTION

Definitions

As used herein, "HIV" refers to any virus that can infect a host cell of a subject through activation of the gp120 envelope glycoproteins (Env gps). "HIV" encompasses all strains of HIV-1 and HIV-2. Compounds of the present invention, however, are also useful to treat other immunodeficiency viruses expressing gp120 such as some strains of simian immunodeficiency virus SIV.

As used herein "gp120" refers to the gp120 envelope glycoprotein, and "Env gps" refers to the complete envelope glycoprotein complex which is a trimer of three gp120s and three gp41s.

As used herein, the term "activating" when referring to gp120 envelope glycoprotein means the association of a natural or non-natural ligand with the conserved domain of gp120 that induces a conformational change that activates binding to the chemokine receptors CCR5 or CXCR4. Examples of natural ligands include CD4 and sCD4. Examples of non-natural ligands include compounds of the present invention as well as NBD-556 and NBD-557.

As used herein "activated intermediate" refers to the gp120 envelope glycoprotein in bound form with CD4, sCD4, or compounds of the present invention.

As used herein, the term "contacting" when used in the context of compounds of the present invention and gp120, refers to the process of supplying compounds of the present invention to the HIV envelope glycoprotein either in vitro or in vivo in order effect the selective binding of the compounds of the present invention to the conserved Phe43 binding pocket of gp120. For the in vitro process, this can entail simply adding an amount of a stock solution of one or more compounds of the present invention to a solution preparation of gp120. For an in vivo process, "selective binding" involves making compounds of the present invention available to interact with gp120 in a host organism, wherein the compounds of the invention exhibit a selectivity for the conserved domain of gp120 that define the Phe43 cavity. Making the compounds available to interact with gp120 in the host organism can be achieved by oral administration, intravenously, peritoneally, mucosally, intramuscularly, and other methods familiar to one of ordinary skill in the art.

As used herein, the term "inhibiting" when referring to transmission means reducing the rate of or blocking the process that allows fusion of the viral glycoprotein gp120 to a host cell and introduction of the viral core into the host cell. In this regard, inhibiting transmission includes prophylactic measures to prevent viral spread from one host organism to another. When referring to progression, "inhibiting" refers to the treatment of an already infected organism and preventing further viral invasion within the same organism by blocking the process that allows fusion of the viral glycoprotein gp120 and introduction of viral core into additional host cells of the organism.

The term "alkenyl," as used herein, alone or in combination, refers to a straight-chain or branched-chain hydrocarbon radical having one or more double bonds and containing from 2 to 20 carbon atoms in one embodiment, 2 to 6, carbon atoms in other embodiments. Examples of suitable alkenyl radicals include, without limitation, ethenyl, propenyl, 2-methylpropenyl, butenyl, 1,4-butadienyl and the like. Where relevant, such carbon-carbon double bonds can be of E or Z configuration.

The term "alkyl," as used herein, alone or in combination, refers to a straight-chain or branched-chain alkyl radical containing from 1 to about 20 carbon atoms in one embodiment, 1 to 10 in another embodiment, and 1 to 6 in still other embodiments. Alkyl groups can be optionally substituted as defined herein. Alkyl groups can be referred to also as "lower" alkyl when referring to structures having 1 to about 6 carbons in one embodiment and from 1 to about 4 carbons in another embodiment. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. Examples of alkynyl radicals include, without limitation, ethynyl, propynyl, hydroxypropynyl, butyn-1-yl, butyn-2-yl, pentyn-1-yl, 3-methylbutyn-1-yl, hexyn-2-yl, and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which can themselves be optionally substituted.

The term "aralkyl," also sometimes called arylalkyl, as used herein, alone or in combination, refers to an aryl or heteroaryl group attached to the parent molecular moiety through an alkyl group.

The term "aryl," as used herein, alone or in combination, means a carbocyclic aromatic system containing one, two or three rings wherein such rings can be attached together in a pendant manner or can be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "heteroaryl," as used herein, alone or in combination, refers to 3- to 7-membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "halogen," "halo," or "hal," as used herein, alone or in combination, refers to fluorine, chlorine, bromine, or iodine.

The term "optionally substituted" means the anteceding group can be substituted or unsubstituted. When substituted, the substituents of an "optionally substituted" group can include, for example, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower hydroxyalkyl, lower hydroxyalkenyl, lower hydroxyalkynyl, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —$CH_2CH_3$), fully substituted (e.g., —$CF_2CF_3$), monosubstituted (e.g., —$CH_2CH_2F$) or substituted at a level in-between fully substituted and monosubstituted (e.g., —$CH_2CF_3$).

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,
—OH, protected hydroxy,
—$NO_2$, —CN,
—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino,
—O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, -D-aryl, —O-heteroaryl, —O-heterocycloalkyl,
—C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl,
—$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl,
—$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl,
—NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl,
—C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl,
—S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl,
—$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl,
—$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts can be of utility in the preparation and purification of the compound in question. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds of the present invention which are water or oil-soluble or dispersible and therapeutically acceptable. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

As used herein, "an effective amount" is intended to mean an amount sufficient to prevent, reduce, or eliminate the infection. In some embodiments an effective amount can range from nanomolar concentrations to micromolar concentrations, for example, from about 1 nM to about 1,000 μM. One skilled in the art will recognize that to achieve these concentrations in vivo there will be a particular dependence on the pharmacokinetics of the exact compound selected. Thus, in some embodiments, a dose may range from about 1 mg/Kg to about 1,000 mg/Kg, including all quantities in between, and from about 10 mg/Kg to about 500 mg/Kg in other embodiments, and from about 50 mg/Kg to about 250 mg/Kg in yet other embodiments.

Compounds of the Invention

This invention is directed, in part, to compounds that are mimetics of CD4 that are useful as prophylactic agents against and/or inhibit the progression of human immunodeficiency virus (HIV) infection. Binding to the CD4 receptor induces conformational changes in the HIV gp120 exterior envelope glycoprotein. These changes allow gp120 to bind the co-receptor, either CCR5 or CXCR4, and activate the gp41 transmembrane envelope glycoprotein to mediate virus-cell membrane fusion and virus entry. Compounds of the present invention bind to a conserved pocket of gp120 and initiate conformational changes in the protein analogous to those observed with CD4. While such mimicry could enhance infection, Applicants have discovered that such conformational changes induced by compounds of the present invention are transient and this activated state of gp120 undergoes rapid and apparently irreversible further changes in conformation that result in loss of functional competence. Thus, compounds of the present invention can act as inhibitors of HIV transmission to a cell by intercepting binding of the natural ligand CD4 and by prematurely triggering the envelope glycoproteins to undergo irreversible conformational changes.

In one aspect, the invention provides a compound of formula I:

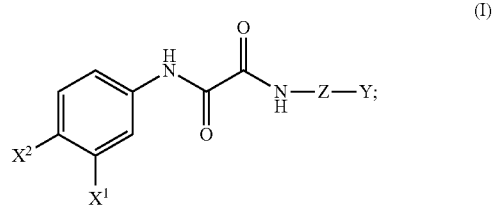

wherein
Z is absent or $(CR_AR_B)_nW$;
each $R_A$ and $R_B$ is independently (i) H, alkyl, alkenyl, alkynyl, cycloalkyl, heterocycloalkyl, aryl, heteroaryl, aralkyl, heteroaralkyl, haloalkyl, each of which may be optionally substituted; (ii) OH, $OR_C$, $NH_2$, $NHR_C$, $NR_CR_C$, SH, $S(O)_mR_C$; or (iii) $R_A$ and $R_B$ together form C(O);
W is absent, C(O), C(O)O, $C(O)NR_CR_C$, O, $S(O)_m$, or $NR_CR_C$;
Y is an optionally substituted heterocyclic, optionally substituted heteroaryl, optionally substituted cycloalkyl, optionally substituted aryl, or $NR_XR_Y$; wherein $R_X$ and $R_Y$ are each independently H, alkyl or aryl;
$X^1$ is selected from the group consisting of halogen, methyl, and hydroxyl;
$X^2$ is a halogen;
each $R_C$ is independently H, alkyl, cycloalkyl, heterocycloalkyl, aryl, heteroaryl, aralkyl, or heteroaralkyl, each of which may be optionally substituted;
m is 0, 1, or 2; and
n is 1, 2, 3, 4, 5, or 6.

In one embodiment, Z is absent, $CH_2$, $CH_2CH_2$, $CH(CH_3)$, $CH_2CH$(alkyl), $CH_2CH$(alkenyl), $CHNH_2$, $CH_2CHN(R')(R')$, $CH_2CH(R')$, $CH(R')CH(R')$, or $CH_2CH_2C(R')(R')$; wherein each R' is independently alkyl, haloalkyl, hydroxyl, heterocyclic. In another embodiment, W is absent, $C(O)NR_CR_C$, or $NR_CR_C$.

In certain embodiments, Y is cyclopropyl, cyclobutyl, cyclopentyl, cyclohexyl, cycloheptyl, cyclooctyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, or $NR_XR_Y$; each of which may be optionally substituted.

In a related embodiment, Y is

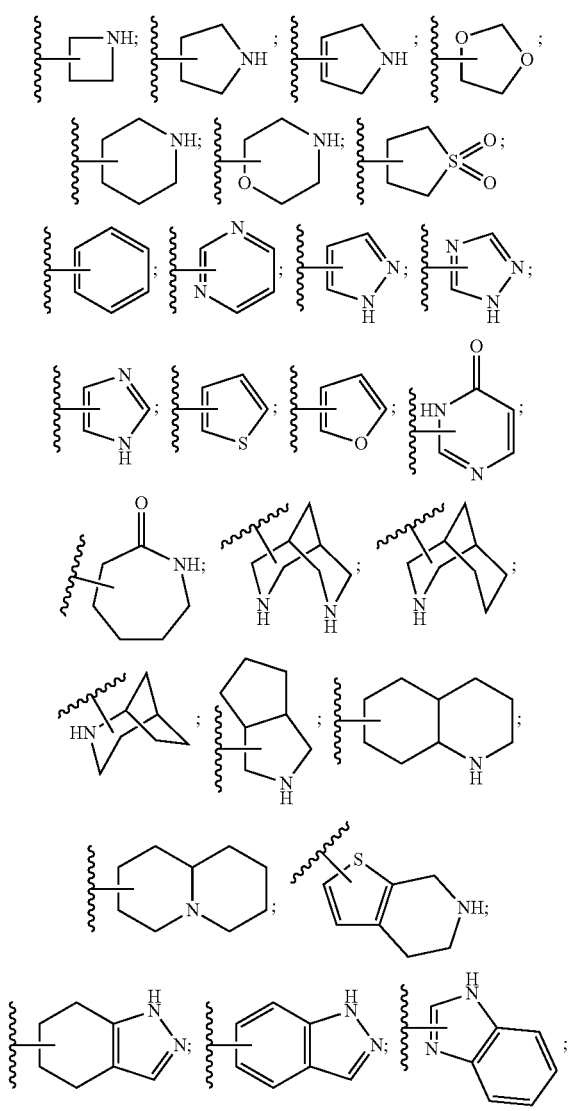

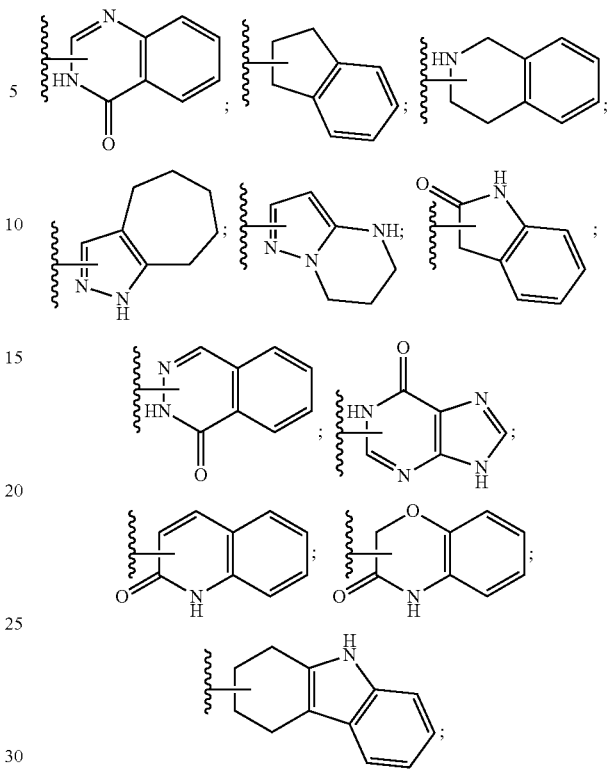

each of which may be optionally substituted.

In a first embodiment, the invention provides a compound formula IA

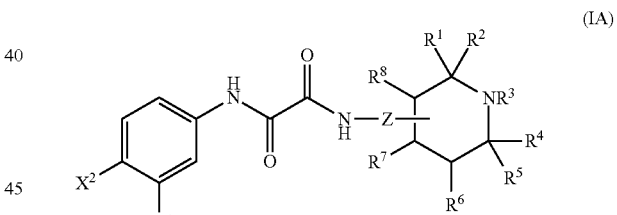

wherein $X^1$ is selected from the group consisting of halogen, methyl, and hydroxyl;

$X^2$ is a halogen;

Z is absent or $(CR_AR_B)_nW$;

$R^1$, $R^2$, $R^4$, $R^5$, $R^6$, $R^7$, and $R^8$ are each independently selected from the group consisting of hydrogen, hydroxyl, amino, and lower alkyl groups, each of which may be optionally substituted, or may for a bond with Z;

$R^3$ is selected from the group consisting of hydrogen, alkyl, alkenyl, alkynyl, and aralkyl, each of which may be optionally substituted, or may form a bond with Z;

and pharmaceutically acceptable salts thereof.

In one embodiment, $X^2$ is chlorine. In other embodiments, $X^1$ is chlorine or fluorine.

In one embodiment, the invention provides compounds of the structure given by formula IB:

IB

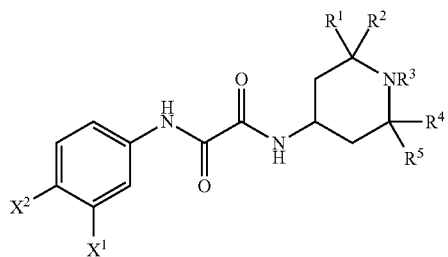

wherein $X^1$ is selected from the group consisting of halogen, methyl, and hydroxyl any of which are optionally substituted;

$X^2$ is a halogen;

$R^1$, $R^2$, $R^4$, and $R^5$ vary independently and are selected from the group consisting of hydrogen, hydroxyl, amino, and lower alkyl groups any of which can be optionally substituted; and $R^3$ is selected from the group consisting of hydrogen, alkyl, alkenyl, alkynyl, and aralkyl any of which can be optionally substituted.

In certain embodiments, $X^2$ is chlorine. In another embodiment, $X^1$ is chlorine or fluorine.

In other embodiments, $R^1$, $R^2$, $R^4$, and $R^5$ are methyl. In various embodiments, $R^3$ is hydrogen.

In certain embodiments, the invention provides a compound selected from the following:

II

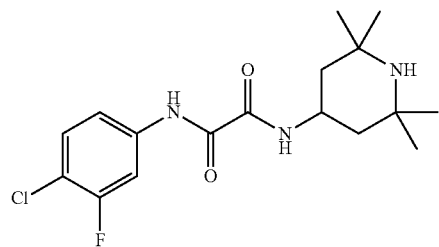

III

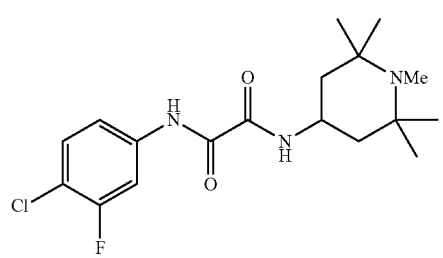

XVI

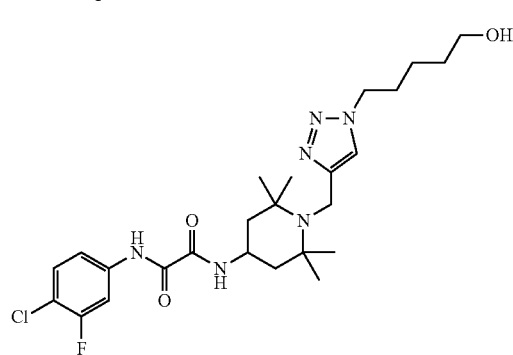

XVII

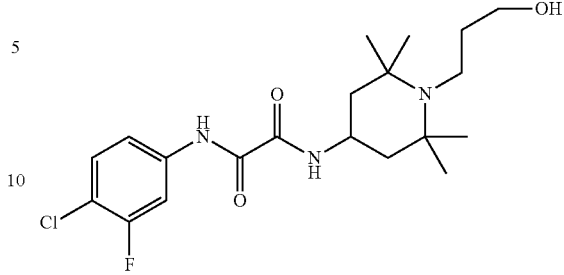

XVIII

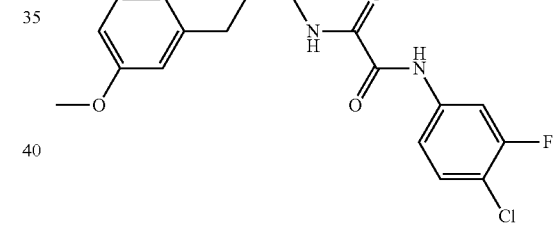

XXII

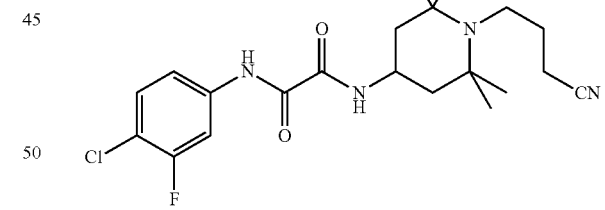

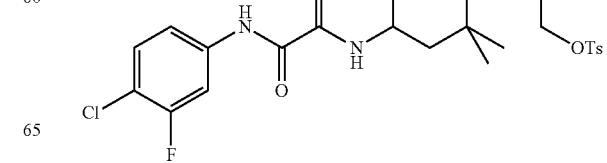

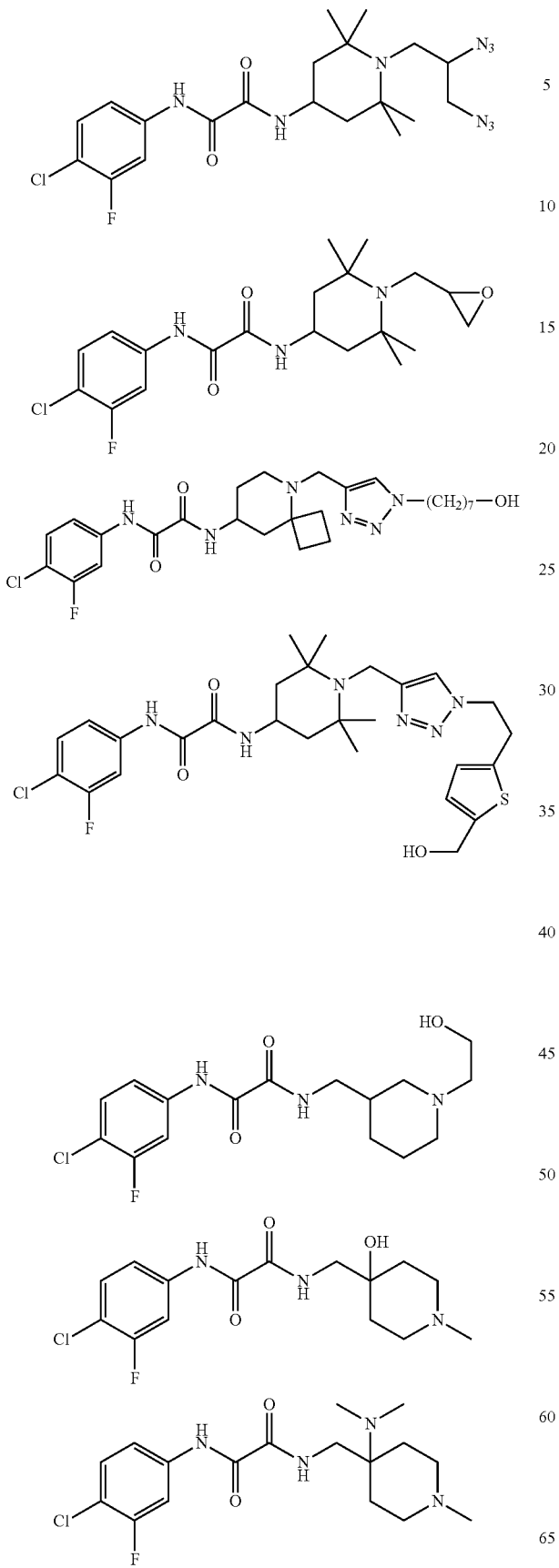
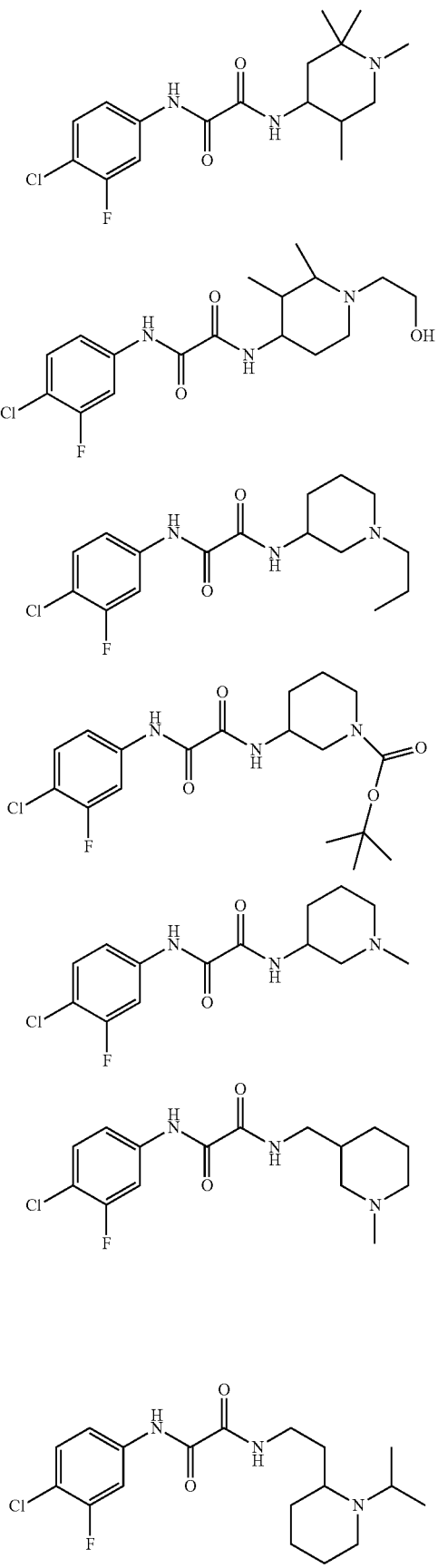

-continued
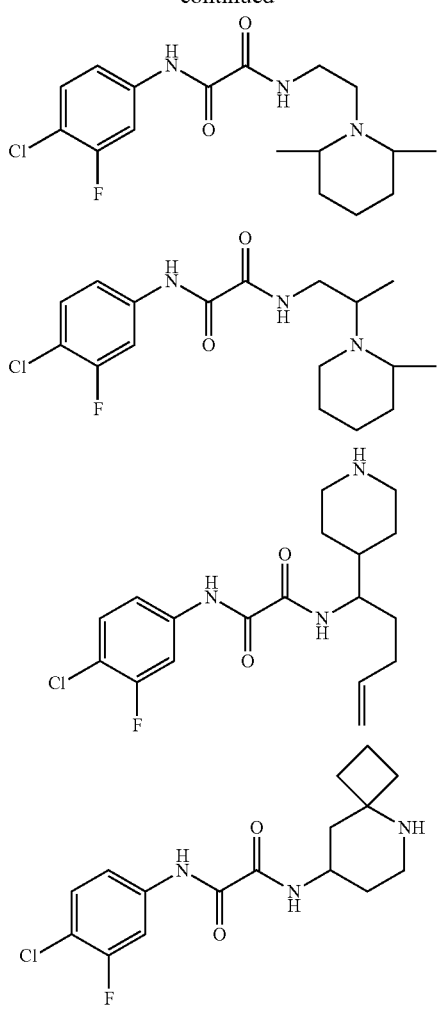
In other embodiments, the invention provides a compound selected from the following:
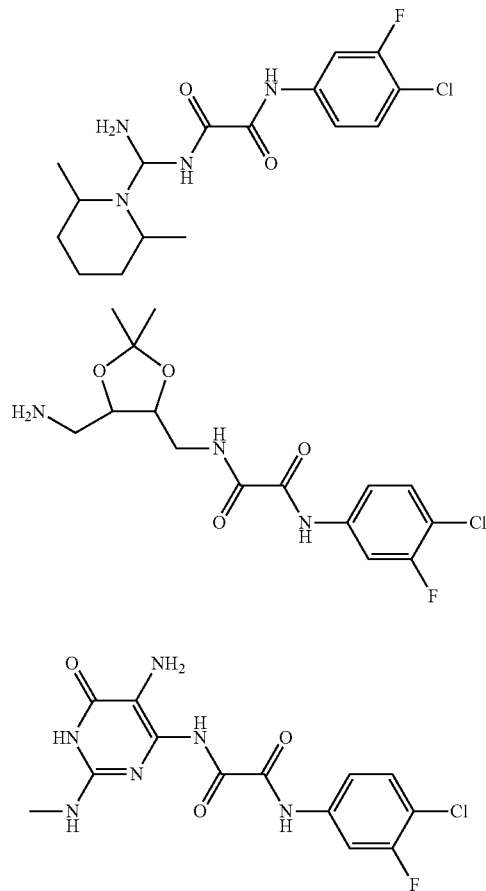
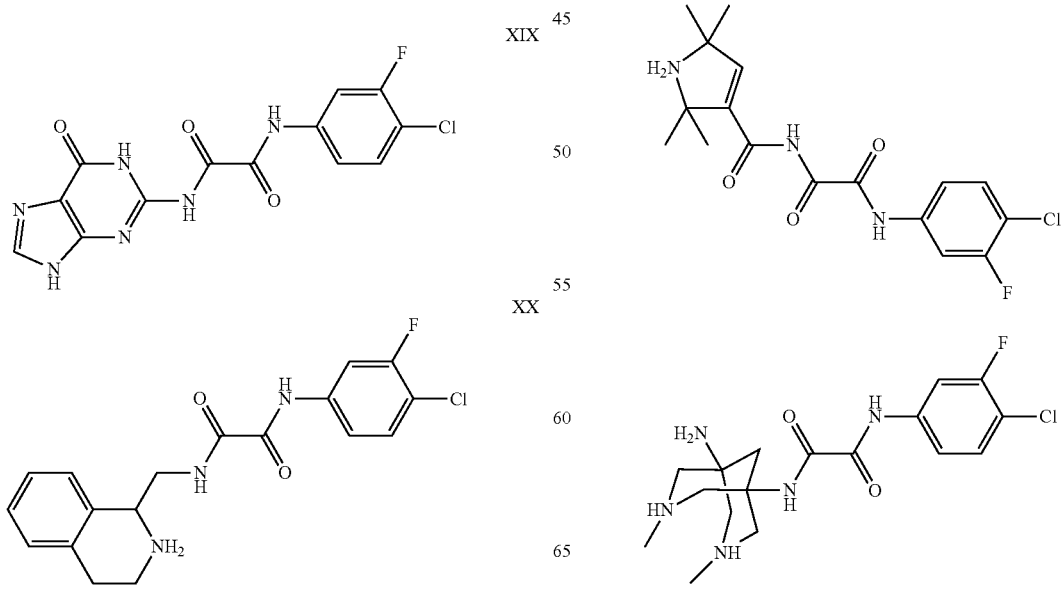

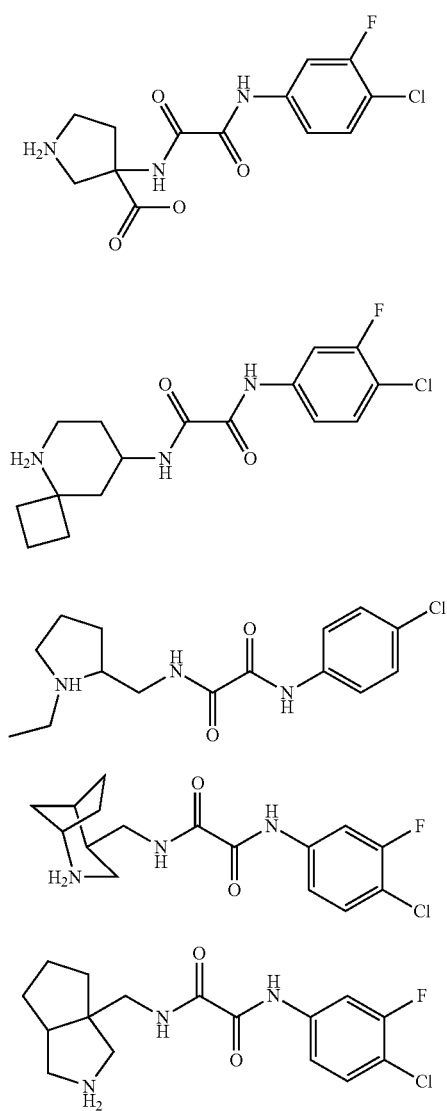
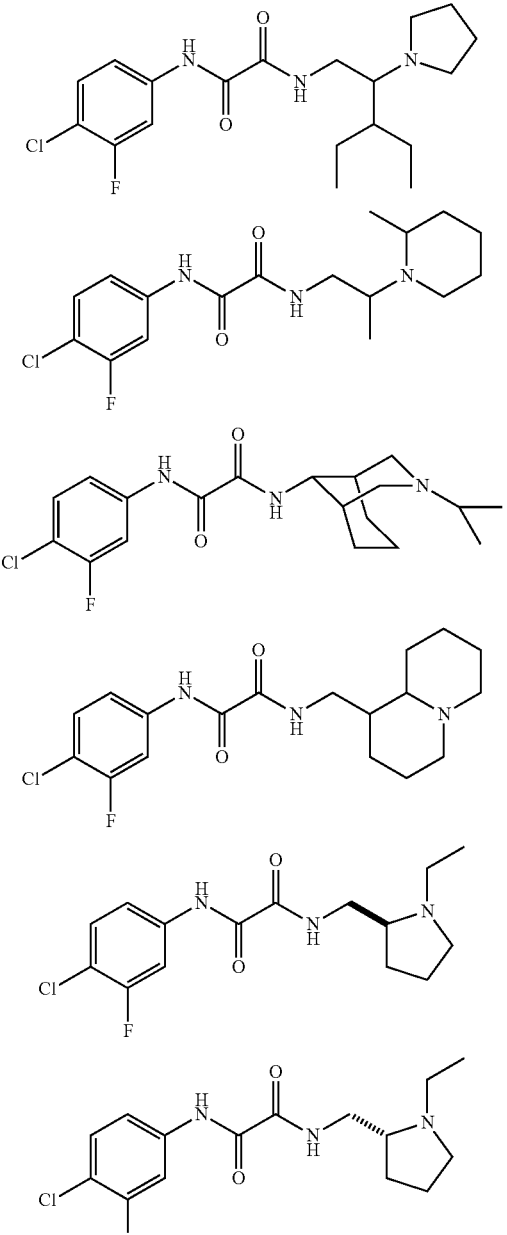
In other embodiments, the invention provides a compound selected from the group consisting of:
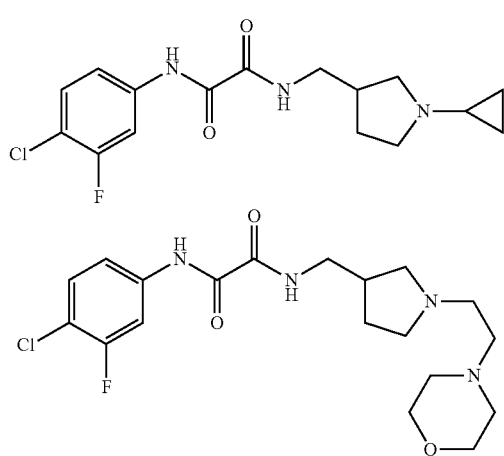
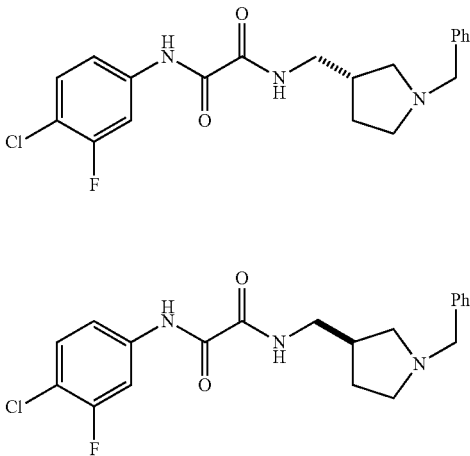

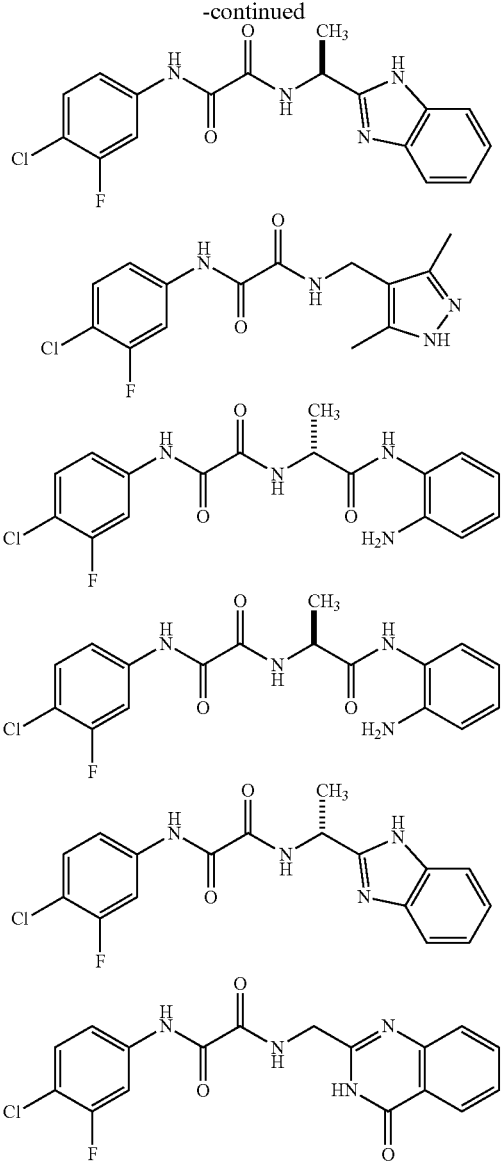
The invention also provides a compound selected from the group consisting of:
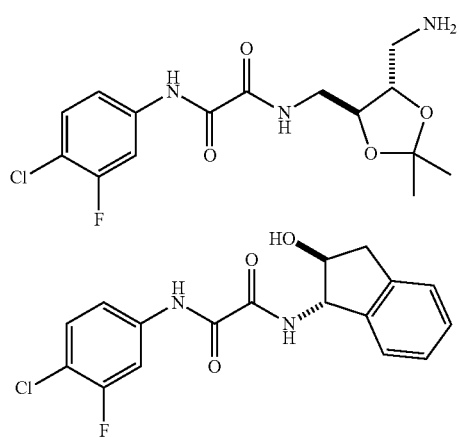
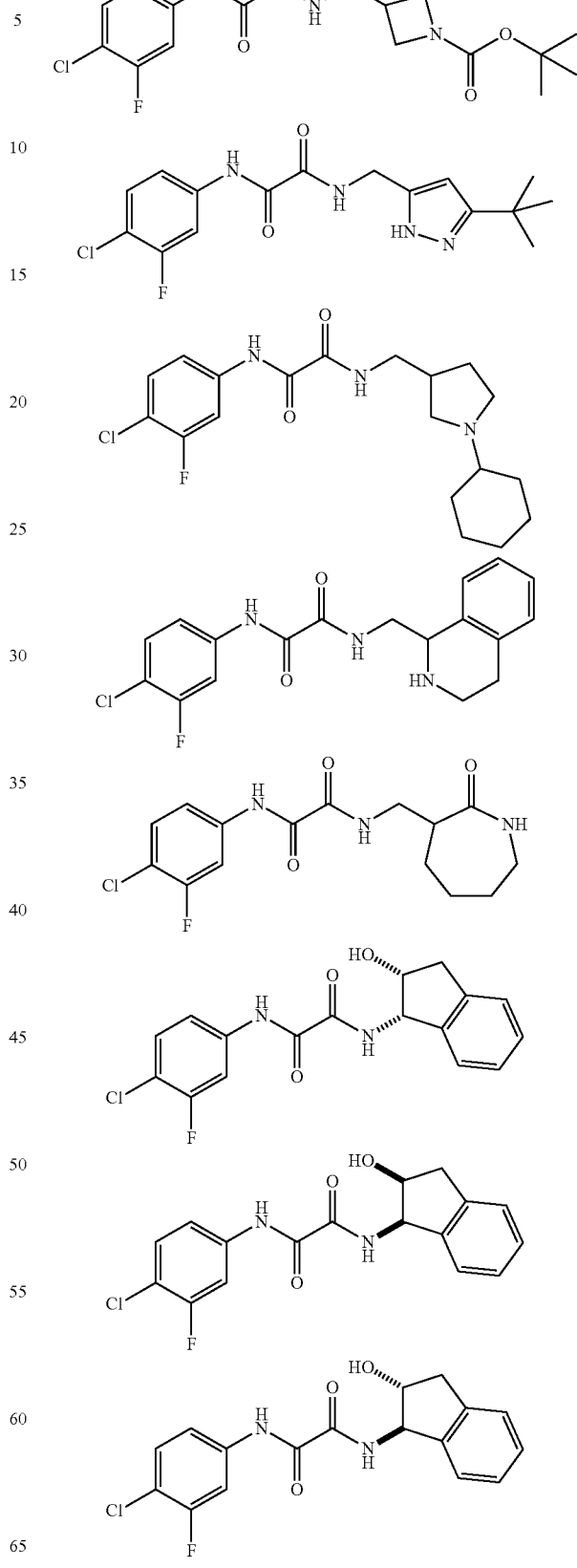

In certain embodiments, the invention provides a compound selected from the group consisting of:
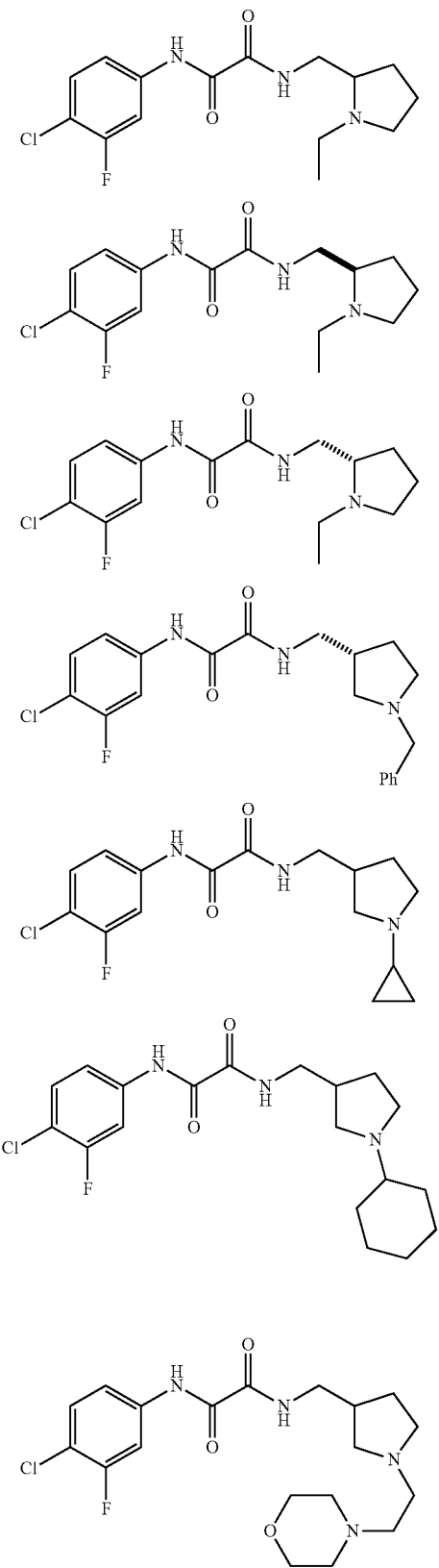
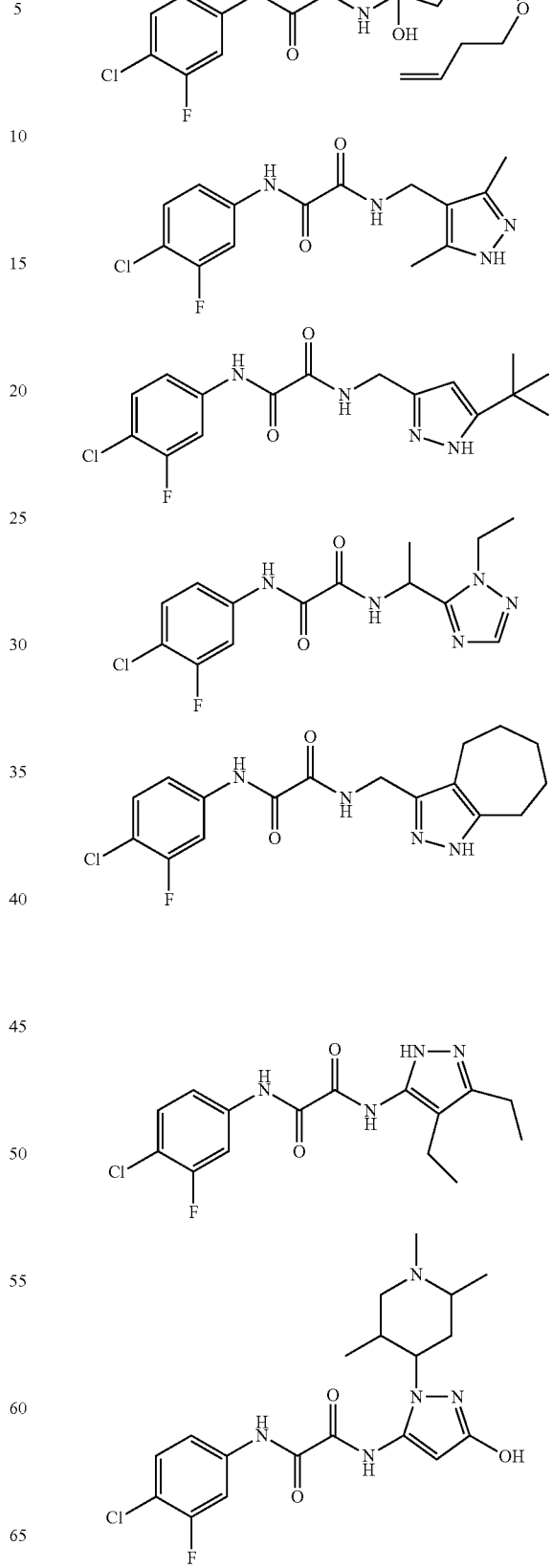

27
-continued
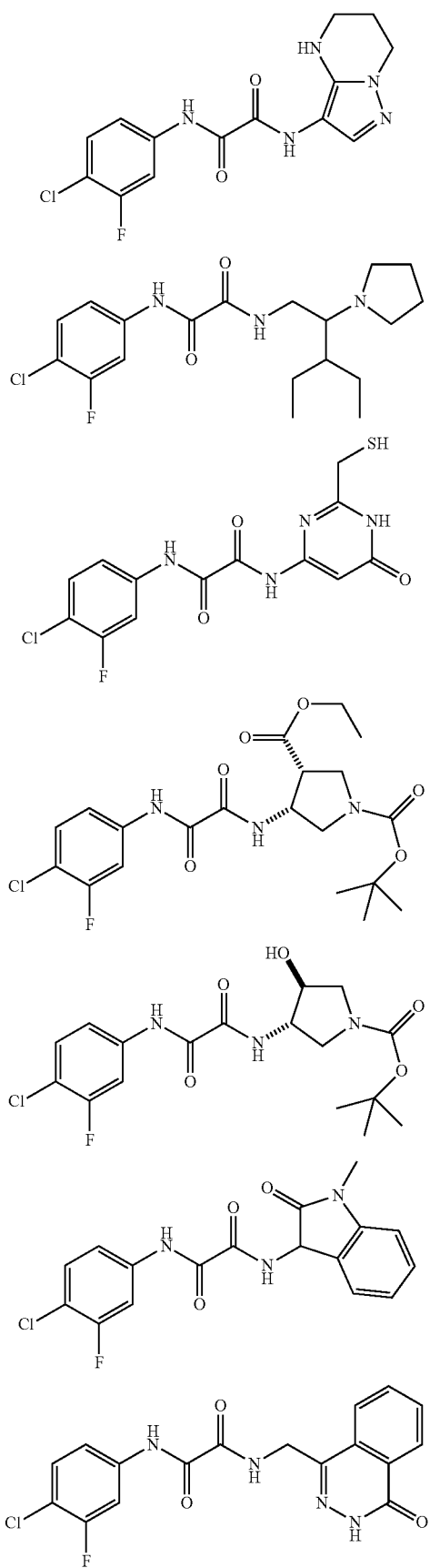
28
-continued
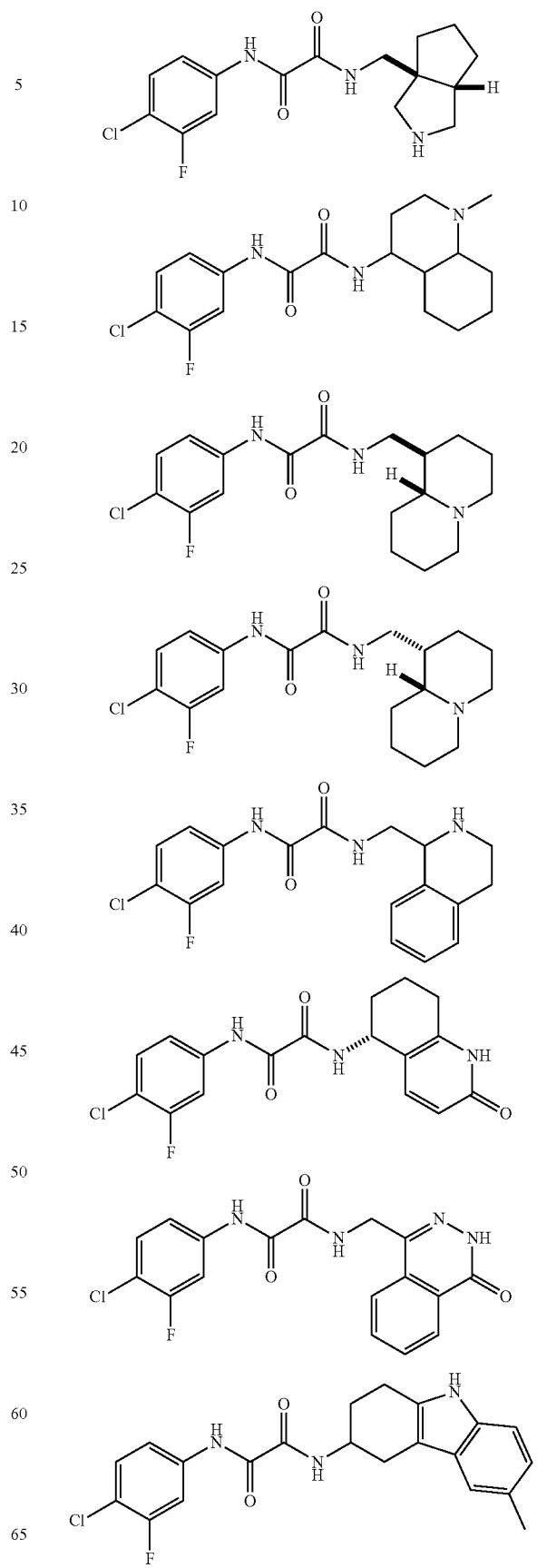

-continued
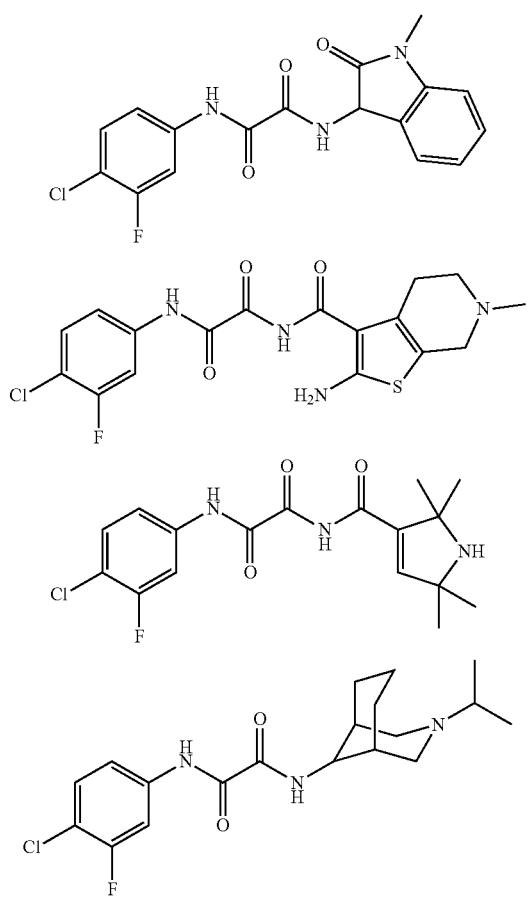
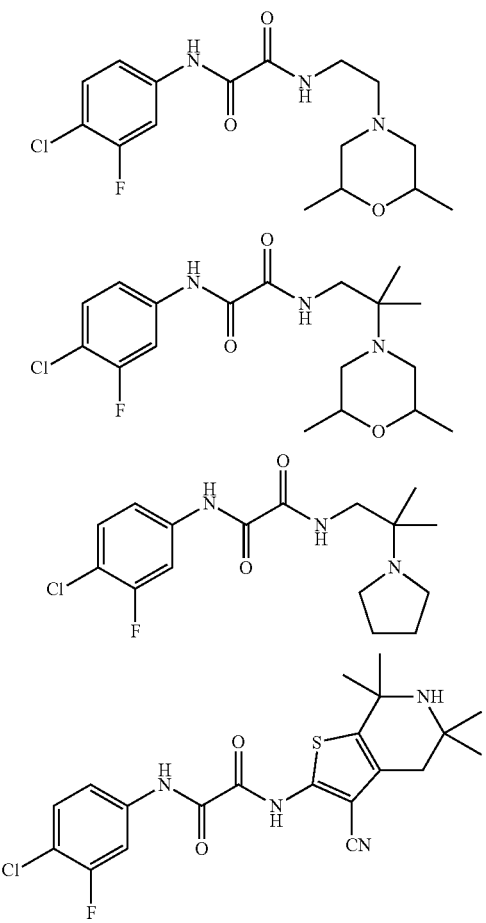
In certain embodiments, the invention provides a compound selected from the group consisting of:
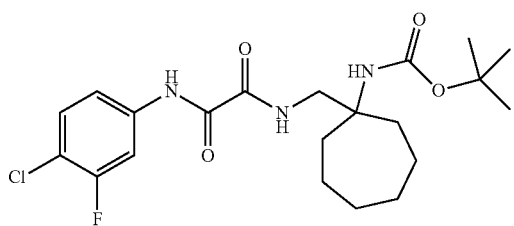
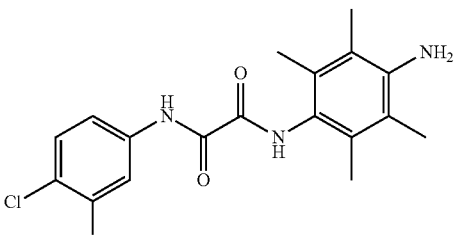
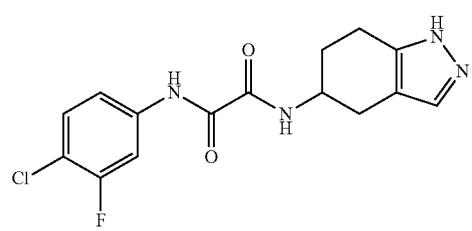
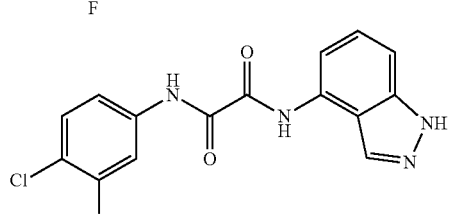
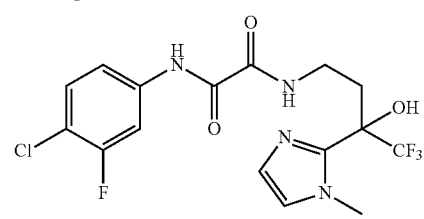
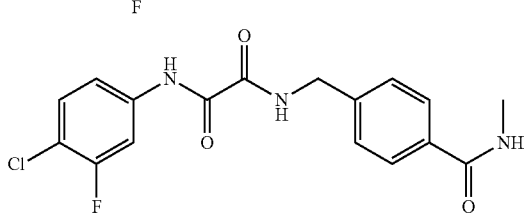

-continued
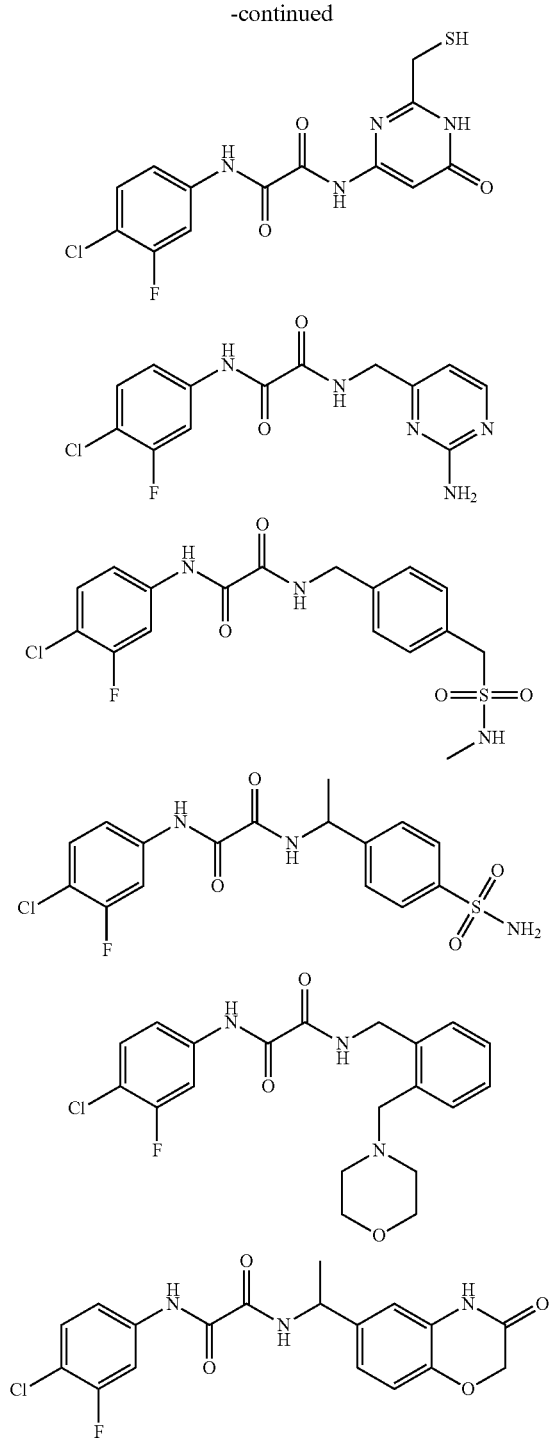
-continued
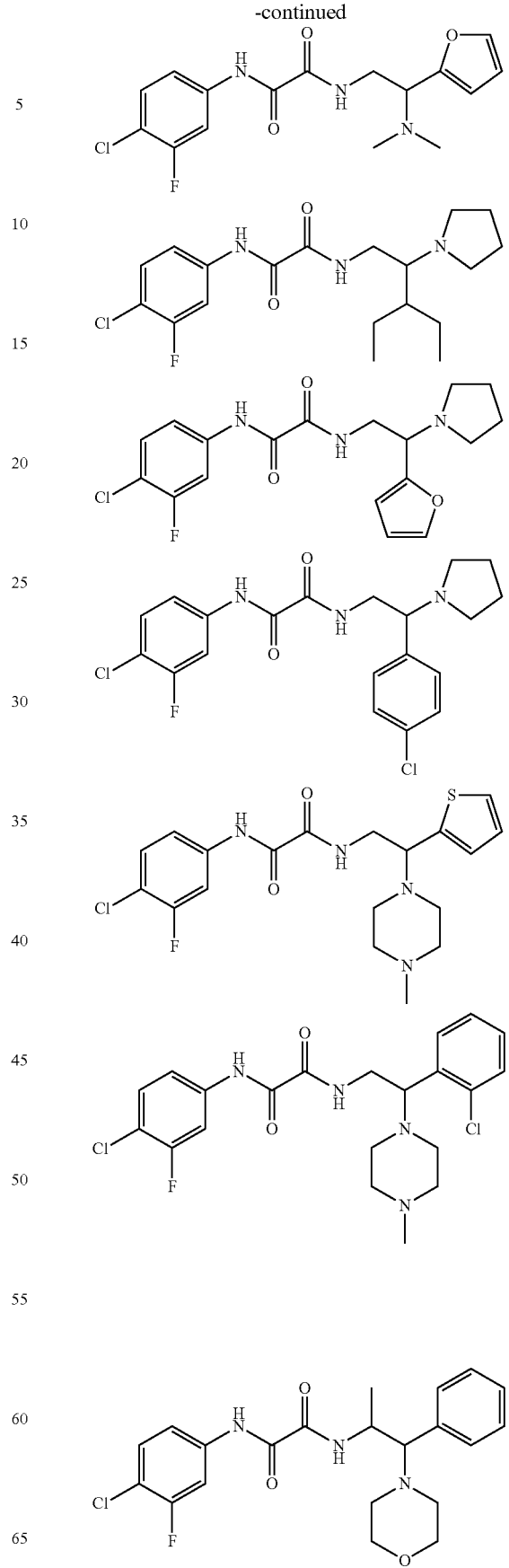

-continued

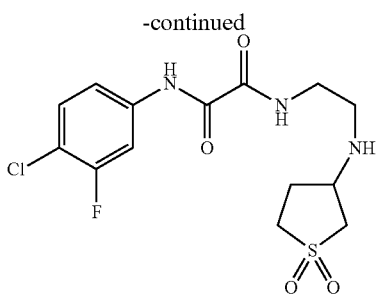

In a second embodiment, the invention provides a compound of formula IV:

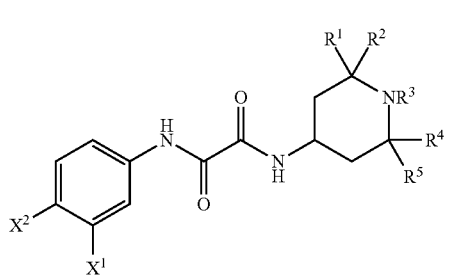

IV wherein $X^1$ is selected from the group consisting of halogen, methyl, and hydroxyl;
$X^2$ is a halogen;
$R^1$, $R^2$, $R^4$, and $R^5$ vary independently and are selected from the group consisting of hydrogen and alkyl groups any of which can be optionally substituted;
$R^3$ is a covalently-linked moiety capable of interacting with a virus expressing gp120;
and pharmaceutically acceptable salts thereof.

In certain embodiments, said moiety is a dendrimer capable of multivalent binding to said virus. In other embodiments, said moiety comprises a microbicide against said virus.

In another embodiment, the invention provides a method of activating HIV exterior envelope glycoprotein gp120 by binding gp120 with an effective amount of these compounds. As discussed above, and in further detail below, this activation can initiate a cascade of conformational changes that lead to loss of functional competence of gp120. As a consequence, the compounds of the present invention provide a mechanistic pathway for inhibition of viral transmission. This interference of viral transmission forms the basis for the development of prophylactic measures and/or treatment regimens against HIV infection.

While it is possible for compounds of the present invention to be administered as the raw chemical, it is also possible to present them as a pharmaceutical formulation. Accordingly, the present invention provides a pharmaceutical formulation comprising a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in Remington's Pharmaceutical Sciences. The pharmaceutical compositions of the present invention can be manufactured in a manner that is itself known, e.g., by means of conventional mixing, dissolving, granulating, dragee-making, levigating, emulsifying, encapsulating, entrapping or compression processes, for example.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route depends upon for example the condition and disorder of the recipient. The formulations can conveniently be presented in unit dosage form and can be prepared by any of the methods well known in the art. All methods include the step of bringing into association a compound of the present invention or a pharmaceutically acceptable salt, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the compounds of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compounds can also be formulated in rectal compositions such as suppositories or retention enemas, e.g., containing conventional suppository bases such as cocoa butter, polyethylene glycol, or other glycerides. The compounds can also be formulated in vaginal compositions as gels, suppositories, or as dendrimers conjugates.

Compounds of the present invention can be administered topically, that is by non-systemic administration. Formulations suitable for topical administration include liquid or semi-liquid preparations suitable for penetration through the skin such as gels, liniments, lotions, creams, ointments or pastes.

Gels for topical or transdermal administration of compounds of the present invention can include a mixture of volatile solvents, nonvolatile solvents, and water. The volatile solvent component of the buffered solvent system can preferably include lower ($C_1$-$C_6$) alkyl alcohols, lower alkyl glycols and lower glycol polymers. More preferably, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. Preferably, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound can crystallize due to evaporation of volatile solvent, while an excess will result in a lack of bioavailability due to poor release of drug from solvent mixture. The buffer component of the buffered solvent system can be selected from any buffer commonly used in the art; preferably, water is used. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions or liniments for application to the skin can also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They can be made by mixing the active ingredient in finely-divided or powdered form, alone or in solution or suspension in an aqueous or non-aqueous fluid, with the aid of suitable machinery, with a greasy or non-greasy base. The base can comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation can incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, can also be included.

The entry of human immunodeficiency virus type 1 (HIV) into target cells is mediated by the trimeric envelope glycoprotein (Env gp) complex, which consists of three gp120 exterior Env gps and three gp41 transmembrane Env gps. (Wyatt and Sodroski *Science* 280:1884-1888 (1998)). Binding of gp120 to the receptor, CD4, on the target cell surface induces conformational changes in the Env gps. (Myszka D G et al. *Proc. Natl. Acad. Sci. U.S.A.* 97:9026-9031 (2000)). These changes have been reported to allow gp120 to bind the viral co-receptor, either CXCR4 or CCR5 (Feng et al. *Science* 272:872-877 (1996); Dragic T et al. *Nature* 381: 667-673 (1996)) and also induce the formation of a gp41 pre-hairpin intermediate in which three hydrophobic grooves on the surface of a coiled coil formed by the heptad repeat 1 (HR1) region of gp41 are exposed. (Chan and Kim, *Cell* 93:681-684 (1998); Chan et al. *Proc. Natl. Acad. Sci. U.S.A.* 95:15613-15617 (1998)). These hydrophobic grooves can be occupied by helices from the gp41 heptad repeat 2 (HR2) region, during the formation of an energetically stable six-helix bundle that is hypothesized to drive the membrane fusion process. (Weissenhorn et al. *Nature* 387: 426-430 (1997)).

The soluble form of CD4 (sCD4) has been reported to provide opposing effects on HIV infectivity at different concentrations. At high concentrations, sCD4 neutralizes most HIV strains (Fisher et al. *Nature* 331:76-78 (1988)); at lower sCD4 concentrations, the infectivity of some HIV strains can be modestly enhanced. (Sullivan et al. *J. Virol.* 72:6332-6338 (1998)). This enhancing effect of sCD4 is more prominent in some strains of the related primate immunodeficiency viruses, HIV-2 and simian immunodeficiency virus (SIV), where sCD4 can replace cell-surface CD4 to drive infection of CD4⁻CCR5⁺ cells. (Schenten et al. *J. Virol.* 73:5373-5380 (1999); Clapham et al. *J. Virol.* 66:3531-3537 (1992)).

Mechanism of Action and Methods of Use

In one aspect, the invention provides a method of activating HIV exterior envelope glycoprotein gp120 comprising contacting HIV with an effective amount of a compound according to any one of formulae MB, to bind said gp120.

In another aspect, the invention provides a method of inhibiting transmission of HIV to a cell comprising contacting HIV with an effective amount of a compound according to any one of one of formulae I-IB to bind HIV exterior envelope glycoprotein gp120, thereby inhibiting transmission of HIV to said cell.

In various aspects, the invention provides a method of inhibiting the progression of HIV infection comprising contacting HIV with an effective amount of a compound according to any one of formulae I-IB to bind HIV exterior envelope glycoprotein gp120, thereby inhibiting progression of HIV.

In other aspects, the invention provides a method of inhibiting the transmission or progression of HIV to a cell comprising:

contacting HIV with an effective amount of a compound according to any one of formulae I-IB to bind HIV exterior envelope glycoprotein gp120; and contacting HIV with an effective amount of an exogenous ligand mimicking the chemokine receptor expressed on said cell.

In certain embodiments, the invention provides a method as described above, wherein is said chemokine receptor is selected from CCR5 and CXCR4.

In another aspect, the invention provides a method of inhibiting transmission of HIV to a cell comprising binding HIV exterior envelope glycoprotein gp120 with an effective amount of a compound according to formula IV.

In certain aspects, the invention provides a method of inhibiting progression of HIV comprising binding HIV exterior envelope glycoprotein gp120 with an effective amount of a compound according to formula IV.

Except for its lower affinity for the Env gps, compound II, as disclosed herein, exerted effects that were similar to those exerted by sCD4.

II

During the infection of CD4⁺ cells, compounds of the present invention compete for cell-associated CD4. In this context, some inhibition of infection results from the difference in the efficiency with which membrane-anchored CD4 and compounds of the present invention promote HIV attachment and entry. Compounds of the present invention also inhibit HIV infection by activation of the viral Env gps. The compounds of the present invention induce an activated state characterized by the exposure of the co-receptor binding on gp120 and the HR1 groove on gp41. Moreover, the Env gps activated by compounds of the present invention are able to mediate virus entry into CCR5⁺ cells lacking CD4. However, the activated intermediate mediated by compounds of the present invention decays rapidly; the rate is dependent upon temperature and Env gp strain. In the process, both exposure of the HR1 groove and membrane-fusing potential are lost.

Without being bound by theory, the exposure of the hydrophobic HR1 groove induced by compounds of the present invention is energetically unfavorable in the context of free virus, favoring a transition to a more stable but nonfunctional state. Despite rapid loss of function, the inactivated Env gps retained gp120, which remained associated with the compounds of the present invention and stably attached to the expressing cell surface.

The kinetics of the decay of HR1 groove exposure induced by compounds of the present invention and the decay of HIV infectivity correlate, and the ranges of concentrations of compounds of the present invention required for induction of the labile Env gp activated intermediate and for virus neutralization overlap. These observations indicate the contribution that induction of the metastable activated intermediate makes to inhibition of virus infectivity mediated by compounds of the present invention. Two properties of the HIV Env gps render them susceptible to this strategy of inhibition: 1) initial folding and assembly into a high-potential-energy form that is prone to transform into energetically more favorable states; and 2) triggering of these conformational transitions by receptor binding, allowing a receptor mimic to take advantage of the built-in propensity of the viral Env gp to engage the receptor.

The efficiency of an activation-based mechanism of inhibition is determined by the change over time in the distribution of the HIV Env gps among three states: 1) unliganded/non-activated; 2) bound/activated; and 3) post-activation decayed. This distribution is influenced by the following factors: 1) rate of engagement of the compounds of the present invention; 2) the time interval between activation induced by compounds of the present invention and progression to a step of infection that is unaffected by the decay process; and 3) the intrinsic stability of the activated intermediate.

Infection by cell-free virus is reported to be rate-limited by the slow diffusion-dependent attachment of the virus to the cell surface (Haim et al. *J. Virol.* 79:622-625 (2005); Andreadis S et al. *J. Virol.* 74:3431-3439 (2000). Under these conditions, activation of the diffusing virus by a compound of the present invention is characterized by an extended lag period between activation and the next step of the infection sequence. It has been reported that half-maximal productive adsorption of diffusing HIV virions to a cell monolayer (i.e., attachment that culminates in an infection event) occurs after approximately 5 hours at 37° C. (Haim et al. *J. Virol.* 81:3525-3534 (2007)). By contrast, the half-life of infectivity of the most stable activated intermediate demonstrated herein at 37° C. with compounds of the present invention was approximately 6 minutes. Because the longevity of the intermediate activated by compounds of the present invention is significantly shorter than the duration of the attachment step, inhibition of cell-free virus is primarily determined by the rate of activation (i.e. by both the on-rate and effective concentration of the compound).

Activating effects on HIV infection predominate at low concentrations of compounds of the present invention. In some embodiments, the stoichiometry of the compounds of the present invention binding to the HIV Env gp trimers can influence the propensity of the activated intermediate(s) to proceed along entry or post-activation decay pathways. For example, the binding of two equivalents of compounds of the present invention to the Env gp trimer can be beneficial for efficient inactivation/decay.

Retrovirus transmission has been reported to be more efficient when virus is transferred through direct physical interaction between cells (cell-cell transmission) rather than by diffusion of virions in cell-free transmission. (Dimitrov et al. *J. Virol.* 67:2182-2190 (1993)). Indeed, HIV that was pre-bound to the surface of CD4⁻CCR5⁺ cells, perhaps mimicking the conditions of cell-cell transmission, infected the cells efficiently after incubation with compounds of the present invention concentrations that were highly neutralizing for cell-free virus. During cell-cell transmission, where HIV virions emerging from the infected cell rapidly achieve proximity to the target cell, compounds of the present invention are more likely to enhance infection than in the case of cell-free infection.

In cell-cell transmission, the time interval between activation and the next step committed to the infection pathway exerts a dominant influence on the efficiency of HIV inhibition by compounds of the present invention. Several observations discussed herein indicate that the engagement of the co-receptor plays a major role in moving the activated HIV Env gps along the entry pathway. First, the sCD4-mediated enhancement of HIV infection of CD4⁻ cells is dependent on the level of CCR5 expression (see FIG. 5d). Second, activation of infection of CD4⁻CCR5⁺ cells by NBD-556 indicated a contribution of CCR5-binding affinity to susceptibility to enhancement. Finally, although compounds of the present invention allowed CCR5-using viruses to infect CD4⁻CCR5⁺ cells, they did not stimulate the infection of CD4⁻CXCR4⁺ cells by CXCR4-using viruses. The lack of enhancement of CXCR4-using viruses was not due to greater lability of the activated state. The half-lives of the sCD4-induced, HR1-groove-exposed state on the CXCR4-tropic HXBc2 Env gps was 55 minutes at 26° C., and was significantly longer on the dual-tropic KB9 Env gps.

Despite this, neither of these Env gps supported infection of CD4⁻CXCR4⁺ cells after incubation with sCD4 or compound II. However, compound II did allow viruses with the KB9 Env gps to infect CD4⁻CCR5⁺ cells. The apparent inability of viruses activated by compounds of the present invention to utilize CXCR4 for entry can be a consequence of the reported lower affinity of CXCR4 for the HIV Env gps, relative to that of CCR5 (Babcock et al. *J. Biol. Chem.* 276:38433-38440 (2001)). Together, these observations indicate a link between efficient co-receptor binding to the susceptibility of HIV to activation of infection of CD4⁻ cells induced by compounds of the present invention.

These results indicate that compounds of the present invention can be effective in settings, such as sexual transmission, in which HIV is dependent on diffusion for successful infection. Thus, the present invention provides a method of inhibiting transmission of HIV to a cell. The method includes contacting HIV with compounds of the present invention to bind the exterior envelope glycoprotein gp120. The compounds of the present invention activate gp120. Subsequent decay of this activated intermediate occurs at a rate sufficient to prevent HIV binding to the chemokine receptor of the cell being targeted by HIV, thereby inhibiting transmission by blocking viral entry. Thus, compounds of the present invention can be used as a prophylactic measure to prevent HIV infection.

Methods of inhibiting transmission of HIV can be used to inhibit any viral particle expressing an analogous gp120 envelope glycoprotein, including all strains of HIV-1 and HIV-2. This includes, for example, certain strains of simian immunodeficiency virus (SIV).

An effective amount of the compounds of the present invention for inhibiting transmission includes an amount that can establish a concentration between about 1 nm and about 1,000 μM in one embodiment, and between about 1 nM to about 250 μM in another embodiment. One skilled in the art will recognize that the exact amount can depend on a variety of factors including weight, age, sex. An effective amount of compounds of the present invention can include particular dosing regimens according to the pharmacokinetics/metabolism of the compounds being administered. One skilled in the art will recognize that dosing and quantities compound are also influenced by mode of administration, such as oral versus intravenous administration.

In other embodiments, the present invention provides a method of inhibiting the progression of HIV that includes contacting (exposing) HIV to an effective amount of compounds of the present invention binding HIV exterior envelope glycoprotein gp120. The compounds of the present invention can activate gp120 at a rate sufficient to prevent HIV binding to a chemokine receptor of a host cell to reduce the rate of progression of infection.

An effective amount of the compounds of the present invention for inhibiting progression includes an amount that can establish a concentration between about 1 nm and about 1,000 μM in one embodiment, and between about 1 nM to about 250 μM in another embodiment. Again, the exact amount can depend on a variety of factors including weight, age, sex. An effective amount of compounds of the present invention can include dosing regimens according to the pharmacokinetics/metabolism of the compounds and can also vary depending on the stage of infection when infection is already established. Dosing and quantities are also influenced by mode of administration, such as oral versus intravenous administration.

Further embodiments of the present invention provide method of inhibiting the transmission or progression of HIV to a cell by contacting HIV with an effective amount of compounds of the present invention to bind HIV exterior envelope glycoprotein gp120 in addition to providing an exogenous ligand for a chemokine receptor expressed on the target cell. chemokine receptor is selected from CCR5 and CXCR4. Ligands to inhibit these receptors are well known in the art, see for example, Donzella, et al. *Nat. Med.* 1998, January; 4(1):72-77; Dragic et al. *Proc. Natl. Acad. Sci. U.S.A.* 2000, May 9; 97(10): 5 639-644; Strizki et al. *Proc. Natl. Acad. Sci. U.S.A.* 2001 Oct. 23; 98(22): 12718-12723; and Tagat et al. *J. Med. Chem.* 2004, May 6; 47(10): 2 405-408, all of which are incorporated by reference herein in their entirety.

The results provided herein indicate the ability of small molecules to structure the conformationally flexible HIV gp120 glycoprotein. The favorable enthalpic changes (up to 24.5 kcal/mol) observed upon binding of compounds of the present invention are much larger than those values expected from the interaction of the compounds with gp120, as delineated in the docking model. The large enthalpy changes, which are partially compensated by large unfavorable entropy changes, are reminiscent of those changes observed during protein folding. (Robertson and Murphy *Chem. Rev.* 97:1251-1268 (1997).) The magnitude of the enthalpic change is consistent with the formation of a significant network of interactions within gp120 upon compound binding.

Moreover, some compounds of the present invention that vary in the phenyl ring substituents have similar affinities for gp120, yet exhibit enthalpy changes upon gp120 binding that differ by more than 10 kcal/mol. These observations indicate the formation of new interactions within gp120 and can account for the major portion of the favorable enthalpy changes associated with the binding of some of the compounds of the present invention.

The differences in the entropy changes associated with the binding of compounds of the present invention with subtly different para-phenyl substitutions indicate the importance of interactions with these two gp120 elements in inducing or stabilizing the CD4-bound conformation.

Analysis of the structure-activity relationships for compounds of the present invention correlates with the computer-modeled constraints on the size and polarity of the phenyl ring and oxalamide linker imposed by the nature of the Phe 43 pocket. Although more than 90 NBD-556-related compounds with alterations in these moieties were tested, only two related compounds, compound II and compound V, exhibited better gp120 binding than NBD-556 or NBD-557.

V

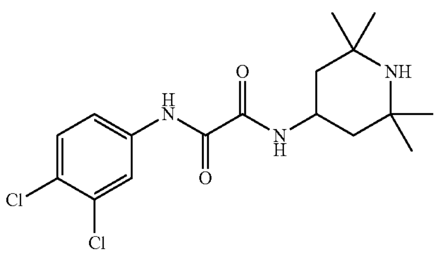

Both compound II and compound V have halogen groups at the para position and at one of the meta positions of the phenyl ring, indicating that asymmetric positioning of the compounds in the Phe 43 cavity is allowed and even favored. Asymmetric binding is supported by docking calculations, which indicate that the meta halogens in compound II and compound V are oriented towards gp120 loop B and β16, rather than towards the water channel that opens onto the opposing surface of the Phe 43 cavity.

Achieving affinity for gp120 is important, but not the only consideration for the ability of compounds of the present invention to promote CCR5 binding and HIV infection of $CD4^{-}CCR5^{+}$ cells or to establish their use as inhibitors of HIV infection. A series of compounds with various substituents in the para position of the phenyl ring bound comparably to gp120 yet exhibited a wide range of abilities to activate CCR5 binding or virus infection. Only by taking into account both the binding affinity and entropy changes could functional activation of the HIV envelope glycoproteins be accounted for. Likewise, compound II and compound V, which differ in the meta-phenyl substituent, exhibited similar affinities for gp120 and shared predicted binding modes; nonetheless, only compound II activated HIV infection of $CD4^{-}$ target cells. The magnitude of the entropy change is greater for compound II than for compound V, consistent with the dual importance of affinity and conformational fixation to the CD4-mimetic effects of these compounds. The magnitude of the unfavorable entropy change is much greater for compound II than for compound V, which would make compound II the weaker binder if the enthalpy changes for the two compounds were the same. Despite the large entropy penalty associated with the conformational fixation of gp120 upon binding of compound II, the larger favorable enthalpy change compensates for the unfavorable contribution which results in an overall higher affinity of compound II for gp120.

The results presented herein indicate that increasing the affinity of compounds of the present invention for gp120 correlates with improved antiviral efficacy. The relatively low molecular weight of compound II, which is optimized for insertion into the Phe 43 cavity, allowed further manipulation of the piperidine ring to achieve greater antiviral potency. Along these lines, the present invention provides a compound of formula III as well as compounds XVI-XVIII:

III

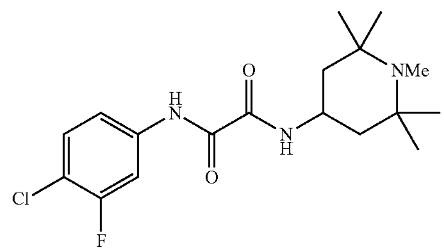

XVI

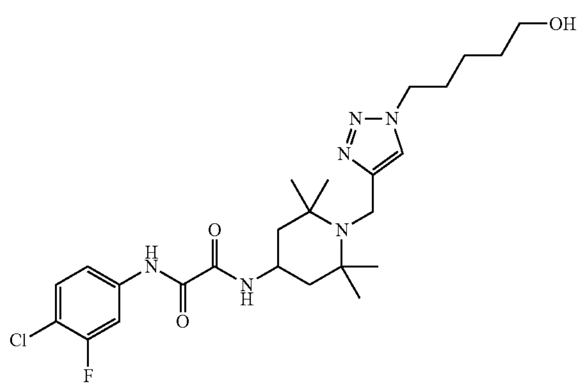

XVII

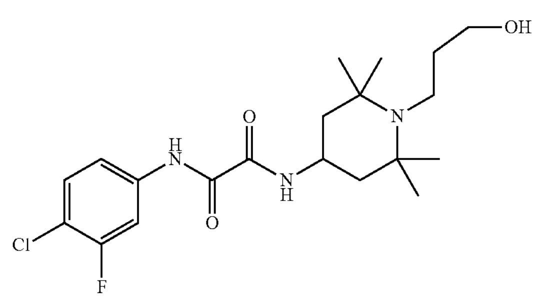

XVIII

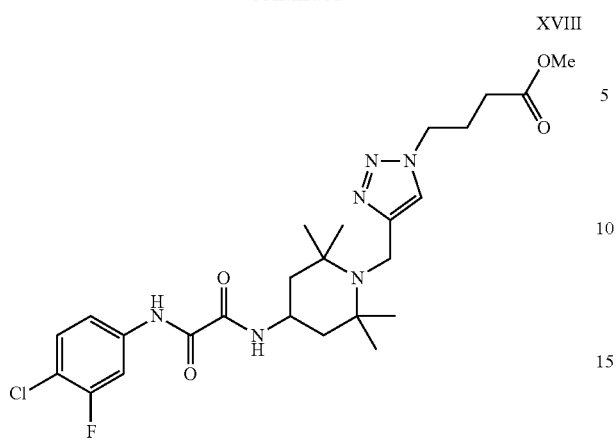

Compound III, which incorporates a methyl group on the piperidine nitrogen, exhibited a $K_d$ of 0.33 µM compared to 0.76 µM and 3.7 µM for compound II and NBD-556, respectively. Moreover, compound III exhibited inhibition of HIV with an $IC_{50}$ value of 75 µM, compared to 90 µM for compound II and >100 µM for NBD-556. For further discussion of the data for these compounds see the Examples below.

Further exemplary compounds of the present invention include the following:

XIX

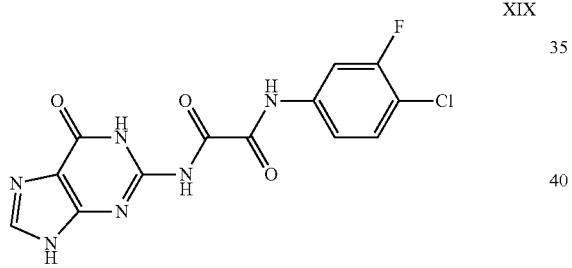

XX

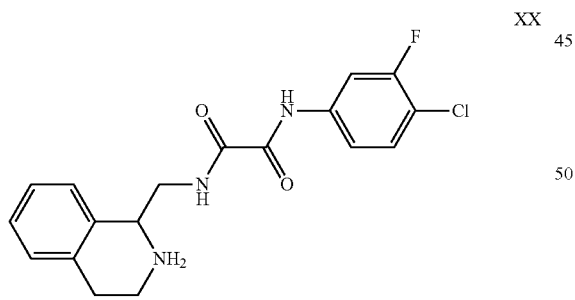

XXI

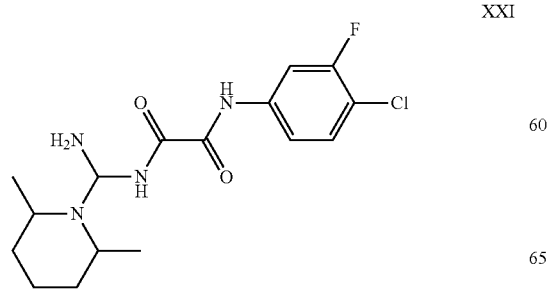

XXII

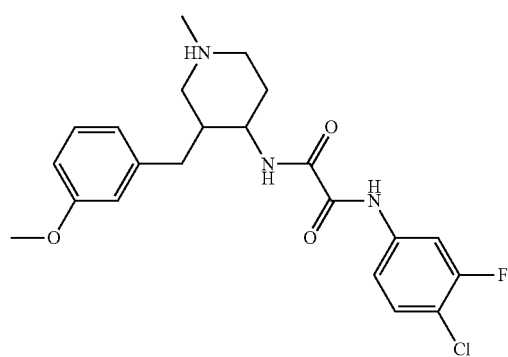

XXIII

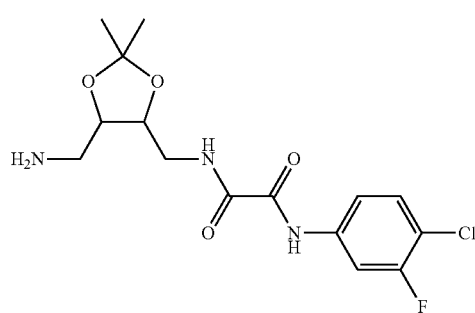

XXIV

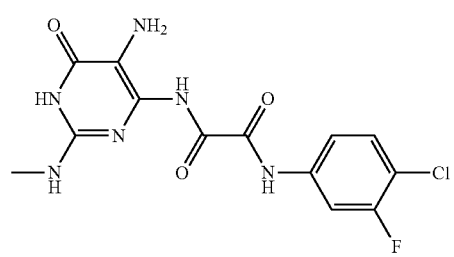

XXV

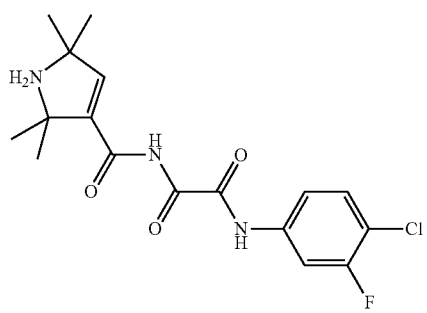

XXVI

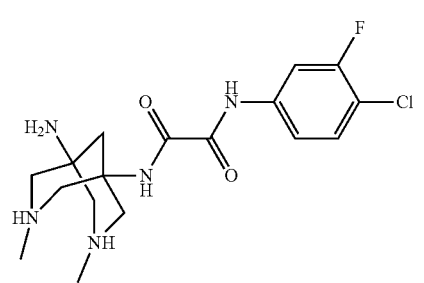

-continued

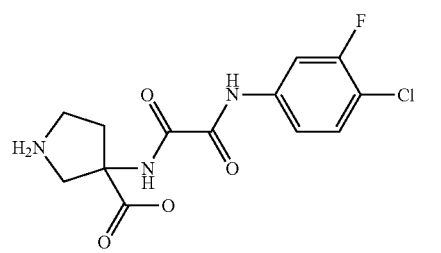
XXVII

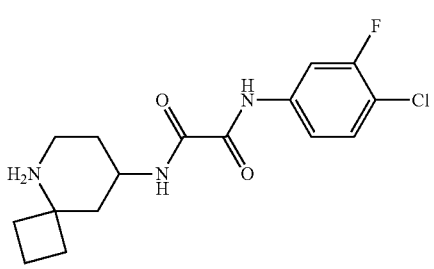
XXVIII

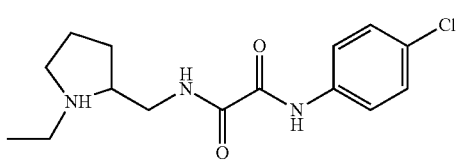
XXIX

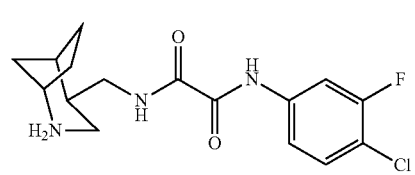
XXX

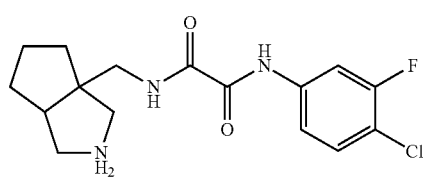
XXXI

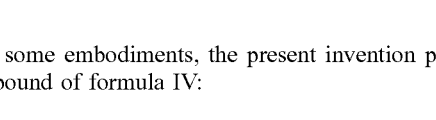

In some embodiments, the present invention provides a compound of formula IV:

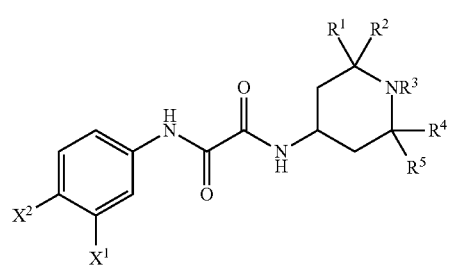
IV wherein X¹ is selected from the group consisting of halogen, methyl, and hydroxyl;
X² is a halogen;
R¹, R², R⁴, and R⁵ vary independently and are selected from the group consisting of hydrogen and alkyl groups any of which can be optionally substituted; and
R³ is a covalently-linked moiety capable of interacting with a virus expressing a gp120. This moiety can be a dendrimer capable of multivalent binding to HIV in some embodiments and can include dendrimers used to deliver a microbicide. Dendrimers have been used as carriers for drugs and microbicides. (See, for example, Heegaard et al. *Recent Patents Anti-Infect. Drug Disc.* 2006 November; 1(3): 331-351; Rupp et al. *Int. J. Nanomedicine* 2007 2(4): 561-566; and Cheng et al. *Front. Biosci.* 2008 Jan. 1; 13: 1447-1471, all of which are incorporated by reference in their entirety.)

Compounds of formula IV can be used in methods of inhibiting transmission and/or progression of HIV by binding HIV exterior envelope glycoprotein gp120. Additionally such compounds can, through subsequent, concomitant, or pr

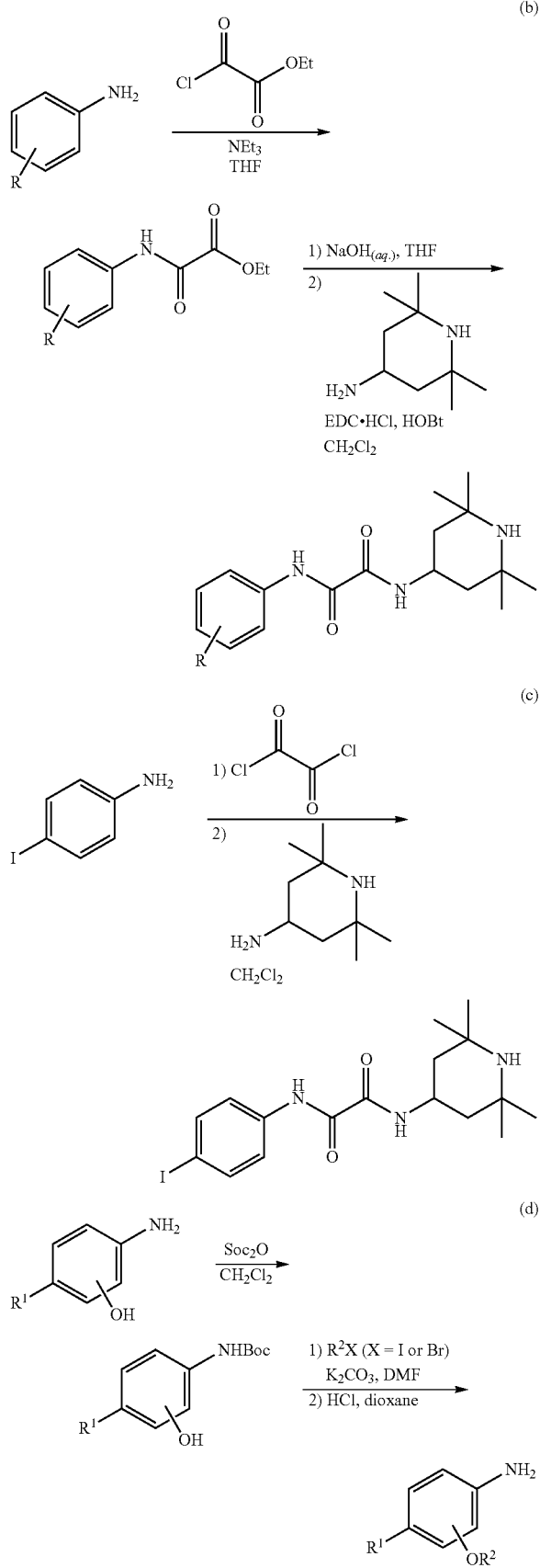

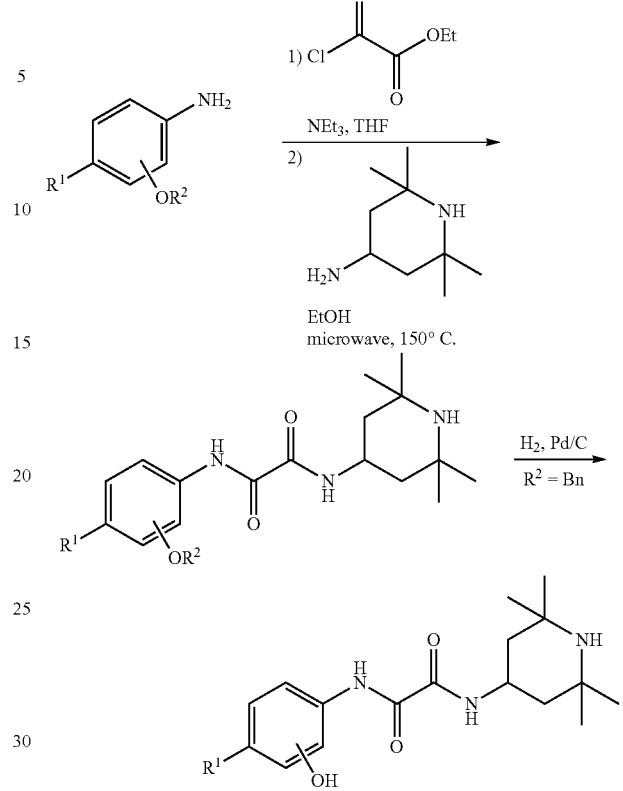

Modifications in region 1 can be accomplished by the general synthetic equations (a)-(d). Equation (a) shows the initial formation of an oxalamide ester by condensation of an aniline derivative with ethyl oxalyl chloride. Transamination of the ester at elevated temperature in the presence of microwave radiation provides the target NBD-556 analogues. An alternative route to this last step is given in equation (b), wherein the ester functionality of the oxalamide ester is first hydrolyzed with sodium hydroxide, followed by mild amide formation mediated by water soluble carbodiimide reagent EDC, catalyzed by hydroxybenzotriazole (HOBt).

Equations (c) shows a different approach wherein oxalyl chloride is reacted with the aniline derivative of interest in stoichiometric quantities, followed by condensation with the requisite amino substituted piperidine compound. Finally, where other functional groups that are potentially reactively with oxalyl chloride are present, protecting group manipulations can be necessary to provide the target analogues as shown in equation (d) which shows the synthesis of an analogue incorporating a phenol group in region 1.

Modifications in Region 2

Synthesis of Region 2 Analogues

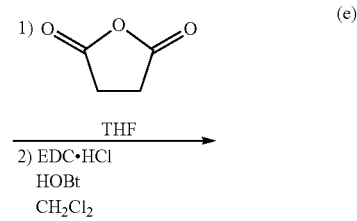

Modifications in Region 3

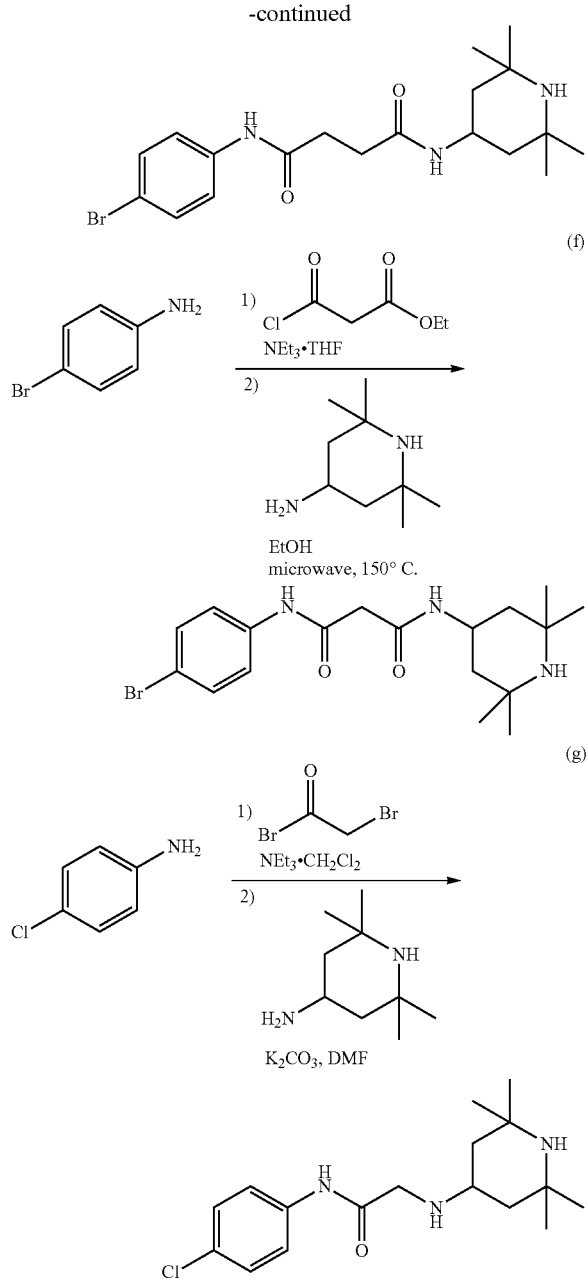

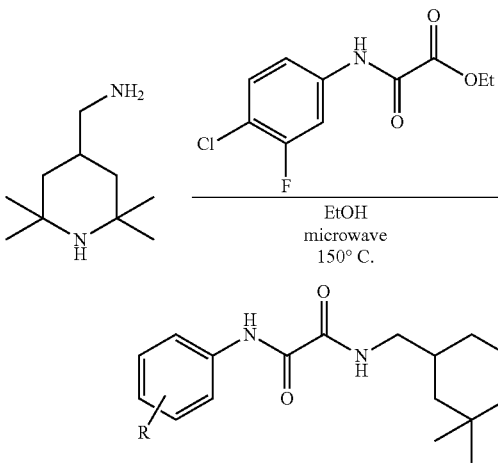

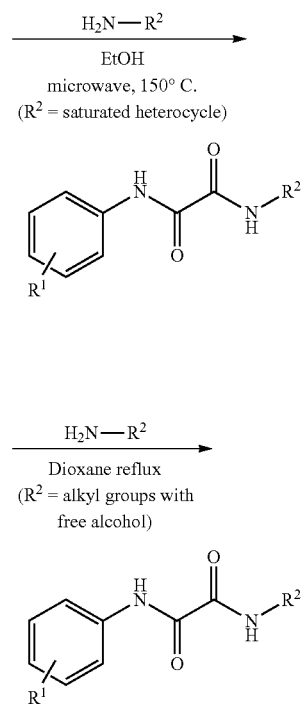

Modifications in the oxalamide linker are readily accessible as shown in equations (e)-(g). A two carbon insert between the oxalate carbonyls is readily achieved by condensation of the desired aniline derivative with succinic anhydride as shown in equation (e). The ring-opened anhydride can then be coupled to the amino-substituted piperidine using standard carbodiimide coupling conditions. Insertion of a single methylene unit between the oxalate carbonyls can be achieved by condensation of the desired aniline derivative with ethyl chloromalonate, as shown in equation (f). Microwave mediated transamination as described above can be used to complete the analogue synthesis. Equation (g) shows the removal of on of the carbonyl groups of oxalate by condensation of the desired aniline derivative with bromo acetyl bromide. Reaction of the acyl bromide with the aniline derivative, followed by bromide displacement with the amino-substituted piperidine provides the requisite product.

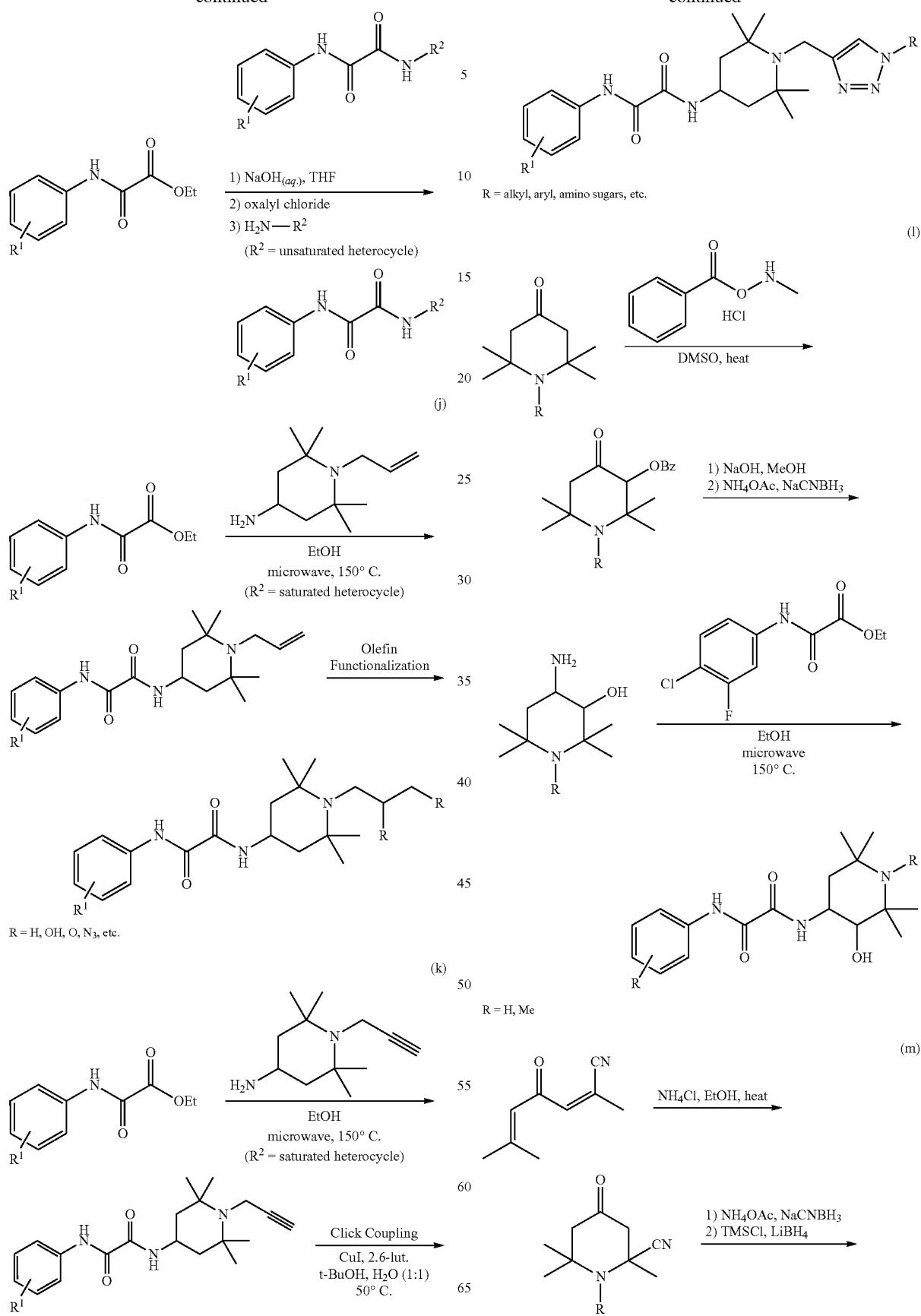

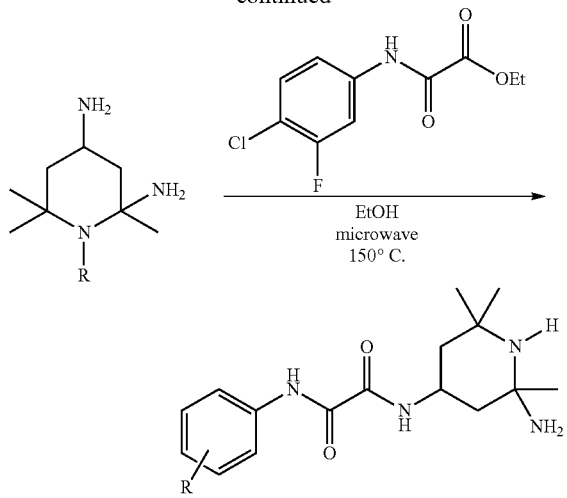

Numerous means are available to explore analogues in region 3 of the NBD-nucleus as shown in equations (h)-(m). The synthetic scheme in equation (h) shows the preparation of the homologous amino group on the piperidine moiety by condensation of 3-oxo-substituted tetramethylpiperidine with tosylmethyl isocyanide (TOSMIC), followed by lithium borohydride reduction to provide the requisite homologous amine. This amine is then coupled with the aniline-substituted oxalamide ester as previously described. The synthetic schemes of equation (i) show variations on a theme to completely swap out the piperidine moiety. Condensations with a variety of amines are shown including alkyl amines, saturated and unsaturated heterocycles under conditions previously described and known by those skilled in the art.

Equation (j) shows the synthetic scheme for the incorporation of an alkenyl group on nitrogen. The alkene product is a springboard for the preparation of any number of analogues off the piperidine nitrogen, including the diol, epoxide, and azido alcohol indicated in the scheme. Additionally, the alkene handle provides access to numerous sophisticated functionalizations under mild conditions tolerated by many biomolecules, such as olefin metathesis, [2+2] photocycloadditions, and [3+2] cycloaddition reactions, for example. The diol itself is viable precursor to an aldehyde, which can be used in reductive amination processes with sodium cyanoborohydride in the presence of an amine, including proteins having amino side-chain groups such as lysine. Such conjugation techniques are known by one skilled in the art. These chemistries can enable the attachment of dendrimers or microbicides as given in formula IV.

In a similar vein, access to the alkyne derivative shown in equation (k) provides many opportunities for conjugative chemistry for attachment of biomolecules. Equation (k) shows the attachment of a generic structure (R), for example, by so called "click chemistry." In equation (k) this step is the standard [3+2] cycloaddition reaction of the alkyne moiety with an azide.

Equation (l) shows the incorporation an extra hydroxyl group off the piperidine moiety. Such an analogue can benefit from additional hydrogen bonding in the Phe 43 cavity. The preparation commences by alpha benzoylation of 3-oxo tetramethylpiperidine. Hydrolysis of the ester and reductive amination of the ketone group provides the requisite amino alcohol for condensation with the aniline-substituted oxalamido ester.

Finally, equation (m) shows the replacement of one of the methyl groups of the tetramethylpiperidine moiety with an amino group. Like the hydroxyl substituted derivative described above, this derivative can also benefit by engaging in further hydrogen bonding motifs. The preparation commences by double Michael addition into a doubly alpha, beta-unsaturated ketone to provide a cyclized ketone product. Reductive amination of the ketone and reduction of the cyano moiety provides a diamino product for condensation with the aniline-substituted oxalamido ester.

The following exemplary compound preparations are provided to demonstrate methods described herein above.

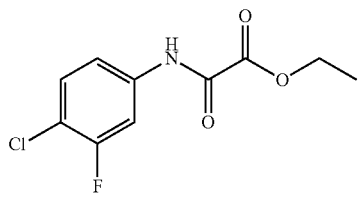 [SMILES: CCOC(=O)C(=O)Nc1ccc(Cl)c(F)c1]

Ethyl 2-(4-chloro-3-fluorophenylamino)-2-oxoacetate

To a solution containing para-chloro-meta-fluoroaniline (10.0 g, 70.1 mmol) in 600 mL THF at 0° C. was added $Et_3N$ (9.11 mL, 70.1 mmol) followed by ethyl oxalylchloride (7.70 mL, 70.1 mmol) dropwise over 15 minutes. The reaction mixture was warmed to room temperature and stirred for 18 hrs. The reaction mixture was filtered and the filter cake was washed with one-300 mL portion of ethyl acetate. The organic phase was washed with two-100 mL portions of 1M HCl, dried over $MgSO_4$, filtered, and concentrated to give the product. Recrystallization from hot $Et_2O$ gave the product as a colorless crystalline solid: yield 14.4 g (84%); $^1H$ NMR (500 MHz, $CDCl_3$): δ 1.43 (t, J=7.0 Hz, 3H), 4.42 (q, J=7.0 Hz, 2H), 7.25 (dq, J=8.5, 1.0 Hz, 1H), 7.37 (t, J=8.5 Hz, 1H), 7.72 (dd, J=10.5, 2.5 Hz, 1H), 8.94 (br, 1H).

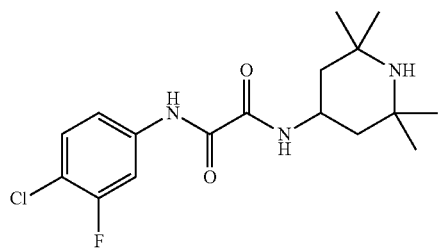 [SMILES: CC1(C)CC(NC(=O)C(=O)Nc2ccc(Cl)c(F)c2)CC(C)(C)N1]

N1-(4-Chloro-3-fluorophenyl)-N2-(2,2,6,6-tetramethylpiperidin-4-yl)oxalamide

To a solution containing ethyl 2-(4-chloro-3-fluorophenylamino)-2-oxoacetate (0.20 g, 0.81 mmol) in 2 mL EtOH in a microwave reaction vial which could be sealed with a Teflon® cap was added 2,2,6,6-tetramethyl-4-aminopiperidine (0.13 g, 0.81 mmol). The tube was briefly flushed with an Argon stream (approximately 30 s) and sealed. The reaction was heated to 150° C. for 1 hr in microwave and then allowed to cool to room temperature and stand for 12 hours, during which time a glassy solid formed. The solid was collected by filtration, washed with cold hexanes, and dried to give the product (JRC-II-191) as a colorless crystalline solid (pure as judged by HPLC-MS and ¹H NMR): yield 0.14 g (48%); ¹H NMR (500 MHz, CDCl₃): δ 1.07 (t, J=12 Hz, 2H), 1.16 (s, 6H), 1.28 (s, 6H), 1.57 (br, 1H), 1.92 (dd, J=12.7, 4 Hz, 2H), 4.26 (m, 1H), 7.23 (dd, J=14 Hz, 1.5 Hz, 1H), 7.38 (m, 1H), 7.70 (dd, J=10.5, 2.5 Hz, 1H), 9.31 (br, 1H). Note: 1 NH proton was not observed in CDCl₃. MS: [M+H]⁺=356.16 Da.

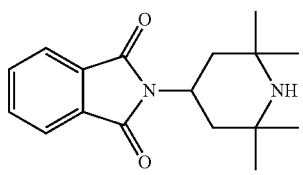 [SMILES: CC1(C)CC(N2C(=O)c3ccccc3C2=O)CC(C)(C)N1]

2-(2,2,6,6-Tetramethylpiperidin-4-yl)isoindoline-1,3-dione

To a solution containing 2,2,6,6-tetramethylpiperidin-4-amine (10.0 g, 63.9 mmol) in 50 mL of AcOH was added phthalic anhydride (9.47 g, 63.9 mmol). The reaction mixture was heated to reflux for 2 hr at which time it was cooled and the most of the AcOH was removed by azeotrope with toluene. The residue was diluted with CH₂Cl₂ and treated with sat. aq. NaHCO₃ until aqueous layer was pH=8. The aqueous phase was then extracted with three-100 mL portions of CH₂Cl₂, dried over MgSO₄, filtered, and concentrated to give the product as a colorless crystalline solid: yield 15.55 g (85%); ¹H NMR (500 MHz, CDCl₃): δ 1.18 (s, 6H), 1.30 (s, 6H), 1.64 (dd, J=12.5, 3.5 Hz, 2H), 2.10 (t, J=12.5 Hz, 2H), 4.68 (tt, J=13.0, 4.0 Hz, 1H), 7.70-7.71 (m, 2H), 7.81-7.82 (m, 2H).

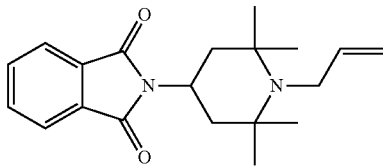 [SMILES: C=CCN1C(C)(C)CC(N2C(=O)c3ccccc3C2=O)CC1(C)C]

2-(1-Allyl-2,2,6,6-tetramethylpiperidin-4-yl)isoindoline-1,3-dione

A solution containing 2-(2,2,6,6-tetramethylpiperidin-4-yl)isoindoline-1,3-dione (1.00 g, 3.49 mmol) and tetrabutylammonium iodide (0.13 g, 0.35 mmol) in 2 mL of allyl bromide was heated to 130° C. in a sealed tube for 18 hr. The reaction was cooled and quenched with 20 mL sat. aq. NaHCO₃. The aqueous phase was extracted with three-20 mL portions of CH₂Cl₂, dried over MgSO₄, filtered, and concentrated to give the crude product. The residue was purified by flash chromatography on SiO₂ (15×2 cm). Elution with 3:1 hexanes:ethyl acetate gave the product as a colorless solid: yield 0.41 g (40%); ¹H NMR (500 MHz, CDCl₃): δ 1.10 (s, 6H), 1.13 (s, 6H), 1.51-1.54 (m, 2H), 2.45 (t, J=2.5 Hz, 2H), 3.16-3.17 (m, 2H), 4.59 (tt, J=13.1, 3.5 Hz), 4.94 (dd, J=10.2, 1.9 Hz, 1H), 5.19 (dd, J=17.2, 1.9 Hz, 1H), 5.83-5.90 (m, 1H), 7.68-7.70 (m, 2H), 7.79-7.82 (m, 2H).

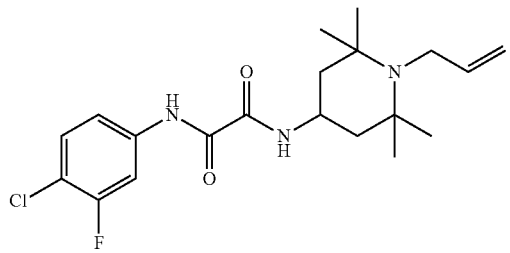 [SMILES: C=CCN1C(C)(C)CC(NC(=O)C(=O)Nc2ccc(Cl)c(F)c2)CC1(C)C]

N1-(1-Allyl-2,2,6,6-tetramethylpiperidin-4-yl)-N2-(4-chloro-3-fluorophenyl)oxalamide To a solution containing 2-(1-allyl-2,2,6,6-tetramethylpiperidin-4-yl)isoindoline-1,3-dione (0.29 g, 0.89 mmol) in 9 mL of ethanol was added hydrazine hydrate (0.28 mL, 8.9 mmol). The reaction mixture was stirred at reflux for 40 min. and cooled to room temperature. The solution was filtered and washed with 20 mL diethyl ether and concentrated to give product which was used without further purification in the microwave coupling reaction above to give the product as a colorless solid 0.23 g (66%); ¹H NMR (500 MHz, CDCl₃): δ 1.02 (s, 6H), 1.05 (s, 6H), 1.50-1.59 (m, 4H), 3.13-3.14 (m, 2H), 4.07-4.14 (m, 1H), 4.91 (dd, J=10.5, 2.0 Hz, 1H), 5.15 (dd, J=17.0, 2.0 Hz, 1H), 5.78-5.85 (m, 1H), 7.57 (t, J=9.0 Hz, 1H), 7.70 (dd, J=8.5, 1.5 Hz, 1H), 7.92 (dd, J=12.0, 2.5 Hz, 1H), 8.83 (d, J=8.5 Hz, 1H), 10.93 (s, 1H).

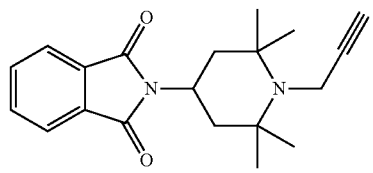 [SMILES: C#CCN1C(C)(C)CC(N2C(=O)c3ccccc3C2=O)CC1(C)C]

2-(2,2,6,6-Tetramethyl-1-(prop-2-ynyl)piperidin-4-yl)isoindoline-1,3-dione

A solution containing 2-(2,2,6,6-tetramethylpiperidin-4-yl)isoindoline-1,3-dione (3.00 g, 10.5 mmol) and tetrabutylammonium iodide (0.42 g, 1.05 mmol) in propargyl bromide (6 mL-80% solution in toluene) was heated to 130° C. in a sealed tube for 35 min. The reaction was cooled and quenched with 20 mL sat. aq. NaHCO₃. The aqueous phase was extracted with three-20 mL portions of CH₂Cl₂, dried over MgSO₄, filtered, and concentrated to give the crude product. The residue was purified by flash chromatography on SiO₂ (15×2 cm). Elution with 3:1 hexanes:ethyl acetate gave the product as a colorless solid: yield 1.36 g (40%); ¹H NMR (500 MHz, CDCl₃): δ 1.13 (s, 6H), 1.25 (s, 6H), 1.47-1.50 (m, 2H), 2.10 (t, J=2.0 Hz, 1H), 2.46 (t, J=12.5 Hz, 2H), 3.32 (d, J=2.5 Hz, 2H), 4.54 (tt, J=13.0, 3.5 Hz, 1H), 7.65-7.67 (m, 2H), 7.75-7.77 (m, 2H).

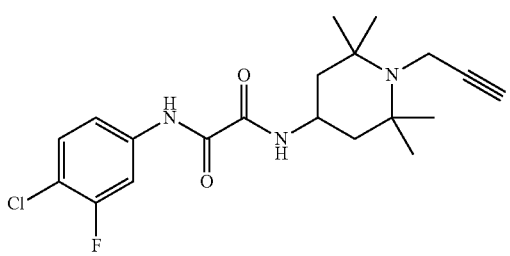 [SMILES: C#CCN1C(C)(C)CC(NC(=O)C(=O)Nc2ccc(Cl)c(F)c2)CC1(C)C]

N1-(4-Chloro-3-fluorophenyl)-N2-(2,2,6,6-tetramethyl-1-(prop-2-ynyl)piperidin-4-yl)oxalamide To a solution containing 2-(2,2,6,6-tetramethyl-1-(prop-2-ynyl)piperidin-4-yl)isoindoline-1,3-dione (11.9 g, 36.7 mmol) in 370 mL of ethanol was added methylhydrazine (19.3 mL, 367 mmol). The reaction mixture was stirred at reflux for 5 hr. and cooled to room temperature. The solution was filtered and washed with 200 mL diethyl ether and concentrated to give product which was used without further purification in the microwave coupling reaction above to give the product as a colorless solid 5.54 g (40%); $^1$H NMR (500 MHz, CDCl$_3$): δ 1.04 (s, 6H), 1.15 (s, 6H), 1.50-1.56 (m, 4H), 2.85 (t, J=2.5 Hz, 1H), 2.90 (d, J=2.0 Hz, 2H), 4.04-4.13 (m, 1H), 7.56 (t, J=8.5 Hz, 1H), 7.70-7.72 (m, 1H), 7.92 (d, J=11.5, 2.0 Hz, 1H), 8.88 (d, J=3.5 Hz, 1H), 10.93 (s, 1H).

It is understood that modifications which do not substantially affect the activity of the various embodiments of this invention are also included within the definition of the invention provided herein. Accordingly, the following examples are intended to illustrate but not limit the present invention.

Example I

General Experimental for Biological Data

This example provides general assay procedures used in Examples II-XVIII.

Plasmids expressing HIV envelope glycoproteins. The wild-type and mutant HIV envelope glycoproteins were expressed from the pSVlllenv vector. The glycoprotein mutants were created by site-directed mutagenesis, as previously described. (Kunkel et al., Meth. Enzymol. 1987 154: 367-382; Olshevsky et al. J. Virol. 64:5701-5707 (1990); Xiang et al. "Mutagenic stabilization and/or disruption of a CD4-bound state reveals distinct conformations of the human immunodeficiency virus type 1 gp120 envelope glycoprotein," J. Virol. 76:9888-9899 (2002)). The residue numbering is based upon that of the prototypic HIV$_{HXBc2}$ envelope glycoproteins, according to current convention (Korber et al., Hum. Retroviruses AIDS III-102, (1998)). The env genes of the mutated plasmids were sequenced to verify the presence of the desired mutation and the absence of unwanted changes. The mutants are designated by the following nomenclature: wild-type amino acid in single-letter code, residue number, and amino acid to which the residue has been changed.

Recombinant luciferase viruses: Using the Effectene transfection reagent (Qiagen), 293T human embryonic kidney cells were cotransfected with plasmids expressing the pCMVΔP1ΔenvpA HIV Gag-Pol packaging construct, the wildtype or mutant HIVYU2 envelope glycoproteins or the envelope glycoproteins of the control amphotropic murine leukemia virus (A-MLV), and the firefly luciferase expressing vector at a DNA ratio of 1:1:3 μg. For the production of viruses pseudotyped with the A-MLV glycoprotein, a rev expressing plasmid was added. The single-round, replication-defective viruses in the supernatants were harvested 24-30 hours after transfection, filtered (0.45 μm), aliquoted, and frozen at −80° C. until further use. The reverse transcriptase (RT) activities of all viruses were measured as described previously (Rho et al., Virology 112: 355-360 (1981)).

Radiolabeling of the gp120 glycoprotein: Approximately 3.5×10$^6$ 293T cells were seeded in a T75 tissue culture flask one day before transfection. Cells were cotransfected with 9 μg of pSVIIIEnv expressing the full-length HIVYU2 envelope glycoproteins and 1 μg of pLTR-Tat using the Polyfect transfection reagent (Qiagen). One day after transfection, the cells were labeled for 48 hours with [$^{35}$S]-Express protein labeling mix (30 μCi/mL) (Perkin-Elmer). The supernatant was harvested 48 hours later, cleared by centrifugation at 2,000 rpm for 5 minutes, and stored at 4° C. The amount of labeled gp120 was quantitated by immunoprecipitation with a mixture of sera from HIV-infected individuals and protein A-Sepharose beads (Amersham Bio-Sciences), followed by SDS-PAGE and autoradiography.

gp120-CCR5 binding assay: Cf2Th cells expressing high levels of CCR5 were lifted using 5 mM EDTA, pH 7.5. The cells were washed with serum-free DMEM, added to microcentrifuge tubes (2–3×10$^6$ cells/tube), and incubated with 500 μL of radiolabeled HIVYU2 gp120 in the absence or presence of varying concentrations of sCD4 or NBD-556 at 37° C. for 1.5 hours with gentle agitation. The supernatants were removed following incubation and the cells were washed twice with cold DMEM before lysis in 0.5 mL of IP buffer containing 0.5 M NaCl, 10 mM Tris, pH 7.5, 0.5% [vol/vol] NP40 and a cocktail of protease inhibitors.

The cells were incubated in IP buffer for 30 minutes at 4° C. with gentle agitation. The lysates were cleared by centrifugation at 14,000×g for 30 minutes at 4° C. Bound gp120 was precipitated by a mixture of sera from HIV-infected individuals and protein A-Sepharose beads and visualized by autoradiography of a 3-8% SDS-polyacrylamide gel.

Production and purification of the HIV gp120 glycoprotein: The wild-type gp120 and gp120 variants with C-terminal (His)$_6$ epitope tags were expressed from plasmids containing a codon-optimized (Genescript) env gene. Plasmids expressing codon-optimized gp120 glycoproteins were transfected into 293F cells using 293fectin reagent (Invitrogen) according to the manufacturer's protocol. Seven days later the supernatant expressing the envelope glycoproteins was harvested and filtered using 0.45 μm filters. The supernatant was concentrated 2-3-fold using Centricon plus-80 (Amicon) filters. Ni-NTA beads (Qiagen) were added to the concentrated supernatant and incubated overnight at 4° C. with gentle shaking. The supernatant/bead mixture was poured into a small column, washed with 20 mM imidazole in buffer A (150 mM NaCl, 20 mM Tris-HCl, pH 7.4), and eluted by gravity flow with 200 mM imidazole in buffer A. The eluant was concentrated with Centriprep-30 (Amicon) and dialyzed with a 10K-cutoff dialysis cassette (Pierce) in 20 mM Tris-HCl, pH 7.4 and 150 mM NaCl.

Production and purification of the HIV gp120 core protein: The gp120 core protein from HIVYU2 (Kwong et al. "Structures of HIV gp120 envelope glycoproteins from laboratory-adapted and primary isolates," Structure 8:1329-1339 (2000)) was expressed in Drosophila Schnieder 2 cells under the control of an inducible metallothionein promoter. The secreted gp120 core protein was purified by affinity chromatography with the F105 antibody covalently coupled to Sepharose. Following extensive washing with phosphate-buffered saline containing 0.5 M NaCl, the gp120 core protein was eluted with 0.1 M glycine, pH 2.8, followed by immediate neutralization with Tris buffer. After spin concentration with Centriprep 30 filters (Amicon), the gp120 core protein was dialyzed into phosphate-buffered saline and stored at −20° C. in aliquots.

Compound binding assay: BioSpin columns (Bio-Rad) capable of separating low-molecular-weight compounds from large macromolecules were used to measure the binding of [$^3$H]-NBD-556 or [$^3$H]-BMS-806 (ViTrax Radiochemicals, Placentia, Calif.) to the HIV gp120 envelope glycoprotein. Mixtures (70-90 μL) containing purified HIV gp120 in phosphate-buffered saline (PBS) and [$^3$H]-NBD-556 or [$^3$H]-BMS-806 were incubated for 15-30 minutes at 37° C., applied to a BioSpin column, and centrifuged for 2 minutes at 1200 rpm. The eluate was collected and counted in an LS6500 Multi-Purpose Scintillation Counter (Beckman Coulter).

Optical biosensor binding assay: Optical biosensor (Biacore, Inc.) analysis of the binding of NBD-556 to the HIVYU2 gp120 core bound to the 17b antibody was carried out as described previously. (Zhang et al. "Conformational changes of gp120 in epitopes near the CCR5 binding site are induced by CD4 and a CD4 miniprotein mimetic," *Biochemistry* 38:9405-9416 (1999).) Standard amine coupling was used to immobilize the 17b antibody to CM5 sensor chips at a surface density of approximately 500 response units. The gp120 core protein (200 nM) in the presence of variable concentrations of NBD-556 was passed over the modified sensor chip at 30 μL/min for 5 minutes, followed by a 5-min dissociation phase. Sensorgrams were analyzed using global fitting with BIAevaluation 4.1 software.

Isothermal titration calorimetry: Isothermal titration calorimetric experiments were performed using a high-precision VP-ITC titration calorimetric system from MicroCal Inc. (Northampton, Mass.). The calorimetric cell (~1.4 mL), containing wild-type or mutant gp120 dissolved in PBS (Roche Diagnostics GmbH), pH 7.4 with 2% DMSO, was titrated with the different inhibitors dissolved in the same buffer. The concentration of gp120 was ~3 μM and the concentration of inhibitor in the injection syringe was between 100 and 150 μM. Binding of Mab 17b to core gp120 was studied by stepwise injections of 20 μM 17b to the calorimetric cell containing 3 μM core gp120 by itself or equilibrated with 600 μM NBD-556. Binding of NBD-556 to core gp120 in complex with 17b was studied by titration of 3 μM core gp120 with 20 μM 17b and 300 μM NBD-556, in sequence. The heat evolved upon injection of the inhibitors was obtained from the integral of the calorimetric signal. The heat associated with the binding reaction was obtained by subtracting the heat of dilution from the heat of reaction. The individual heats were plotted against the molar ratio, and the values for the enthalpy change (ΔH) and association constant ($K_a = 1/K_d$) were obtained by nonlinear regression of the data. All experiments were carried out at 25° C.

Modeling the binding of NBD-556 and its analogues to HIV gp120:

Small Molecule Preparation.

Molecules were constructed in MOE (MOE Molecular Operating Environment Chemical Computing Group, version 2005.06 (Montreal, Canada) (on the world wide web at chemcomp.com), ionized using MOE's WashMDB function, and hydrogens were added. The small molecule conformation was minimized to a gradient of 0.01 in the MMFF94x (Halgren, T. A., *J. Comput. Chem.* 20, 1999, 720-729; Halgren, T. A. *J. Comput. Chem.* 20, 1999, 740-774) force field using a distance-dependent dielectric constant of 1.

Protein preparation. Using the x-ray crystal structure of the CD4-bound HIV gp120 core (PDB code 1 G9M), hydrogen atoms were added and tautomeric states and orientations of Asn, Gln and His residues were determined with Molprobity (on the world-wide web at molprobity.biochem.duke.edu, Word, J. M. et al. *J. Mol. Biol.* 1999, S. C. Lovell, et al., *Proteins: Structure, Function and Genetics* 50, 437-450, 285, (2003) 1735-1747). Hydrogens were added to crystallographic waters using MOE (MOE, 2005). The OPSLAA (Jorgensen W L et al. *J. Am. Chem. Soc.* 117 (1996) 11225-11236.) force field in MOE was used and all hydrogens were minimized to an rms gradient of 0.01, holding the remaining heavy atoms fixed. A stepwise minimization followed for all atoms, using a quadratic force constant (100) to tether the atoms to their starting geometries; for each subsequent minimization, the force constant was reduced by a half until 0.25. This was followed by a final cycle of unrestrained minimization.

Docking calculations. Glide(4.018) Water, isopropanol, fucose and n-acetyl D-glucosamine molecules were removed from the coordinates of the minimized protein (1G9M) as described above. The protein was then passed through the protein preparation utility in Glide (Friesner et al. *J. Med. Chem.* 47:1739-1749 (2004); Halgren et al. *J. Med. Chem.* 1750-1759 (2004)) using the OPSLAA (Jorgensen et al., supra) force field and using a water solvation model with extended cutoffs. All heavy atoms were constrained with a parabolic potential of 100 kJ/A. One-hundred iterations of Polak-Ribiere conjugate gradient (PRCG) minimization were applied. The binding site was defined based on the positions of CD4 Phe 43 and the isopropanol molecule from the 1 G9M crystal structure. The Glide grids were computed with a box center at 28.10, −12.35, 81.57 and an inner and outer box range of 14 Å and 36 Å, respectively. Docking calculations were performed in standard sampling mode with maxkeep 5,000 and maxref 1,000.

Gold (version 3.2). The binding site was defined by using the docked conformation of NBD-556 produced with Glide. Docking calculations were performed with crystallographic water molecules in the cavity. Analysis of initial docking calculations with all six water molecules (HOH 6, HOH 77, HOH 134, HOH 313, HOH 327 and HOH 343) toggled on and off during docking and the estimated free energy of binding in Gold indicated that three crystallographic waters behaved as integral parts of the protein (HOH 6, HOH 327 and HOH 343) and three were likely to be displaced (HOH 77, HOH 134 and HOH 313). Water HOH 6 forms a bridging hydrogen bond between the backbone carbonyls of Gly 473 and Trp 427, HOH 343 forms a bridging hydrogen bond between Val 425 and Asn 377, and HOH 327 hydrogen bonds with Ser 375 in the base of the cavity. Subsequent docking calculations were performed with HOH 343 left on while waters HOH 6 and HOH 327 were turned on with hydrogen atoms spun. One hundred genetic algorithm (GA) docking runs were performed with the following parameters: initial virtual_pt_match_max=3.5, diverse_solutions=1, divsol_cluster size=1, and divsol_rmsd=1.5. All other parameters were set as defaults.

ROCS Virtual Screening:

Flipper from Open Eye was used to expand compounds with unspecified chirality prior to generation of conformers. Using Omega (version 2.2.1) from Open Eye with default parameters, a maximum of 50 lowenergy conformers for all compounds in the Zinc Database (version 7) were generated and stored in sd files of approximately 10,000 molecules. ROCS searches were run using 3D coordinates from the docked binding mode of the teramethyl-piperidine portion of JRC-II-191. The Implicit Mills Dean forcefield was used to match chemotypes as well as shape. A maximum of 2000 hits were saved for each query and were ranked by a combination of Tanimoto and the scaled Color Score (ComboScore). Primary amines were selected from the set of hits, conjugated in silico and were docked with Gold and scored with a masscorrected Goldscore. Compounds that reiterated the binding mode of the Fl-Cl-phenyl oxalamide moiety of JRC-II-191 were considered for purchase and synthesis.

Affinity.

Independently of the above modeling, NBD-556 was modeled and docked to the CD4-bound structure of the HIV gp120 core (PDB code 1G9M) using Insight II/Discover Software (Accelrys Software, Inc., San Diego, Calif.). The NBD-556 structure model was constructed with Molecular Builder and Sketcher and the gp120 core structure was cleaned with the Biopolymer program. Simulated Annealing docking (SA-docking) was performed with the Affinity program (Halgren, supra). The binding site for NBD-556 docking was limited to a 15-Å radius from the center of the Phe 43 cavity, and the final energy minimization was performed in 1,000 steps. Discover/CVFF force field was applied for the docking calculations and the docked poses were analyzed in the Analysis module/Insight II.

Example II

Rescue of the Infectivity of sCD4-Treated HIV

This example shows the rescue of the infectivity of sCD4-treated HIV by rapid attachment to cells.

While soluble CD4 (sCD4) typically inhibits HIV infection of CD4$^+$CCR5$^+$ cells, enhancement of HIV infection of CCR5$^+$ cells lacking CD4 is sometimes seen after sCD4 treatment. (Sullivan et al. *J. Virol.* 72:6332-6338 (1998)). Sensitivity to these effects varies among different HIV strains. (Sullivan et al. *J. Virol.* 69:4413-4422 (1995)). Applicants examined the sensitivity to sCD4 of recombinant HIV viruses (designated HIV(AD8) and HIV(YU2), respectively) pseudotyped with the Env gps of the primary HIV isolates AD8 and YU2, which have similar binding affinities for sCD4. (Zhang et al. *Biochemistry* 40:1662-1670 (2001); Zhang et al. *J. Biol. Chem.* 276:39577-39585 (2001).) In $CD4^+CCR5^+$ target cells, sCD4 inhibited the infectivity of HIV(AD8) and HIV(YU2) with $IC_{50}$ values of 0.6 and 4 μg/ml, respectively (FIG. 1*a*). In $CD4^-CCR5^+$ cells, sCD4 activated infection of HIV(AD8) much more efficiently than that of HIV(YU2).

A similar pattern of HIV activation and inactivation was observed for compound II of the present invention. The affinity of compound II for the HIVYU2 gp120 Env gp ($K_d$=760 nM) is significantly lower than that of sCD4 ($K_d$=~2 nM). Nevertheless, at proportionately higher concentrations, compound II resembled sCD4, inhibiting HIV infection of $CD4^+CCR5^+$ cells and enhancing infection of $CD4^-CCR5^+$ cells (FIG. 1*b*). For both sCD4 and compound II, the enhancement of infection of cells lacking CD4 became progressively less efficient at higher concentrations; in some cases, decreases in viral infectivity were associated with escalating doses. These observations indicate the existence of a concentration-dependent, virus-inhibitory process superimposed on the activation process.

Because virus attachment to cells in culture progresses in a slow, diffusion-dependent manner (Haim et al. *J. Virol.* 79:622-625 (2005); Andreadis et al. *J. Virol.* 74:3431-3439 (2000)), significant time intervals can elapse between virus binding by compounds of the present invention and the association between virus and cell. Thus, the diminished capacity of the compounds of the present invention to enhance infection of $CD4^-CCR5^+$ cells at higher concentrations might reflect the involvement of time-dependent as well as concentration-dependent processes that abrogate infectivity after activation occurs. To test this possibility, Applicants examined the effect of neutralizing concentrations of sCD4 on HIV(YU2) infection when the time interval between sCD4-virus binding and virus-cell attachment was reduced. For this purpose, Applicants applied a system that magnetically controls virus motion to eliminate viral dependence on passive diffusion for cell attachment; this system allows near-complete transfer of the virus inoculum to the cell-bound state within one minute. (Haim et al. *J. Virol.* 79:622-625 (2005); Haim et al. *J. Virol.* 81:3525-3534 (2007)). When HIV(YU2) was briefly incubated with a high concentration of sCD4 and then added to $CD4^-CCR5^+$ cells, infection occurred only when the virus was magnetically adsorbed to the cells (FIG. 1*c*). These results are consistent with the existence of a time-dependent process that decreases HIV infectivity after activation by sCD4.

Example III

Conformational Stability of the CD4-Activated gp120

This example demonstrates the conformational stability of the CD4-activated gp120 intermediate.

To investigate the conformational stability of the sCD4-activated Env gp intermediate, Applicants monitored changes over time in the exposure of the coreceptor-binding site on gp120 and the HR1 coiled coil on gp41 after pulse activation by sCD4. For this purpose, Applicants developed an enzyme-linked immunosorbent assay (ELISA) that utilizes live cells as a platform for expression of Env gp complexes. COS-1 cells that express the HIVYU2 Env gps were pulse-activated with sCD4 at 37° C. for 3 minutes and incubated at 37° C. for different time periods. The following probes were then added: 1) monoclonal antibody 48d, which binds to a gp120 epitope that overlaps the coreceptor-binding site (Thali et al. *J. Virol.* 65:6188-6193 (1991)); or 2) the C34-Ig protein, which is composed of the C34 peptide corresponding to the gp41 HR2 region linked to the Fc constant region of human IgG1. (Si et al. *Proc. Natl. Acad. Sci. U.S.A.* 101:5036-5041 (2004).) C34-Ig binds to the hydrophobic groove formed at the interface of the HR1 coiled-coil helices. (Si et al. supra) The sCD4 pulse significantly enhanced the binding of the 48d antibody to the HIV Env gps (FIG. 2*a*); the time interval between the sCD4 pulse and addition of the 48d antibody did not affect the level of 48d binding observed. Thus, after the sCD4-induced conformational change, the epitope of the 48d antibody remains stably exposed over the time period examined.

In contrast to the above results, the exposure of the C34-Ig binding site after the sCD4 pulse was transient at 37° C. (FIG. 2*b*). Although sCD4 efficiently bound to the Env gp complex and induced the formation/exposure of the HR1 groove at 4, 25 and 37° C., this state was stable only at lower temperatures (FIG. 2*c*). The loss of exposure of the HR1 groove was not reversible by repeated pulsing of the Env gp complexes with saturating concentrations of sCD4.

Given the constant level of 48d antibody binding to the sCD4-pulsed Env gp-expressing cells, the observed time-dependent decrease in C34-Ig binding cannot be attributed to changes in cell-surface levels of the Env gps, as might occur due to gp120 shedding. (Orloff et al. *J. Virol.* 67:1461-1471 (1993)). Moreover, Applicants observed that sCD4 binding to the cells remained constant over the time period examined. Simultaneous measurement of C34-Ig and sCD4 levels bound to the Env gp-expressing cells at different time points after the sCD4 pulse demonstrated a gradually decreasing capacity of C34-Ig to bind despite constant levels of bound sCD4.

After engagement of sCD4, the HIV Env gp complex undergoes conformational changes that result in formation/exposure of the gp120 coreceptor-binding site and the gp41 HR1 groove. However, despite continued engagement of sCD4 and stable exposure of the 48d epitope on gp120, the induced Env gp intermediate undergoes a spontaneous temperature-dependent and apparently irreversible change of conformation.

Example IV

Decay of Exposure of the HR1 Groove

This example shows the decay of exposure of the HR1 groove on the Env gps from different HIV strains.

The decay profile of sCD4-induced HR1 groove exposure was determined for a panel of Env gps from primary and laboratory-adapted HIV strains. Measurements were conducted at room temperature (24-26° C.) to slow the rate of decay, allowing greater accuracy. Interestingly, a wide range of stabilities of the HR1 groove-exposed state was observed in the different HIV Env gps (FIG. 3*a*). For example, the YU2 and AD8 Env gps exhibited half-lives of 5 and 100 minutes, respectively. These differences did not result from differential affinity for CD4, because Env gps with similar capacities for binding sCD4 demonstrated markedly different decay rates of HR1 groove exposure. Applicants also found that the deletion of the gp41 cytoplasmic tail had no effect on the stability of the CD4-activated intermediate, even though the cell-surface level of Env gp expression was increased, as expected. (Wyss et al. *J. Virol.* 75:2982-2992 (2001).)

Env gps from the dual-tropic $HIV_{89.6}$ and $HIV_{KB9}$ exhibited highly stable sCD4-induced intermediates that did not appreciably decay at room temperature. For these Env gps, the half-lives of the HR1-exposed state measured at 37° C. were 16 and 17 minutes, respectively.

Example V

Stability of the HR1 Groove and Functional Stability of HIV Env Gps

This example shows a correlation between stability of the HR1 groove and functional stability of HIV Env gps after sCD4 exposure.

Applicants devised a strategy to measure changes over time in the capacity of sCD4-activated virus to infect $CD4^-CCR5^+$ cells. First, recombinant, luciferase-expressing viruses were associated with magnetite nanoparticles and immobilized on tissue-culture plates by constant application of a magnetic field. Next, the immobilized viruses were pulsed with sCD4 for 3 minutes and incubated at 25° C. for different time periods. Then, $CD4^-CCR5^+$ cells were added and immediately pelleted onto the immobilized viruses. Infectivity was assessed by measuring luciferase activity in the cells 48 hours later. The levels of initial infectivity for viruses pseudotyped with the different HIV Env gps were significantly increased by incubation with sCD4. However, infectivity subsequently declined at different rates for viruses with different Env gps (FIG. 3*b*). Similar to the stability of HR1 groove exposure, the rate of decay of infectivity was highly dependent upon temperature. At room temperature, the half-life of infectivity exhibited by the sCD4-treated viruses pseudotyped with different HIV Env gps correlated well with the half-life of the HR1 groove-exposed state following incubation with sCD4 ($R^2$=0.898, FIG. 3*c*).

Assuming that the linear regression model generated using the data obtained at 25° C. applies to the situation at 37° C., the half-lives of HIV infectivity were estimated by fitting the half-lives of HR1 groove exposure measured at 37° C. to the model. For the most stable Env gps (from $HIV_{89.6}$ and $HIV_{KB9}$), Applicants estimated a maximal half-life of infectivity of 5-7 minutes at 37° C.

Applicants compared the infectious half-lives of viruses with different HIV Env gps without treatment (using $CD4^+CCR5^+$ cells) and following incubation with sCD4 (using $CD4^-CCR5^+$ cells). Incubation of the viruses at 37° C. for increasing time periods in the absence of sCD4, followed by infection of $CD4^+CCR5^+$ cells, revealed a gradual reduction of infectivity, with half-lives ranging from 6.9 to 12.1 hours. However, no correlation between the functional stability of the native and sCD4-bound states of each of the Env gps was observed.

Applicants conclude that after engagement of sCD4, HIV undergoes a transient phase of activation, during which attachment to cells that express CCR5 will allow entry to occur. However, this activated state is short-lived and is followed by apparently irreversible structural rearrangements and loss of infectivity. Thus, at any given time point after exposure to sCD4, HIV infectivity represents the combined result of an activation process and progression through the activated intermediate state to inactivation.

Example VI

Metastable Activation Induced by Small-Molecule CD4 Mimic

This example shows the metastable activation of gp120 induced by a small-molecule CD4 mimic.

CD4-mimetic compounds exemplified by NBD-556 and compound II induce conformational changes in the HIV Env gps similar to those induced by sCD4. (Schon et al. *Biochemistry* 45:10973-10980 (2006).) These changes include formation/exposure of both the coreceptor-binding site on gp120 and the HR1 groove on gp41. The similarity between the effects of compound II and sCD4 on HIV infection of $CD4^+$ and $CD4^-$ cells, shown in FIGS. 1*a* and 1*b*, indicated that compound II can also induce transiently activated intermediate states in the HIV Env gps. To examine this possibility, Applicants compared the decay profiles associated with sCD4 and compound II. Applicants examined the YU2 and AD8 Env gps, which exhibit dramatic differences in the decay rate of the sCD4-induced intermediate. For each of these Env gps, sCD4 and compound II induced identical decay profiles, both for HR1 groove exposure and for infectivity as shown in FIG. 4. These results indicate that sCD4 and compound II induce a similar, transient intermediate state in the HIV Env gps. Moreover, the differences in decay rates between the AD8 and YU2 Env gps were evident for both sCD4 and compound II, indicating that the stability of the induced state is determined by intrinsic properties of the Env gps rather than by the activating agent.

Example VII

Stable gp120 Intermediate Induced by Cell-Surface CD4

This example demonstrate that a more stable Env gp intermediate is induced by cell-surface CD4.

Figure 5A:
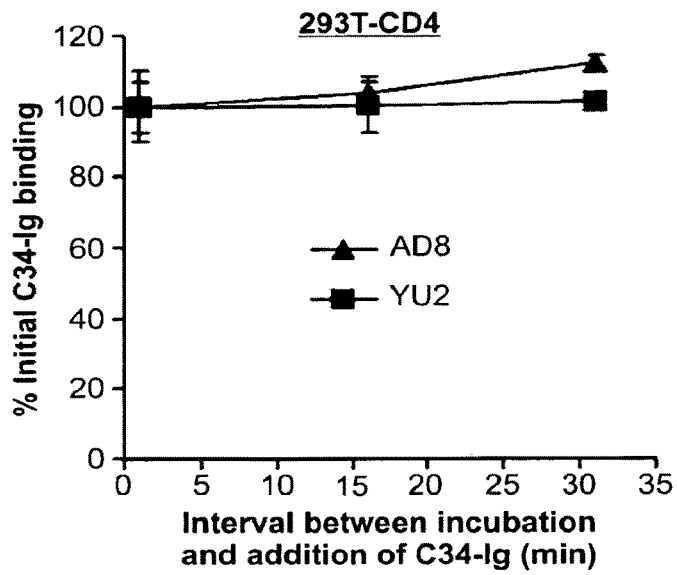

To examine the longevity of the activated intermediate induced during the normal HIV entry process, Applicants examined the stability of HR1 groove exposure after the binding of the Env gps to cell-surface CD4. For this purpose, 293T cells that express CD4, but not CCR5, were used to activate the HIV Env gps expressed on COS-1 cells. Pilot experiments demonstrated that the observed increases in C34-Ig binding to the Env gp-expressing cells depended on the presence of CD4 on the activating cell, and were not observed for mutant Env gp YU2-GS8, which binds CD4 efficiently but does not expose the HR1 groove in response. Relative to the effects of sCD4 or compound II, the HR1 groove exposure consequent to activation by cell-surface CD4 was long-lived as shown in FIG. 5a. The AD8 and YU2 Env gps, which exhibited significant differences in the half-lives of HR1 groove exposure after activation by sCD4, both demonstrated stable intermediates following activation by cell-surface CD4.

During HIV entry, CCR5 binding to the CD4-induced Env gp intermediate promotes progression along the path to virus entry. (Dragic et al. Nature 381:667-673 (1996).) Differences in the longevity of the CD4-induced state would be predicted to manifest themselves as an altered dependency on the density of target cell CCR5. To test this, the CCR5 available on CD4-expressing cells for interaction with the HIV Env gps was varied in two ways: 1) the addition of increasing amounts of compound A, a CCR5 inhibitory compound (Madani et al. J. Virol. 81:532-538 (2007)); and 2) transfection of different amounts of a CCR5-expressing plasmid.

Compound A

Figure 5B:
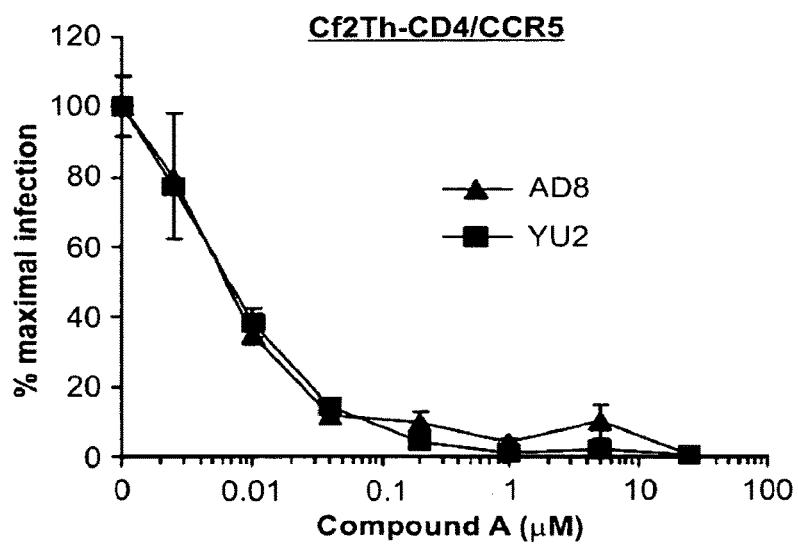
Figure 5C:
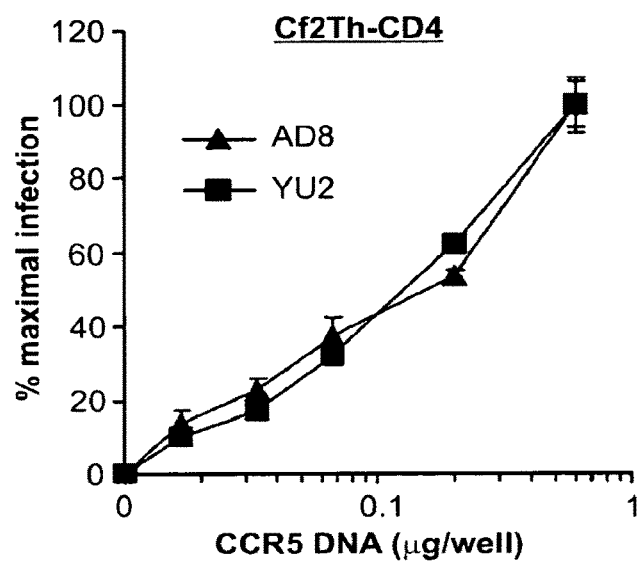
Figure 5D:
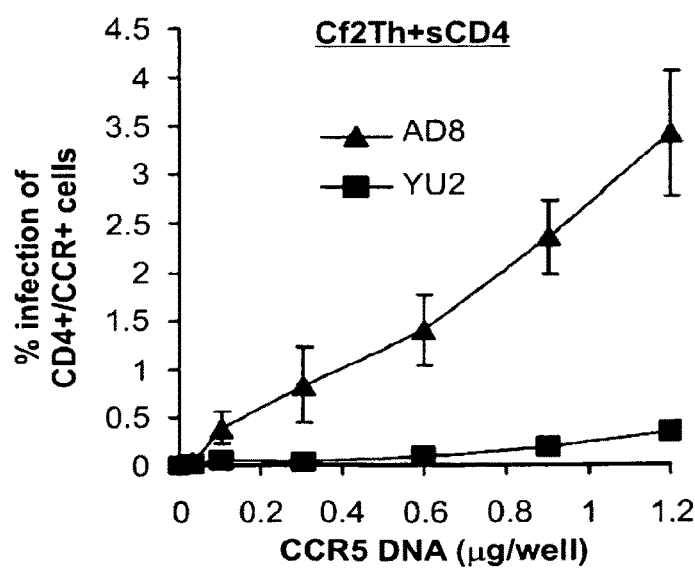

The cells were then exposed to HIV(AD8) or HIV(YU2) and the efficiency of infection measured. HIV(AD8) and HIV(YU2) behaved indistinguishably in response to variations in the CCR5 available on target cells expressing CD4 as shown in FIGS. 5b and 5c. In contrast, when sCD4 was used to activate infection of Cf2Th cells expressing different levels of CCR5, entry by HIV(AD8) was significantly better than that HIV(YU2) as shown in FIG. 5D. These results are consistent with the existence of a relatively long-lived Env gp intermediate being induced by CD4 expressed on the target membrane.

Example VIII

NBD-556 can replace CD4 in HIV Infection

This Example shows NBD-556 can replace CD4 in HIV infection.

To examine the ability of NBD-556 to replace CD4 during HIV infection, recombinant HIV expressing firefly luciferase was pseudotyped with different envelope glycoproteins and incubated with $CD4^-CCR5^+$ Cf2Th-CCR5 cells in the presence of different concentrations of NBD-556. The envelope glycoproteins were derived from CCR5-using (R5) primary HIV isolates (YU2 and ADA), dual-tropic (R5×4) primary isolates (89.6 and KB9) and, as a control, the amphotropic murine leukemia virus (A-MLV). NBD-556 enhanced infection of the Cf2Th-CCR5 cells in the following order of efficiency: YU2, ADA>KB9>89.6, A-MLV as shown in FIG. 6a. This order corresponds to the affinity of the gp120 glycoproteins from these HIV isolates for CCR5, (Babcock et al. J. Biol. Chem. 276, 38433-38440 (2001); Karlsson et al. J. Exp. Med. 188:1159-1171 (1998); Staudinger et al. J. Biol. Chem. 278, 10389-10392; Wu et al. Nature 384:179-183 (1996)) and indicates that a high co-receptor-binding affinity is required to achieve CD4-independent infection in this context. Consistent with this interpretation, NBD-556 did not enhance the entry of viruses with the KB9 envelope glycoproteins into $CD4^-CXCR4^+$ Cf2Th-CXCR4 cells; the HIV gp120 affinity for CXCR4 is significantly lower than that for CCR5. ((Babcock et al. J. Biol. Chem. 276, 38433-38440 (2001)). Likewise, the envelope glycoproteins of the laboratory-adapted CXCR4-using (X4) HIV isolates, HXBc2, bound NBD-556 weakly (see below) and were not functionally enhanced by NBD-556 for entry into Cf2Th-CXCR4 cells. However, NBD-556 dramatically enhanced infection of Cf2Th-CCR5 cells by viruses containing a chimeric HIV envelope glycoprotein (HX(YU2 V3)) in which the HXBc2 gp120 third variable (V3) loop was replaced by that of the YU2 HIV isolate as shown in FIG. 6b; this chimeric envelope glycoprotein exhibits a high affinity for the CCR5 co-receptor. (Choe et al. Cell 114, 161-170 (2003); Sullivan et al. J. Virol. 72:6332-6338 (1998); Xiang et al. J. Virol. 79:6068-6077 (2005)). Thus, NBD-556 can replace CD4 during infection of CCR5+ cells by viruses with a variety of HIV envelope glycoproteins, provided that the envelope glycoproteins exhibit sufficient affinity for CCR5.

Example IX

NBD-556 Interacts with the Conserved Core of the HIV gp120

This Example shows NBD-556 interacts with the conserved core of the HIV gp120 glycoprotein.

The direct binding of $^3$H-labeled NBD-556 to gp120 glycoprotein variants was measured as shown in FIG. 7a. NBD-556 bound YU2 gp120 efficiently, but HXBc2 gp120 only moderately. The chimeric HXBc2 gp120 with the substitution of the YU2 V3 loop bound NBD-556 more efficiently than w.t. YU2. Both YU2 and HXBc2 gp120 and chimeric envelope bound control $^3$H-labeled BMS-806 similarly. These results are consistent with the observed susceptibility of viruses with these envelope glycoproteins to enhancement by NBD-556.

The gp120 core protein lacks the V1, V2 and V3 hypervariable loops and the N and C termini of gp120. (Kwong et al. Nature 393:648-659 (1998)). The binding of [$^3$H]-NBD-556 to the YU2 gp120 core was tested in the absence and presence of the 17b anti-gp120 antibody; the 17b antibody preferentially recognizes the CD4-bound conformation of gp120 and blocks chemokine receptor binding. (Thali et al. J. Virol. 65:6188-6193 (1991); Trkola et al. Nature 384:184-187 (1996); Wu et al. Nature 384:179-183 (1996).) Weak binding of NBD-556 to the YU2 gp120 core was detected in the absence of the 17b antibody; NBD-556 binding to both full-length gp120 and the gp120 core was significantly enhanced by the addition of the 17b antibody as shown in FIG. 7b. The thermodynamic cycle of NBD-556 and 17b binding to the HIVYU2 gp120 core was determined by isothermal titration calorimetry as shown in FIG. 7c. NBD-556 bound weakly to the gp120 core (calculated $K_d$=40 μM), but exhibited an approximately 25-fold increase in affinity for the gp120 core bound to the 17b antibody ($K_d$=1.5 μM). Conversely, the 17b antibody preferentially recognized the NBD-556-bound form of the gp120 core. BIAcore analysis confirmed that NBD-556 could efficiently recognize the gp120 core-17b complex ($K_d$=6.6 μM). Apparently, NBD-556 preferentially recognizes the CD4-bound conformation of HIV gp120. Moreover, NBD-556 binds the relatively conserved portion of gp120 retained in the core molecule.

Example X

NBD-556-gp120 Interaction

This Example shows modeling of the NBD-556-gp120 core interaction.

As NBD-556 preferentially recognizes the CD4-bound conformation of the HIV gp120 core, Applicants used the available x-ray crystal structures of gp120-CD4 complexes (Kwong et al. *Nature* 393:648-659 (1998)) to model the binding of NBD-556 to HIV gp120 in the CD4-bound state. Models produced independently using Glide (Friesner et al. *J. Med. Chem.* 47:1739-1749 (2004); Halgren et al. *J. Med. Chem.* 1750-1759 (2004)), Gold (Jones et al. *J. Mol. Biol.* 267:727-748 (1997)) and Accelrys (Kuntz et al. *Accounts Chem. Res.* 27:117ff (1994); Luty et al. *J. Comp. Chem.* 16, 454-464 (1995); Stouten et al. *C. Molecular Stimulation* 10 (1993)) predicted remarkably similar binding modes, with the chloro-phenyl ring of NBD-556 projecting into the Phe 43 cavity of gp120 as shown in FIG. 8. Based on the predicted binding mode, the chlorophenyl ring of NBD-556 sits 6.5 Å deeper in the Phe 43 cavity than the phenyl ring of Phe 43 of CD4. Predicted aromatic-aromatic stacking interactions between the NBD-556 chloro-phenyl ring and Trp 427, Phe 382 and Trp 112 likely stabilize the NBD-556-gp120 complex. Three other gp120 residues, Val 255, Thr 257 and Met 475 are within 4 Å of the NBD-556 chlorophenyl group situated in the bottom of the gp120 cavity. Docking is also indicative of hydrogen bonds between one of the NBD-556 oxalamide nitrogens and gp120 backbone carbonyls in the neck of the cavity.

Scyllatoxin or charybdotoxin scaffolds have been used to create CD4-mimetic miniproteins. (Vita et al. *Proc. Natl. Acad. Sci. U.S.A.* 96:13091-13096 (1999); Zhang et al. *Biochemistry* 38:9405-9416 (1999)). X-ray crystal structures have demonstrated the similar ways in which Phe 23 of some scyllatoxin-based miniproteins and Phe 43 of CD4 contact gp120. (Huang et al. *Structure* 13:755-768 (2005).) In one scyllatoxin derivative, CD4M33, a biphenyl group at residue 23 reaches into the Phe 43 cavity, increasing the affinity for gp120. (Huang et al. *Structure* 13:755-768 (2005); Martin et al. *Nat. Biotechnol.* 21:71-76 (2003).) The predicted position of the chlorophenyl ring in the bound NBD-556 models is similar to that of the distal phenyl ring of CD4M33 as shown in FIG. 8. However, the NBD-556 chlorophenyl ring projects slightly deeper into the Phe 43 cavity than the CD4M33 biphenyl group.

Example XI

NBD-556 Phenyl Ring Para Position Modification

This Example shows the effects of NBD-556 phenyl ring para position modifications on CCR5 binding and viral enhancement, as well as the effects on $K_d$ and thermodynamic parameters.

The models predict that changes in the NBD-556 phenyl ring and oxalamide linker will affect gp120 binding and/or functional mimicry of CD4. To test this, the compounds of the present invention were synthesized and tested for the ability to bind gp120 and to enhance CCR5 binding and infection of CCR5$^+$ cells as shown in FIG. 9. NBD-557, which has a bromo group at the para position of the phenyl ring, bound gp120 and activated CCR5 binding and entry comparably to NBD-556. Para substitution of the phenyl ring chloro and bromo groups with either larger or smaller groups resulted in decreased enhancement of CCR5 binding and/or HIV entry.

Example XII

NBD-556 Phenyl Ring Ortho/Meta Position Modification

This Example shows the effects of NBD-556 phenyl ring ortho/meta position modifications on CCR5 binding and viral enhancement, as well as the effects on $K_d$ and thermodynamic parameters.

To explore additional options for modifying the interactions of NBD-556 with the Phe 43 cavity of gp120, different groups were substituted at the ortho and meta positions of the NBD-556 phenyl ring. NBD-556 was chosen over NBD-557 for these studies because of better solubility, which resulted in improved reproducibility in the biological assays. The size and nature of the group at the meta position significantly affected the affinity and virus-enhancing ability of the NBD-556 derivatives as shown in FIG. 10. Compound II, with a fluoro group at the meta position, exhibited the highest affinity for gp120 and the most potent stimulation of HIV infection of CCR5$^+$ cells. Larger groups at the meta position resulted in decreases in both gp120 binding and viral enhancement. Compound II specifically inhibited HIVYU2 infection of cells expressing CD4 and CCR5; this contrasts with several of the other meta-substituted analogues, which exhibited only non-specific inhibitory effects on infection of viruses with HIV and A-MLV envelope glycoproteins. Ortho substitutions generally resulted in loss of gp120 binding and viral enhancement (data not shown). Likewise, replacement of the phenyl ring and/or oxalamide linker resulted in compounds that did not detectably bind gp120 and exhibited no specific enhancement or inhibition of HIV infection (data not shown). These results are consistent with modeling predictions in which the Phe 43 cavity constrains the nature and size of the phenyl and oxalamide substituents that can be tolerated in functionally active compounds.

Example XIII

NBD-556 Piperidine Ring Modification

This Example shows the effects of NBD-556 piperidine modifications on CCR5 binding and viral enhancement, as well as the effects on $K_d$ and thermodynamic parameters.

Figure 11:
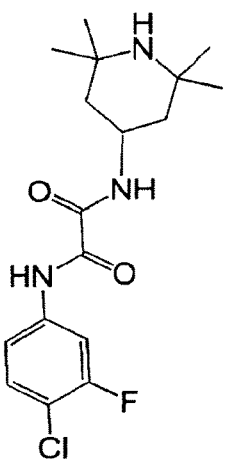
Figure 11:
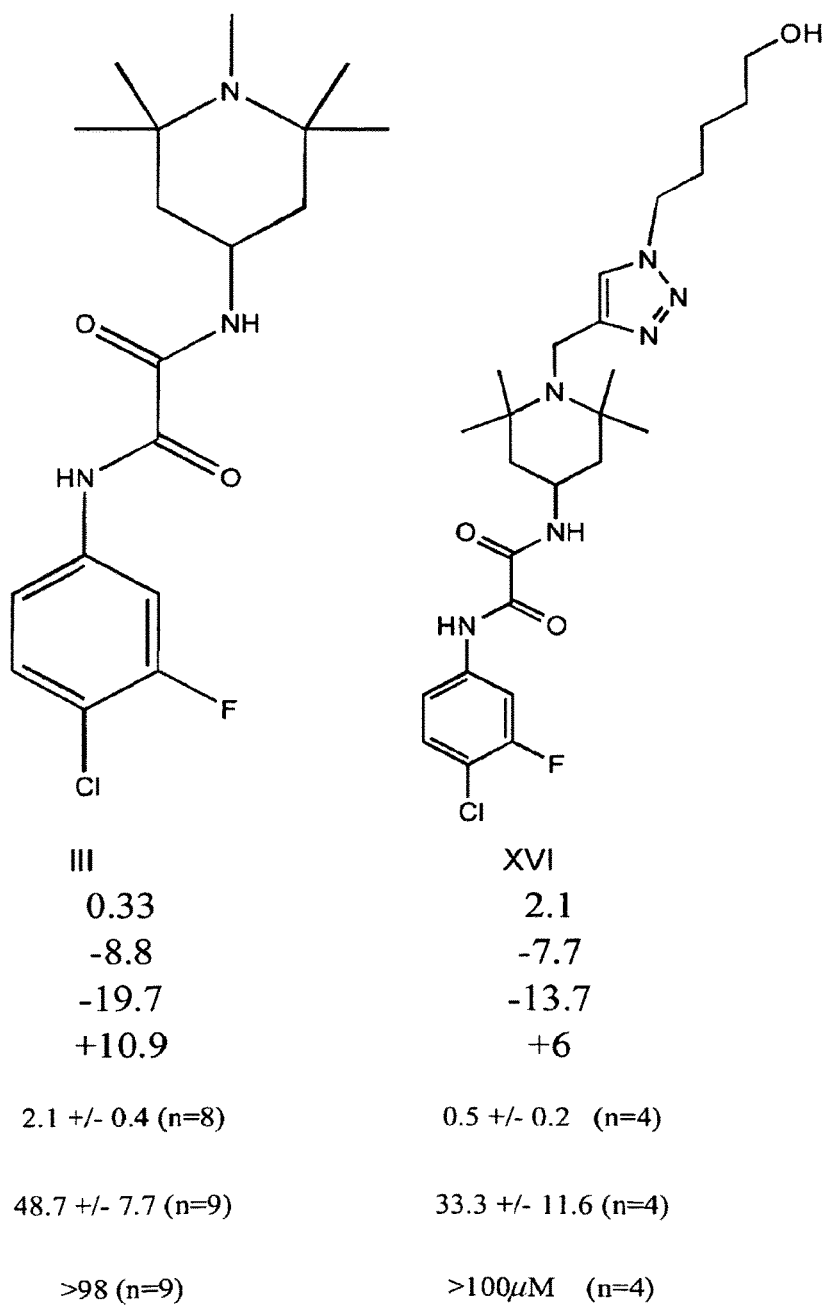
Figure 11:
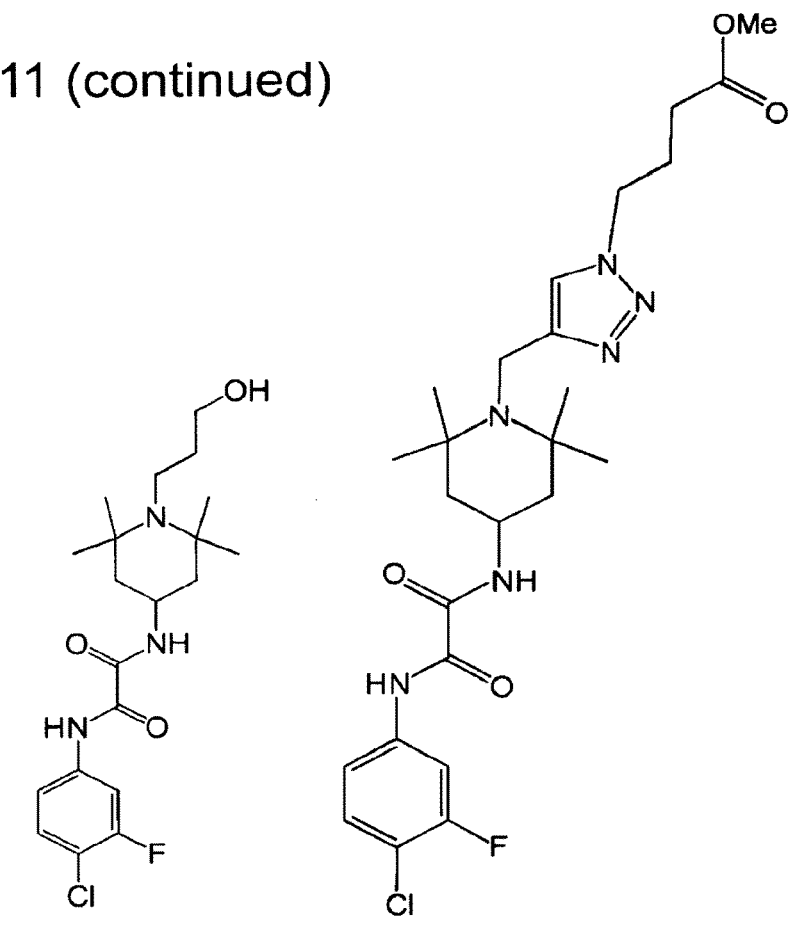

The affinity of compound II for HIV-1 gp120 can be improved or maintained by the introduction of substituents on the nitrogen of the piperidine ring as shown in FIG. 11. A methyl group, for example, increases affinity for gp120 and lowers the IC$_{50}$, while maintaining specificity for HIV-1 (see compound III). Even larger groups can be accommodated on the piperidine ring nitrogen, with efficient and specific inhibition of HIV-1, for example, compounds XVI, XVII and XVIII. These results support the modeled binding mode of NBD-556 analogues, with the piperidine moiety oriented in the vestibule of the Phe43 cavity, allowing larger substituents to be accommodated. Additional modifications of the piperidine ring of compound II can allow contacts with a greater number of gp120 residues in the Ph343 vestibule. For example, binding of piperidine ring substituents to aspartic acid 368 or isoleucine 371 of gp120 can increase the gp120-binding affinity and anti-HIV-1 potency of the compounds. Finally, the ability to place substituents on the piperidine ring nitrogen of compound II facilitates further modification of these substituents by click chemistry and other means, and also allows the linking of these compounds to dendrimers to create polyvalent inhibitors of HIV-1 infection.

Example XIV

Binding Thermodynamics

This Example describes binding thermodynamics of compounds of the present invention that exhibited gp120 affinity.

Figure 12A:
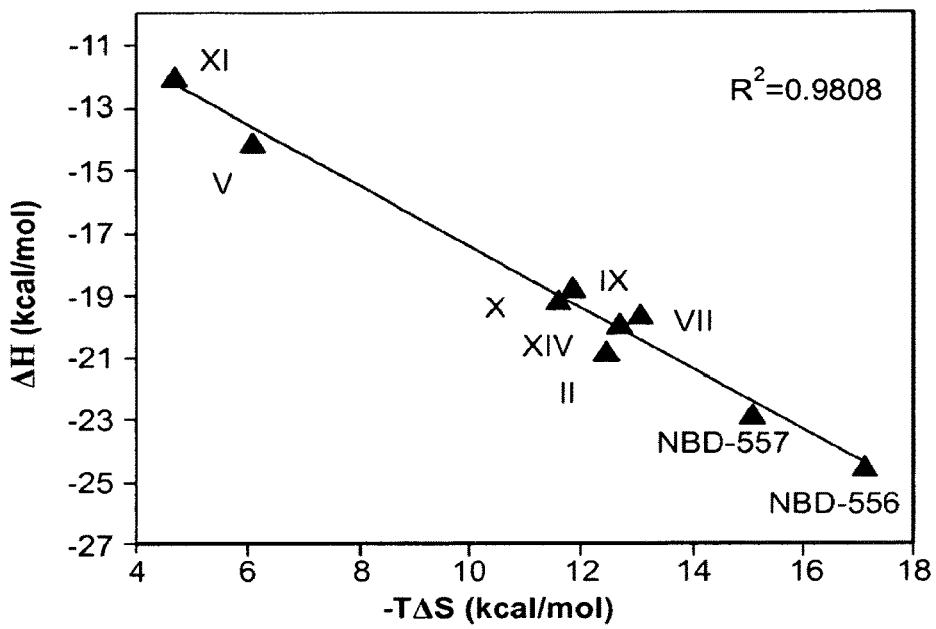

Binding thermodynamics were analyzed for compounds of the present invention that exhibited detectable gp120 affinity. The binding affinity was sensitive to any modifications at the para position of the phenyl ring and the binding of compound VI in FIG. 9, having only a hydrogen atom in the para position, was too weak to be determined by ITC. As expected for compounds with only modest differences in affinity, i.e., similar ΔG values, a strong correlation between the enthalpy change (ΔH) and the entropy change (-TΔS) associated with gp120 binding was observed as shown in FIG. 12a. These compounds, however, have different properties, conferred to them by their different thermodynamic signatures. The enthalpy changes associated with the binding of all of these phenyl ring variants were much larger than those expected from the modeled interactions of the compounds with the gp120 protein. Moreover, differences in -TΔS values of up to 11 kcal/mol were observed for the binding of closely related compounds. These results indicate that, to varying degrees, the compounds of the present invention induce a large structuring of gp120. The major contributions to the observed entropy changes originate from conformational and solvation changes. Solvation changes are related to the heat capacity change, which is negative (Schön et al. "Thermodynamics of binding of a low-molecular-weight CD4 mimetic to HIV gp120," *Biochemistry* 45:10973-10980 (2006)) and consistent with a favorable desolvation entropy. (Luque and Freire "Structure-based prediction of binding affinities and molecular design of peptide ligands," Methods Enzymol. 295:100-127 (1998).) The observation that the overall entropy change is unfavorable indicates that desolvation is unable to overcome the unfavorable conformational entropy due to structuring. In fact, it has been estimated that binding of NBD-556 induces the structuring of 67 residues on average. (Schön et al. "Thermodynamics of binding of a low-molecular-weight CD4 mimetic to HIV gp120," *Biochemistry* 45:10973-10980 (2006).)

Figure 12B:
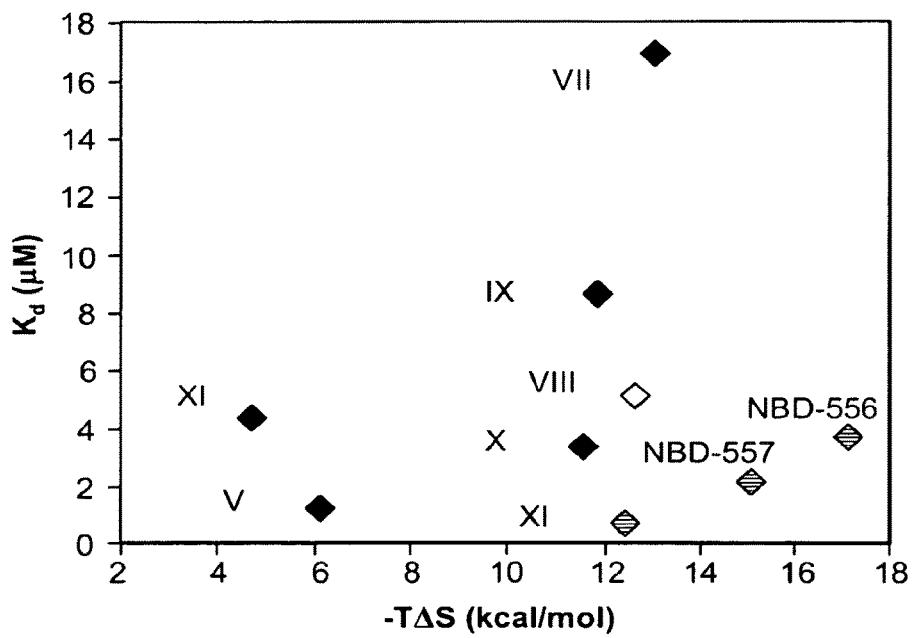

The relationship between thermodynamic parameters and the enhancement of HIV entry into CCR5+ cells was examined as shown in FIG. 12b. NBD-556 analogues that stimulated HIV infection exhibited both high affinities for gp120 and large unfavorable entropy changes upon gp120 binding. Thus, high affinity for gp120 is beneficial but not sufficient for the ability of compounds of the present invention to replace CD4 in the HIV entry process. The conformational fixation of gp120, reflected in the large entropic change observed during compound-gp120 binding, apparently contributes to CD4 mimicry.

One of the para-substituted analogues such as compound VIII, which bound gp120 efficiently but minimally stimulated HIV infection, inhibited the enhancement of HIV infection by NBD-556. This observation, together with the thermodynamic data, indicates a model in which compounds of the present invention bind, with varying degrees of CD4 mimicry, to the same general region of gp120.

Example XV

Effects of gp120 Changes near the Phe 43 Cavity

This Example describes the effects of gp120 mutations near the Phe 43 cavity on the activity of NBD-556 and compounds of the present invention.

Figure 13A:
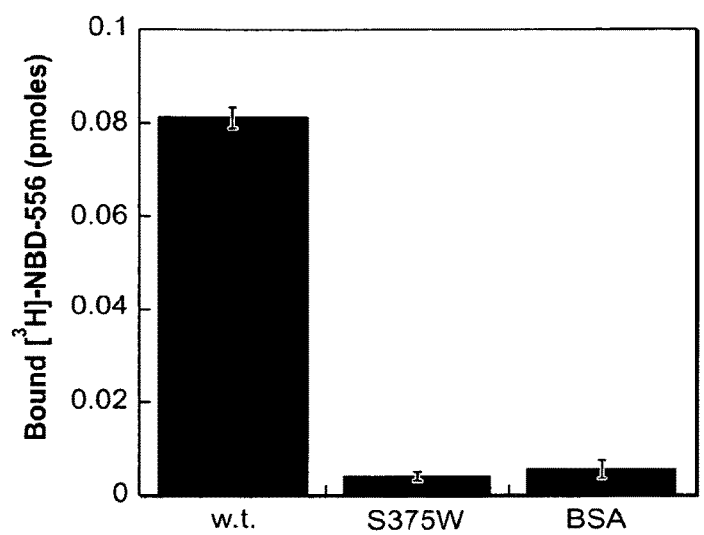
Figure 13B:
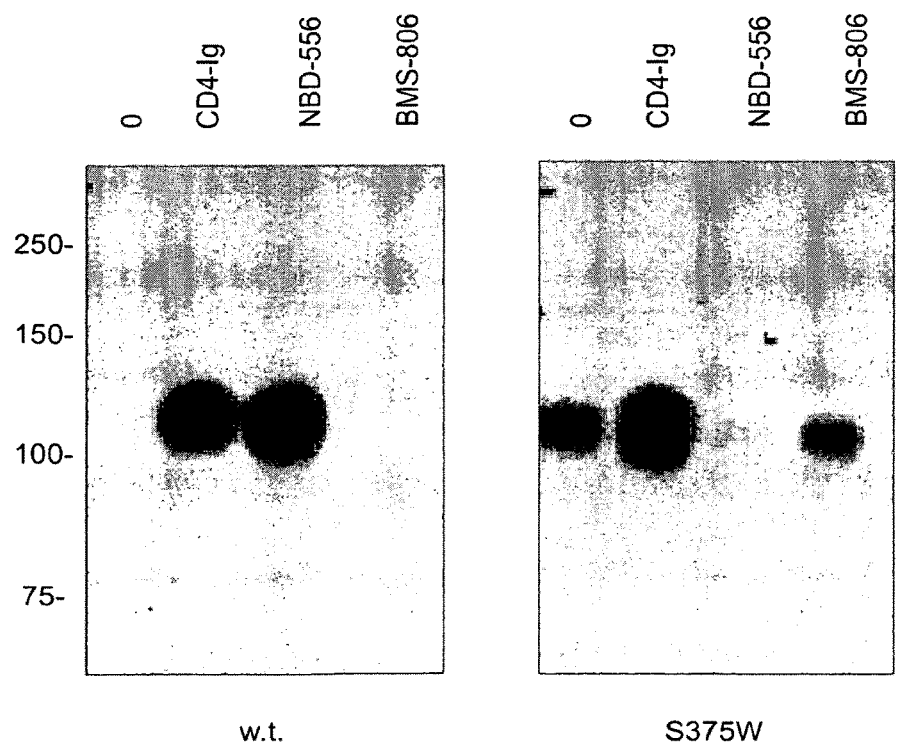
Figure 13C:
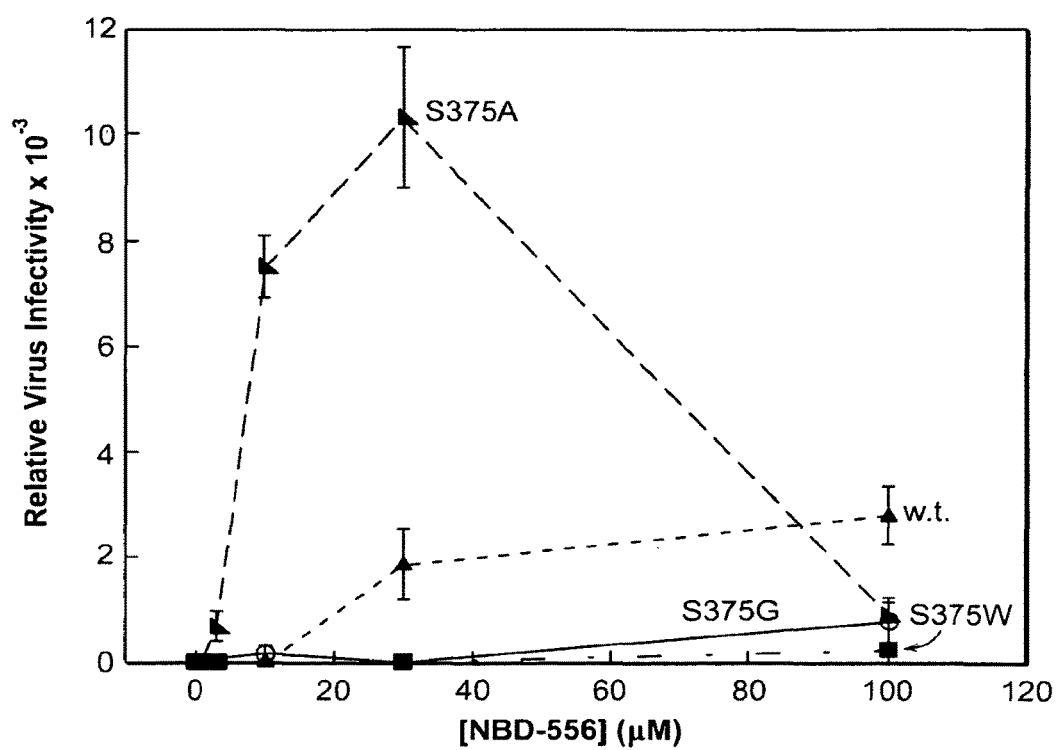
Figure 13D:

To test the models further, the interaction of mutants of the HIVYU2 gp120 glycoprotein with NBD-556 and compounds of the present invention was examined. Substitution of gp120 Ser 375 with a tryptophan residue fills the Phe 43 cavity but does not disrupt CD4 binding. (Xiang et al. *J. Virol.* 76:9888-9899 (2002).) Compared with the wild-type (w.t.) HIVYU2 gp120, the S375W mutant bound radiolabeled NBD-556 inefficiently as shown in FIG. 13a. The binding of the S375W gp120 to Cf2Th-CCR5 cells was induced by a soluble form of CD4 but not by NBD-556 as shown in FIG. 13b. A control compound, BMS-806, which also binds HIV gp120 (Lin et al. *Proc. Natl. Acad. Sci. USA.* 100; 11013-11018 (2003)), did not enhance the binding of either w.t. or S375W gp120 to CCR5+ cells. The infection of viruses with the S375W mutant envelope glycoproteins was not enhanced by NBD-556, in contrast to the significant enhancement observed for viruses with the w.t. envelope glycoproteins as shown in FIG. 13c. These results indicate that filling the Phe 43 cavity with the indole side chain of tryptophan prevents NBD-556 binding.

Example XVI

Effects of gp120 Changes Near the Phe 43 Cavity

This Example describes the effects of changes in several gp120 residues that line the Phe 43 cavity on the sensitivity of HIV to enhancement by compounds of the present invention.

Figure 14:
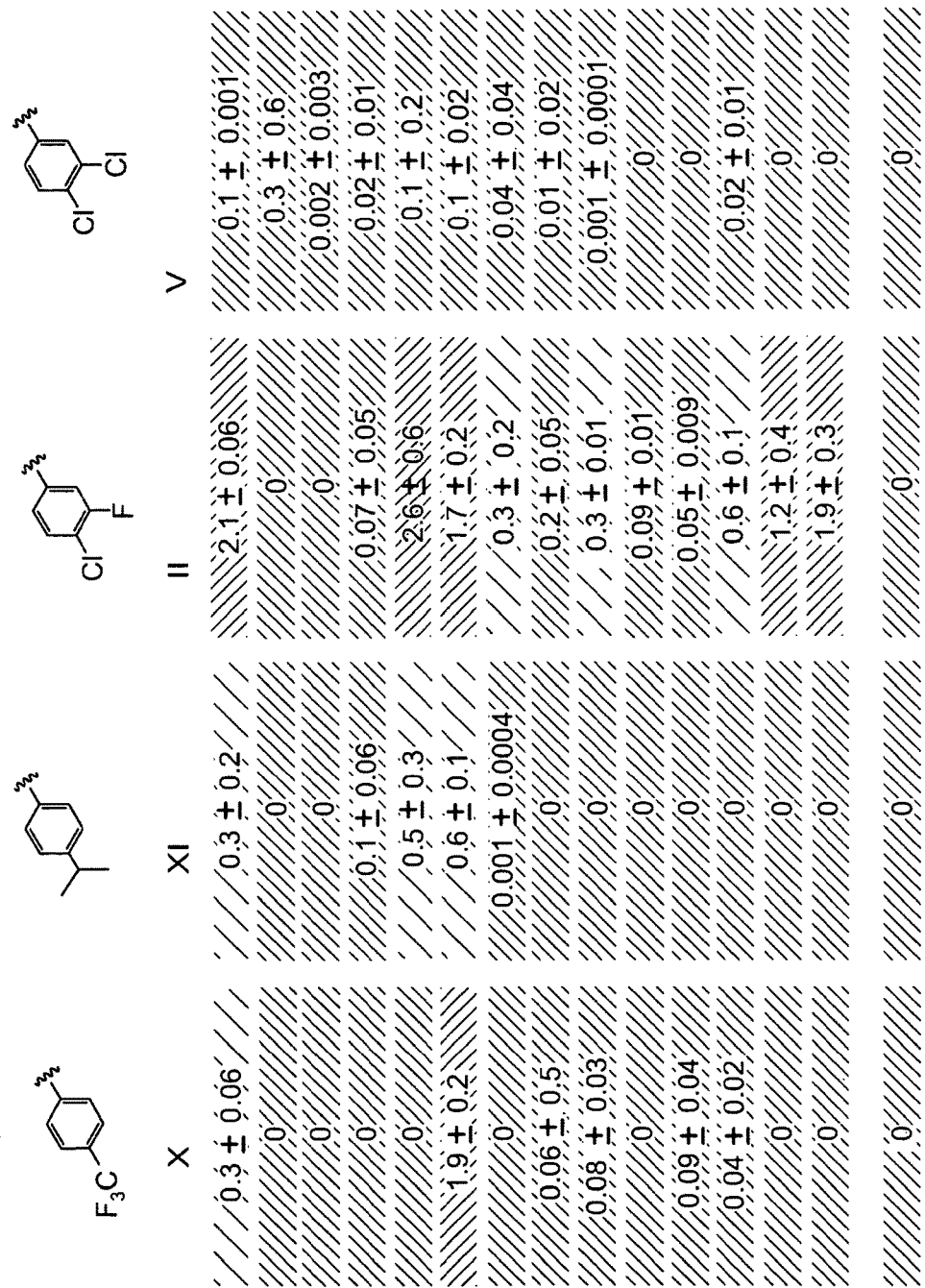
Figure 15A:
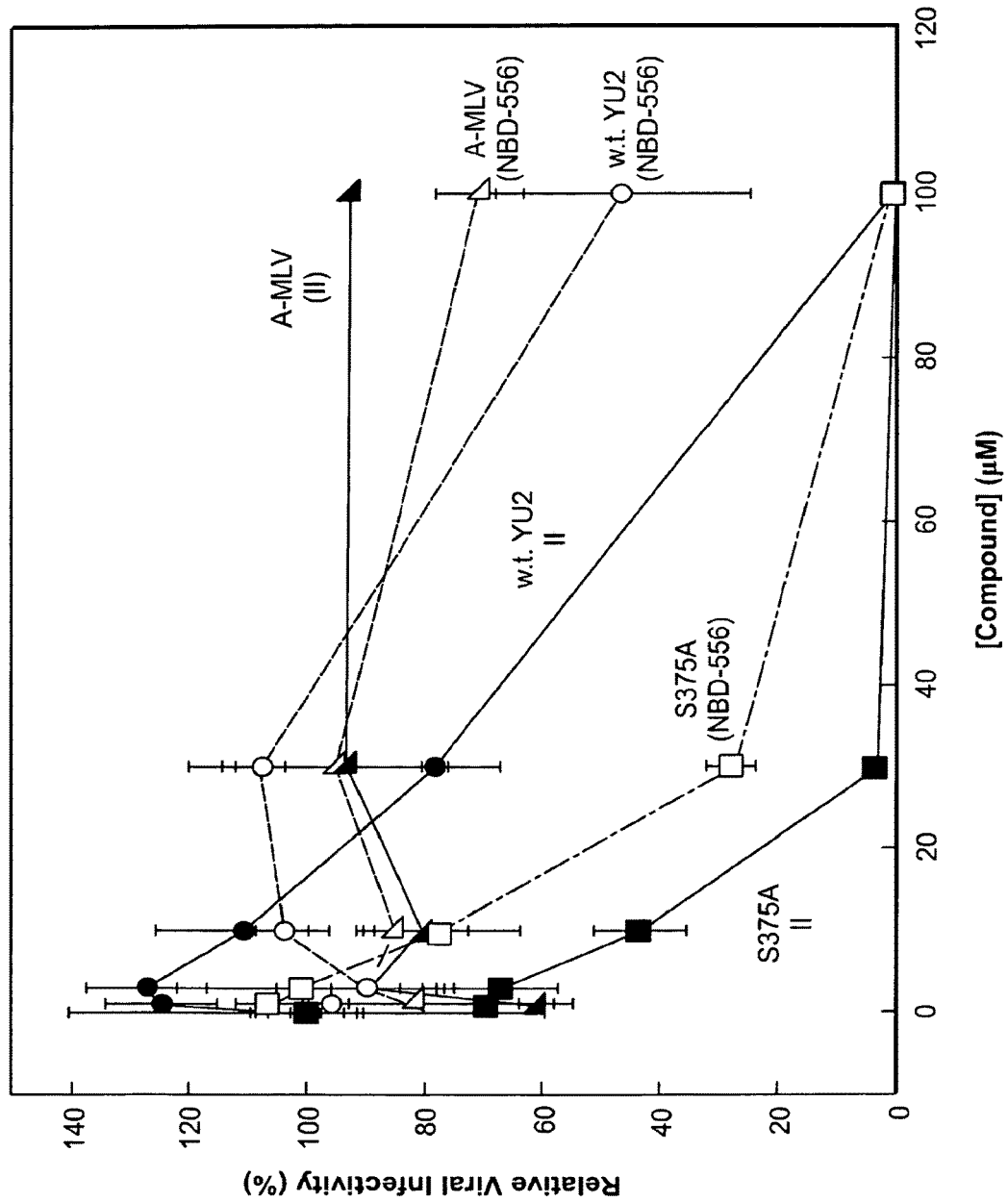
Figure 15B:
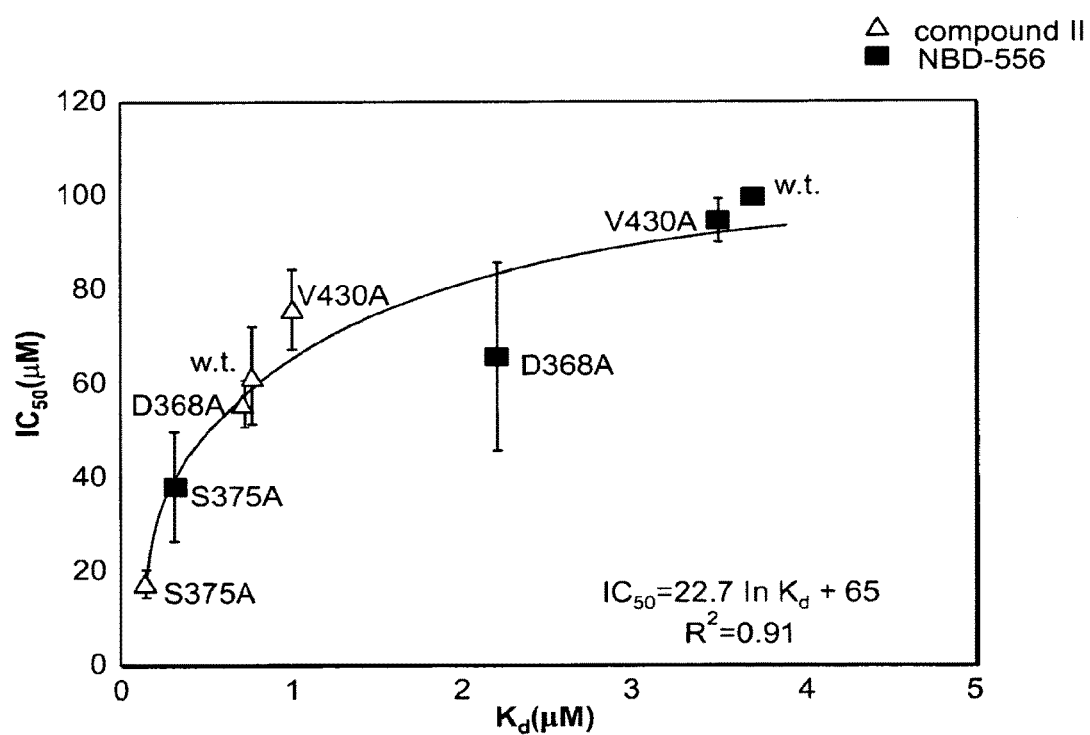
Figure 16:
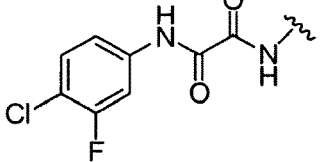
Figure 16:
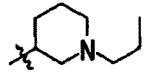
Figure 16:
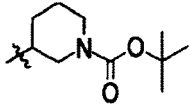
Figure 16:
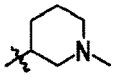
Figure 16:
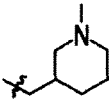
Figure 16:
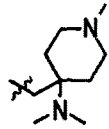
Figure 16:
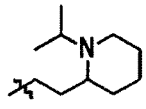
Figure 16:
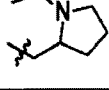
Figure 16:
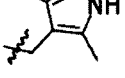
Figure 16:
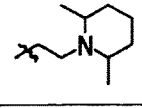
Figure 16:
Figure 16:
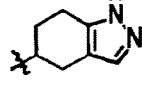
Figure 16:
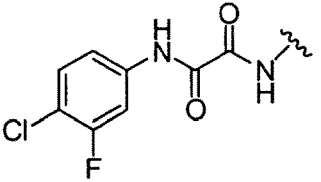
Figure 16:
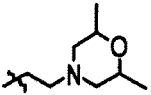
Figure 16:
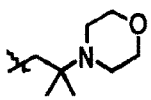
Figure 16:
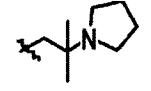
Figure 16:
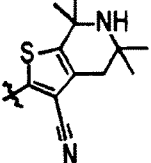
Figure 16:
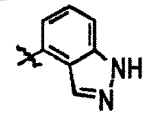
Figure 16:
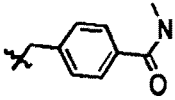
Figure 16:
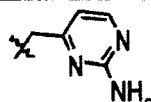
Figure 16:
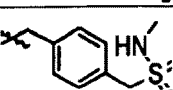
Figure 16:
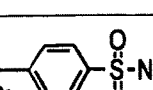
Figure 16:
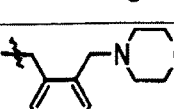
Figure 16:
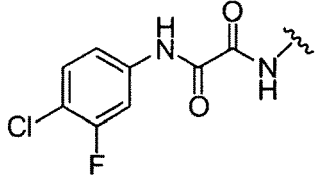
Figure 16:
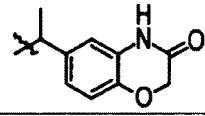
Figure 16:
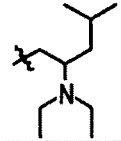
Figure 16:
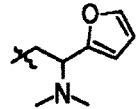
Figure 16:
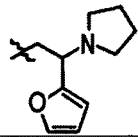
Figure 16:
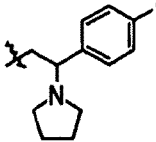
Figure 16:
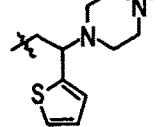
Figure 16:
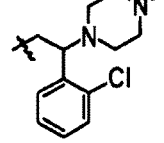
Figure 16:
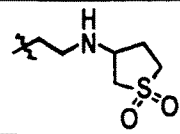
Figure 16:
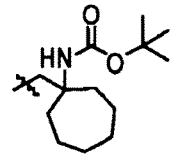

The effects of changes in several gp120 residues that line the Phe 43 cavity on the sensitivity of HIV to enhancement by a panel of compounds of the present invention, shown in FIG. 14, were examined. Two analogues, NBD-557 and compound II, that efficiently enhanced infection by viruses with w.t. HIVYU2 envelope glycoproteins did not activate the entry of viruses with the S375W envelope glycoproteins. The replacement of gp120 Ser 375 with glycine dramatically reduced HIV sensitivity to enhancement by any of the compounds of the present invention as shown in FIG. 13c and FIG. 14, indicating that some element of the Ser 375 side chain contributes to NBD-556 efficacy. In some x-ray crystal structures of the CD4-bound gp120 (1G9M) (Kwong et al. *Structure* 8:1329-1339 (2000)), Ser 375 anchors a water molecule in the base of the Phe 43 cavity; this water molecule, which was not displaced in docking NBD-556 with Gold, likely affects the shape and flexibility of the cavity. Viruses bearing envelope glycoproteins with Ser 375 changed to alanine exhibited greater enhancement by NBD-556 than the viruses with w.t. envelope glycoproteins as shown in FIG. 13c and FIG. 14. Moreover, compounds VIII, X and XI stimulated the entry of viruses with the S375A change more efficiently than they enhanced w.t. virus infection as shown in FIG. 14. These results indicate that the hydroxyl group of Ser 375 is detrimental to the binding and/or activity of compounds of the present invention that contain large para-phenyl substituents.

Alteration of gp120 Asp 368 to alanine reduced the basal level of replication of HIV in cells expressing CD4 and CCR5 (data not shown), consistent with the importance of this residue for CD4 binding. (Kwong et al. Nature 393: 648-659 (1998); Olshevsky et al. *J. Virol.* 64:5701-5707 (1990); Wyatt and Sodroski *Science* 280:1884-1888 (1998).) The infectivity of the D368A mutant viruses in $CD4^{-}CCR5^{+}$ target cells was enhanced by incubation with NBD-556, compound II and compound XI. In the presence of the first two compounds, the entry of viruses with the D368A envelope glycoproteins into Cf2Th-CCR5 cells was similar to the levels achieved by w.t. viruses. Viruses with the D368A envelope glycoproteins were not enhanced by NBD-557, in contrast to w.t. viruses. This indicates that NBD-556 and NBD-557 differ in their sensitivity to changes in Asp 368 of gp120.

Changes in other gp120 residues lining the Phe 43 cavity or vestibule (Val 255, Thr 257, Glu 429 and Val 430) significantly decreased the enhancement of virus infection by compounds of the present invention. Although the Glu 429 side chain projects away from the Phe 43 vestibule, it forms a salt bridge with Lys 121 and thus can help to stabilize the CD4-bound conformation of gp120. (Kwong et al. Nature 393:648-659 (1998).) Replacement of Glu 429 with a lysine residue, which disrupts this salt bridge, eliminated the activation of infection for NBD-556, NBD-557 and compound II. Substitution of an alanine residue for Glu 429 was less disruptive of NBD-556-induced virus activation, although the virus-enhancing activities of NBD-557 and compound II were significantly diminished by this change. Thus, alteration of several gp120 residues that line the Phe 43 pocket or reside in the vestibule leading into the pocket can affect, in either a positive or negative manner, the CD4-mimetic effects of NBD-556 and/or compounds of the present invention on HIV infection.

Example XVII

Binding of NBD-556 to HIV gp120 Mutants

This Example describes the use of isothermal titration calorimetry to study the binding of NBD-556 to HIV gp120 mutants.

The binding of NBD-556 to selected HIVYU2 gp120 mutants was studied by isothermal titration calorimetry. Compared with the w.t. gp120 glycoprotein, both the D368A and S375A gp120 mutants bound NBD-556 and compound II with higher affinity as shown in Table 1.

TABLE 1

Binding affinities of NBD-556 and compound II to different gp120 variants

| HIV-1 YU2 gp120 | $K_d$ (μM) | |
|---|---|---|
| glycoprotein | NBD-556 | Compound II |
| w.t. | 3.7 | 0.80 |
| D368A | 2.2 | 0.72 |
| S375A | 0.31 | 0.14 |
| D368A/S375A | 0.26 | 0.083 |
| S375W | NB | NB |
| I424A | NB | NB |

TABLE 1-continued

Binding affinities of NBD-556 and compound II to different gp120 variants

| HIV-1 YU2 gp120 | $K_d$ (μM) | |
|---|---|---|
| glycoprotein | NBD-556 | Compound II |
| W427A | NB | NB |
| V430A | 3.5 | 1.0 |
| M475A | NB | NB |

NB—no detectable binding.

A mutant gp120 glycoprotein, D368A/S375A, that combined both changes bound NBD-556 and compound II more tightly than either of the mutants with individual changes. These results agree with measurements of radiolabeled NBD-556 binding to these gp120 glycoproteins (data not shown). Several gp120 mutants (S375W, I424A, W427A and M475A) with changes in residues that contact the Phe 43 cavity did not detectably bind NBD-556 in the isothermal titration calorimetric analyses (Table 1). These results support the importance of gp120 residues near the Phe 43 cavity in binding NBD-556 and compounds of the present invention, and lend credence to the docked binding mode. FIG. **13*d*** illustrates the location of gp120 residues in which changes affect the binding and/or virus-enhancing ability of compounds of the present invention, underscoring the proximity of these residues to the Phe 43 cavity.

Example XVIII

Compound-gp120 Affinity and HIV Inhibition

This Example shows the relationship between compound affinity for gp120 and HIV inhibitory activity.

As natural target cells for HIV in vivo all express CD4, future efforts to create antiviral agents directed against the Phe 43 cavity of gp120 would benefit from an understanding of the properties of these compounds that correlate with inhibition of HIV infection of $CD4^{+}CCR5^{+}$ cells. Gp120 variants and compounds of the present invention were used that exhibit a range of affinities to examine the contribution of this parameter to virus inhibition. Infection of Cf2Th-CD4/CCR5 cells by viruses with the w.t. YU2 envelope glycoproteins was inhibited only by high concentrations of NBD-556 (50% inhibitory concentration ($IC_{50}$)=100 μM) as shown in FIG. **15*a*. On the other hand, compound II inhibited w.t. virus infection with an $IC_{50}$ of 54 μM, consistent with the higher affinity of this analogue for the HIVYU2 gp120 glycoprotein. Viruses with the S375A envelope glycoproteins, which exhibit a higher affinity for NBD-556 and compound II, were inhibited by both compounds with $IC_{50}$ values of 10-20 μM. There is a close relationship between the $K_d$ of the compound for the particular envelope glycoprotein variant and the $IC_{50}$ as shown in FIG. 15*b***. That the $K_d$ values are less than the $IC_{50}$ values is not, as many factors can potentially influence the inhibition of virus infection that are not expected to affect the binding of the compounds to gp120 monomers. Nonetheless, it is apparent that increasing the binding affinity of a small-molecule CD4 mimetic results in improved antiviral effect.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A compound of formula I:

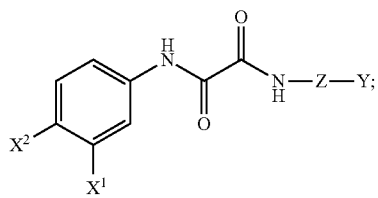

wherein:
Z is absent;
Y is optionally substituted cycloalkyl or optionally substituted aryl;
$X^1$ is fluorine;
$X^2$ is halogen;
or a pharmaceutically acceptable salt thereof.

2. The compound of claim 1, wherein Y is cyclopropyl, cyclobutyl, cyclopentyl, cyclohexyl, cycloheptyl, cyclooctyl, adamantyl, [3.3.0]bicyclooctane, [4.3.0]bicyclononane, [4.4.0]bicyclodecane, [2.2.2]bicyclooctane, fluorenyl, phenyl, naphthyl, indanyl, or tetrahydronaphthyl, each of which may be optionally substituted.

3. The compound of claim 1, wherein Y is:

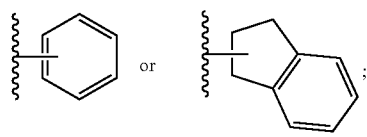

each of which may be optionally substituted.

4. The compound of claim 1, that is:

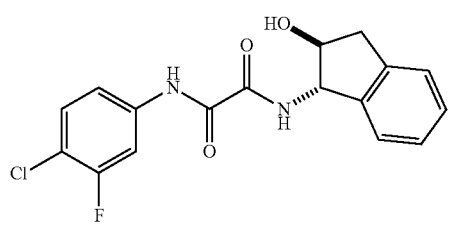

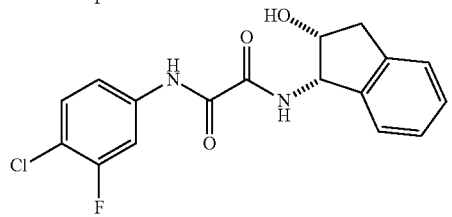

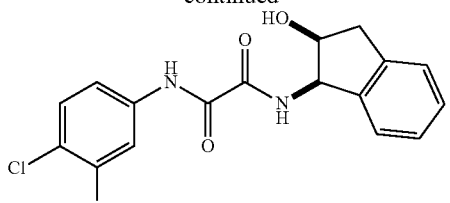

or

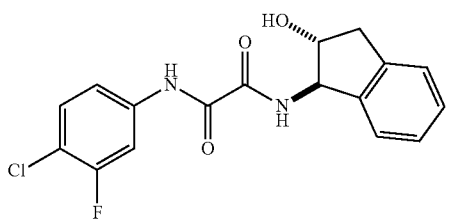

or a pharmaceutically acceptable salt thereof.

5. The compound of claim 1, that is:

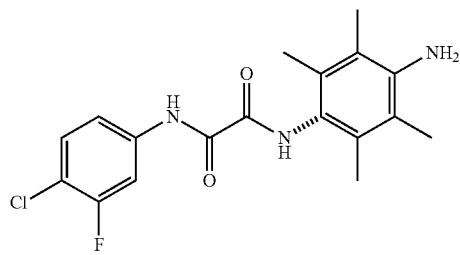

or a pharmaceutically acceptable salt thereof.

6. The compound of claim 1 that is:

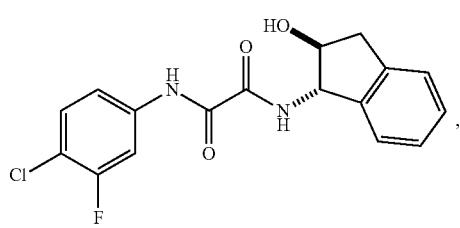

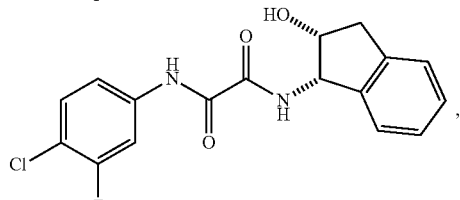

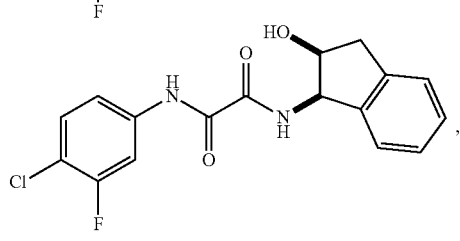

or

-continued
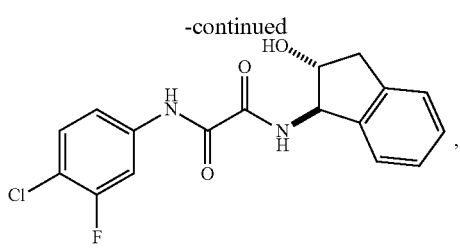
7. The compound of claim 1 that is
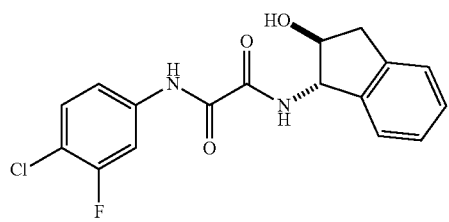
or a pharmaceutically acceptable salt thereof.
8. The compound of claim 1, that is:
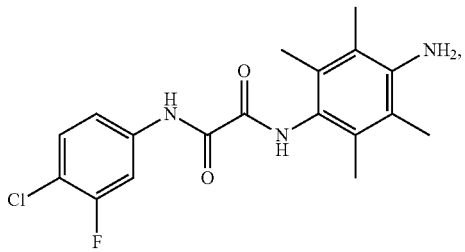 [SMILES: Cc1c(C)c(NC(=O)C(=O)Nc2ccc(Cl)c(F)c2)c(C)c(C)c1N]
* * * * *

UNITED STATES PATENT AND TRADEMARK OFFICE
CERTIFICATE OF CORRECTION

PATENT NO. : 9,776,963 B2
APPLICATION NO. : 13/128549
DATED : October 3, 2017
INVENTOR(S) : Joseph G. Sodroski et al.

Page 1 of 1

It is certified that error appears in the above-identified patent and that said Letters Patent is hereby corrected as shown below:

In the Specification

Before "BACKGROUND OF THE INVENTION" at Column 1, Line 13, insert the following Heading and paragraph:
--GOVERNMENT RIGHTS
This invention was made with government support under Grant Nos. CA124755, CA056550, GM056550, and AI024755 awarded by the National Institutes of Health. The government has certain rights in the invention.--.

Signed and Sealed this
Twenty-sixth Day of November, 2019

Andrei Iancu
*Director of the United States Patent and Trademark Office*